(12) United States Patent
Green et al.

(10) Patent No.: US 10,428,387 B2
(45) Date of Patent: Oct. 1, 2019

(54) TREATING CHRONIC MYELOGENOUS LEUKEMIA (CML)

(71) Applicant: University of Massachusetts, Boston, MA (US)

(72) Inventors: Michael R. Green, Boylston, MA (US); Leyuan Ma, Holden, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/308,673

(22) PCT Filed: May 14, 2015

(86) PCT No.: PCT/US2015/030908
§ 371 (c)(1),
(2) Date: Nov. 3, 2016

(87) PCT Pub. No.: WO2015/175846
PCT Pub. Date: Nov. 19, 2015

(65) Prior Publication Data
US 2017/0183741 A1    Jun. 29, 2017

Related U.S. Application Data

(60) Provisional application No. 62/032,117, filed on Aug. 1, 2014, provisional application No. 61/994,689, filed on May 16, 2014.

(51) Int. Cl.
| | |
|---|---|
| *A61K 31/506* | (2006.01) |
| *A61K 31/519* | (2006.01) |
| *C12Q 1/6886* | (2018.01) |
| *G01N 33/574* | (2006.01) |

(52) U.S. Cl.
CPC .......... *C12Q 1/6886* (2013.01); *A61K 31/506* (2013.01); *A61K 31/519* (2013.01); *G01N 33/57426* (2013.01); *C12Q 2600/106* (2013.01); *C12Q 2600/156* (2013.01); *C12Q 2600/158* (2013.01); *G01N 2333/91205* (2013.01); *G01N 2800/52* (2013.01)

(58) Field of Classification Search
CPC .. A61K 31/506; A61K 31/519; C12Q 1/6886; C12Q 2600/106; C12Q 2600/156; C12Q 2600/158; G01N 2333/91205; G01N 2800/52; G01N 33/57426
See application file for complete search history.

(56) References Cited

U.S. PATENT DOCUMENTS 7,307,071 B2 * 12/2007 Lyons .................. A61K 31/00
514/183
2009/0215792 A1   8/2009 Bhalla
2011/0189192 A1   8/2011 Cooper
2013/0296318 A1  11/2013 Huang

OTHER PUBLICATIONS

Kim et al. 2011, Blood Cancer Journal, 1(8), pp. 1-10.*
Jing et al. 2012 Mol. Cancer Ther., 11(3), pp. 720-729.*
Aceves-Luquero et al., "ERK2, but Not ERK1, Mediates Acquired and "De novo" Resistance to Imatinib Mesylate: Implication for CML Therapy," PLoS One, Jul. 2009, 4: e6124.
Aderem, "The MARCKS brothers: a family of protein kinase C substrates," Cell, Nov. 1992,71: 713-716.
An et al., "BCR-ABL tyrosine kinase inhibitors in the treatment of Philadelphia chromosome positive chronic myeloid leukemia: a review," Leuk Res, 2010, 34: 1255-1268.
Andersson et al.,"K562—a human erythroleukemic cell line," International Journal of Cancer, Feb. 1979, 23: 143-147.
Baccarani et al., "Evolving concepts in the management of chronic myeloid leukemia: recommendations from an expert panel on behalf of the European Leukemia Net," Blood, Sep. 2006, 108(6):1809-20.
Bagger et al., "HemaExplorer: a database of mRNA expression profiles in normal and malignant haematopoiesis," Nucleic Acids Res, Jan. 2013, 41: D1034-1039.
Benjamini and Hochberg, "Controlling the false discovery rate: a practical and powerful approach to multiple testing," J. R. Statist. Soc. B, 1995, 57: 289-300.
Bhatia et al., "Persistence of malignant hematopoietic progenitors in chronic myelogenous leukemia patients in complete cytogenetic remission following imatinib mesylate treatment," Blood, Jun. 2003, 101: 4701-4707.
Bixby and Talpaz, "Mechanisms of resistance to tyrosine kinase inhibitors in chronic myeloid leukemia and recent therapeutic strategies to overcome resistance," Hematology, 2009, 461-476.
Bruennert et al., "Early in vivo changes of the transcriptome in Philadelphia chromosome-positive CD34+ cells from patients with chronic myelogenous leukaemia following imatinib therapy," Leukemia, 2009, 23: 983-985.
Cai et al., "Role of diacylglycerol-regulated protein kinase C isotypes in growth factor activation of the Raf-I protein kinase," Molecular and Cellular Biology, Feb. 1997, 17:732-741.
Carroll and May, "Protein kinase C-mediated serine phosphorylation directly activates Raf-1 in mmine hematopoietic cells," The Journal of Biological Chemistry, Jan. 1994, 269: 1249-1256.
Carvalho and Irizarry, "A framework for oligonucleotide microarray preprocessing," Bioinformatics, 2010, 26: 2363-2367.
Chakrabarti et al., "Elf5 inhibits the epithelial-mesenchymal transition in mammary gland development and breast cancer metastasis by transcriptionally repressing Snail2/Slug," Nature Cell Biology, Nov. 2012, 14: 1212-1222.
Chang et al., "High levels of the BCR/ABL oncoprotein are required for the MAPK-hnRNP-E2 dependent suppression of C/EBPalpha-driven myeloid differentiation," Blood, Aug. 2007, 110: 994-1003.
Chomel et al., "Leukemic stem cell persistence in chronic myeloid leukemia patients with sustained undetectable molecular residual disease," Blood, Sep. 2011, 118: 3657-3660.

(Continued)

*Primary Examiner* — Kara R McMillian
(74) *Attorney, Agent, or Firm* — Fish & Richardson P.C.

(57) ABSTRACT

Methods for treating chronic myeloid leukemia (CML), e.g., BCR-ABL inhibitor imatinib mesylate (IM)-resistant CML, using combination treatments, e.g., combined treatment with a BCR-ABL inhibitor, e.g., IM, and a MEK inhibitor, e.g., trametinib.

14 Claims, 18 Drawing Sheets

Specification includes a Sequence Listing.

(56) References Cited

OTHER PUBLICATIONS

Chu et al., "BCR/ABL kinase inhibition by imatinib mesylate enhances MAP kinase activity in chronic myelogenous leukemia CD34+ cells," Blood, Apr. 2004, 103: 3167-174.
Colicelli, "ABL tyrosine kinases: evolution of function, regulation, and specificity," Sci Signal, Sep. 2010, 3: re6.
Corbin et al., "Human chronic myeloid leukemia stem cells are insensitive to imatinib despite inhibition of BCR-ABL activity," J Clin Invest, Jan. 2011, 121: 396-409.
Cortes et al., "Staging of Chronic Myeloid Leukemia in the Imatinib Era," Cancer, Mar. 2006, 106 (6): 1306-1315.
Daley et al., "Induction of chronic myelogenous leukemia in mice by the P210bcr/abl gene of the Philadelphia chromosome," Science, Feb. 1990, 247: 824-830.
Dean et al., "Tumour stem cells and drug resistance," Nature Reviews, Apr. 2005, 5: 275-284.
Deininger et al., "The molecular biology of chronic myeloid leukemia," Blood, Nov. 2000, 96: 3343-3356.
Donato et al., "BCR-ABL independence and LYN kinase overexpression in chronic myelogenous leukemia cells selected for resistance to STI571," Blood, 2003, 101: 690-698.
Donato et al., "Imatinib mesylate resistance through BCR-ABL independence in chronic myelogenous leukemia," Cancer Research, Jan. 2004, 64: 672-677.
Escamilla-Hernandez et al., "Genome-wide search identifies Ccnd2 as a direct transcriptional target of Elf5 in mouse mammary gland," BMC Molecular Biology, 2010, 11: 68.
Faderl et al., "The biology of chronic myeloid leukemia," N Engl J Med, Jul. 1999, 341: 164-172.
Fang et al., "MEK/ERK Dependent Activation of STAT1 Mediates Dasatinib-Induced Differentiation of Acute Myeloid Leukemia," PLOS One, Jun. 2013, 8: e66915.
Gazin et al., "An elaborate pathway required for Ras-mediated epigenetic silencing" Nature, Oct. 2007, 449: 1073-1077.
Gerber et al., "Genome-wide comparison of the transcriptomes of highly enriched normal and chronic myeloid leukemia stem and progenitor cell populations," Oncotarget, 2013, 4: 715-728.
Goldman and Melo, "Chronic Myeloid Leukemia—Advances in Biology and New Approaches to Treatment," N Engl J Med, Oct. 2003, 349 (15): 1451-64.
Graham et al., "Primitive, quiescent, Philadelphia-positive stem cells from patients with chronic myeloid leukemia are insensitive to STI571 in vitro," Blood, Jan. 2002, 99: 319-325.
Hamilton et al., "Chronic myeloid leukemia stem cells are not dependent on Bcr-Abl kinase activity for their survival," Blood, Feb. 2012, 119: 1501-1510.
Hentschel et al., "BCR-ABL- and Ras-independent activation of Raf as a novel mechanism of Imatinib resistance in CML," Int J Oncol, Sep. 2011, 39: 585-591.
Ihaka and Gentleman, "R: A language for data analysis and graphics," J. Comput. Graph Stat., 1996, 5: 299-314.
Jabbour et al., "Frequency and clinical significance of BCR-ABL mutations in patients with chronic myeloid leukemia treated with imatinib mesylate," Leukemia, 2006 20: 1767-1773.
Jiang et al., "Chronic myeloid leukemia stem cells possess multiple unique features of resistance to BCR-ABL targeted therapies," Leukemia, 2007, 21: 926-935.
Kalyuga et al., "ELF5 suppresses estrogen sensitivity and underpins the acquisition of antiestrogen resistance in luminal breast cancer," PLoS Biology, Dec. 2012, 10: e1001461.
Kantarjian et al., "Dose escalation of imatinib mesylate can overcome resistance to standard-dose therapy in patients with chronic myelogenous leukemia," Blood, Jan. 2003,101(2):473-475.
Khorashad et al., "The presence of a BCR-ABL mutant allele in CML does not always explain clinical resistance to imatinib," Leukemia, 2006, 20: 658-663.
Klinac et al., "Advances in personalized targeted treatment of metastic melanoma and non-invasive tumor monitoring," Frontiers in Oncology, Mar. 2013, 3: 1-16.

Kolch et al., "Protein kinase C alpha activates RAF-I by direct phosphorylation," Nature, Jul. 1993, 364: 249-252.
Konuma et al., "Forced expression of the histone demethylase Fbxl10 maintains self-renewing hematopoietic stem cells," Exp Hematol, Jun. 2011, 39: 697-709.
Li et al., "Activation of p53 by SIRT1 Inhibition Enhances Elimination of CML Leukemia Stem Cells in Combination with Imatinib," Cancer Cell, Feb. 2012, 21: 266-281.
Li et al., "The P190, P210, and P230 forms of the BCR/ABL oncogene induce a similar chronic myeloid leukemia-like syndrome in mice but have different lymphoid leukemogenic activity," The Journal of Experimental Medicine, May 1999, 189: 1399-1412.
Lobo et al., "The Biology of Cancer Stem Cells," Annu Rev Cell Dev Biol, Nov. 2007, 23: 675-699.
Mizuchi et al., "BCR/ABL activates Rap1 and B-Raf to stimulate the MEK/Erk signaling pathway in hematopoietic cells," Biochem Biophys Res Commun., Jan. 2005, 326: 645-651.
Mullenders and Bernards, "Loss-of-function genetic screens as a tool to improve the diagnosis and treatment of cancer," Oncogene, 2009, 28: 4409-4420.
Nambu et al., "Contribution of BCR—ABL-independent activation of ERK1/2 to acquired imatinib resistance in K562 chronic myeloid leukemia cells," Cancer Sci Jan. 2010, 101: 137-142.
National Cancer Institute: PDQ® Chronic Myelogenous Leukemia Treatment. Bethesda, MD: National Cancer Institute. Date last modified Mar. 28, 2014. Available at: http://www.cancer.gov/cancertopics/pdq/treatment/CML/HealthProfessional. Accessed Nov. 17, 2016.
Neering et al., "Leukemia stem cells in a genetically defined murine model of blast crisis CML," Blood, 2007, 110: 2578-2585.
Ohkubo et al., "A novel Ph1 chromosome positive cell line established from a patient with chronic myelogenous leukemia in blastic crisis," Leukemia Research, 1985, 9: 921-926.
Packer et al., "Nilotinib and MEK Inhibitors Induce Synthetic Lethality through Paradoxical Activation of RAF in Drug-Resistant Chronic Myeloid Leukemia," Cancer Cell, 2011, 20: 715-727.
Pellicano et al., "Concise Review: Cancer Cells Escape from Oncogene Addiction: Understanding the Mechanisms Behind Treatment Failure for More Effective Targeting," Stem Cells, Jun. 2014, 32: 1373-1379.
Pellicano et al., "The MEK inhibitor PD184352 enhances BMS-214662-induced apoptosis in CD34φCML stem/progenitor cells," Leukemia, 2011, 25: 1159-1167.
Quintas-Cardama et al., "Mechanisms of primary and secondary resistance to imatinib in chronic myeloid leukemia," Cancer Control, Apr. 2009, 16: 122-131.
Radich et al., "Gene expression changes associated with progression and response in chronic myeloid leukemia," PNAS, Feb. 2006, 103: 2794-2799.
Schonwasser et al., "Activation of the mitogen-activated protein kinase/extracellular signal-regulated kinase pathway by conventional, novel, and atypical protein kinase C isotypes," Molecular and Cellular Biology, Feb. 1998, 18: 790-798.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, Aug. 2002, 2: 117-125.
Shah et al., "Overriding imatinib resistance with a novel ABL kinase inhibitor," Science, Jul. 2004, 305: 399-401.
Silva et al., "Second-generation shRNA libraries covering the mouse and human genomes," Nat Genet, Oct. 2005, 37: 1281-1288.
Slinker, "The Statistics of Synergism," J Mol Cell Cardiol, Apr. 1998, 30: 723-731.
Smith et al., "The Role of Kinase Inhibitors in the Treatment of Patients with Acute Myeloid Leukemia," ASCO Educational Book, 2013, 313-318.
Soverini et al., "BCR-ABL kinase domain mutation analysis in chronic myeloid leukemia patients treated with tyrosine kinase inhibitors: recommendations from an expert panel on behalf of European LeukemiaNet," Blood, Aug. 2011, 118: 1208-1215.
Soverini et al., "Contribution of ABL Kinase Domain Mutations to Imatinib Resistance in Different Subsets of Philadelphia-Positive

(56) References Cited

OTHER PUBLICATIONS

Patients: By the GIMEMA Working Party on Chronic Myeloid Leukemia," Clin Cancer Res, Dec. 2006, 12: 7374-7379.
Sozeri et al., "Activation of the c-Raf protein kinase by protein kinase C phosphorylation," Oncogene, Nov. 1992, 7: 2259-2262.
Steelman et al., "JAK/STAT, Raf/MEK/ERK, PI3K/Akt and BCR-ABL in cell cycle progression and leukemogenesis," Leukemia, 2004, 18:189-218.
Suzuki et al., "PKC eta regulates occludin phosphorylation and epithelial tight junction integrity," PNAS, Jan. 2009,106: 61-66.
Takahashi et al., "VEGF activates protein kinase C-dependent, but Ras-independent Raf-MEK-MAP kinase pathway for DNA synthesis in primary endothelial cells," Oncogene, Apr. 1999, 18: 2221-2230.
ten Hoeve et al., "Tyrosine phosphorylation of CRKL in Philadelphia+ leukemia," Blood, Sep. 1994, 84: 1731-17363.
Third Party Observation in International Application No. PCT/US2015/030908, dated Feb. 16, 2016.
Ueda et al, "Protein kinase C activates the MEK-ERK pathway in a manner independent of Ras and dependent on Raf," The Journal of Biological Chemistry, 1996, 271: 23512-23519.
Uht et al., "The protein kinase C-eta isoform induces proliferation in glioblastoma cell lines through an ERK/Elk-1 pathway," Oncogene, 2007, 26: 2885-2893.
Valent, "Imatinib-resistant chronic myeloid leukemia (CML): Current concepts on pathogenesis and new emerging pharmacologic approaches," Biologics, Dec. 2007, 1: 433-448.
Von Bubnoff et al., "Resistance of Philadelphia-chromosome positive leukemia towards the kinase inhibitor imatinib (STI571, Glivec): a targeted oncoprotein strikes back," Leukemia, 2003, 17: 829-838.
Weisberg et al., "Second generation inhibitors of BCR-ABL for the treatment of imatinib-resistant chronic myeloid leukaemia," Nature Reviews, Cancer, May 2007, 7: 345-356.
Wellbrock et al., "The RAF proteins take centre stage," Nature Reviews, Molecular Cell Biology, Nov. 2004, 5: 875-885.
Zhang et al., "Effective Targeting of Quiescent Chronic Myelogenous Leukemia Stem Cells by Histone Deacetylase Inhibitors in Combination with Imatinib Mesylate," Cancer Cell, May 2010, 17: 427-442.
Zhang et al., "The Blk pathway functions as a tumor suppressor in chronic myeloid leukemia stem cells," Nat Genet, 2012, 44: 861-871.
Bhatia et al., "Abstract #: 1420: Suppression of CML Hematopoietic Progenitor Growth Following BCR/ABL-Kinase Inhibition by Imatinib Mesylate Does Not Result from MAPK Inhibition and Is Synergistically Enhanced Following Inhibition of MAPK Activity," Presented at 44th Annual Meeting of the American Society of Hematology, Philadelpha, PA, Dec. 6-10, 2002, BIOSIS, Nov. 2002, 100: 2 pages.
International Preliminary Report on Patentability on International Application No. PCT/US2015/030908, dated Dec. 1, 2016.
Ma et al., "A therapeutically targetable mechanism of BCR-ABL-independent imatinib resistance in chronic myeloid leukemia," Science Translational Medicine, Sep. 2014, 6: 252ra121 (13 pages).
Partial European Search Report in Application No. 15793586.7, dated Dec. 15, 2017, 17 pages.
Partial European Supplementary Search Report in Application No. 15793586.7, dated Nov. 10, 2017, 14 pages.
Ammoun et al. "Nilotinib alone or in combination with selumetinib is a drug candidate for neurofibromatosis type 2" Neuro-Oncology 13(7):759?766, 2011, abstract, p. 760, col. 1, para 2-3, p. 763, col. 1, para 2 to col. 2, para 1, Fig. 4.
Ma et al. "A therapeutically targetable mechanism of BCR-ABL? independent imatinib resistance in chronic myeloid leukemia" Science Translational Medicine Sep. 2014 vol. 6 Issue 252 252ra121, abstract, p. 4, col. 1, para 5 to p. 6, col. 1, para 2.
International Search Report and the Written Opinion of the International Searching Authority for PCT/US15/30908 dated Dec. 8, 2015, 15 pages.
Extended European Search Report in Application No. 15793586.7, dated Mar. 19, 2018, 11 pages.

\* cited by examiner

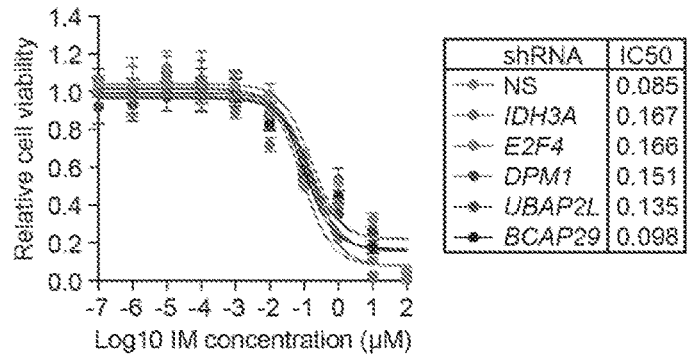
Figure 12
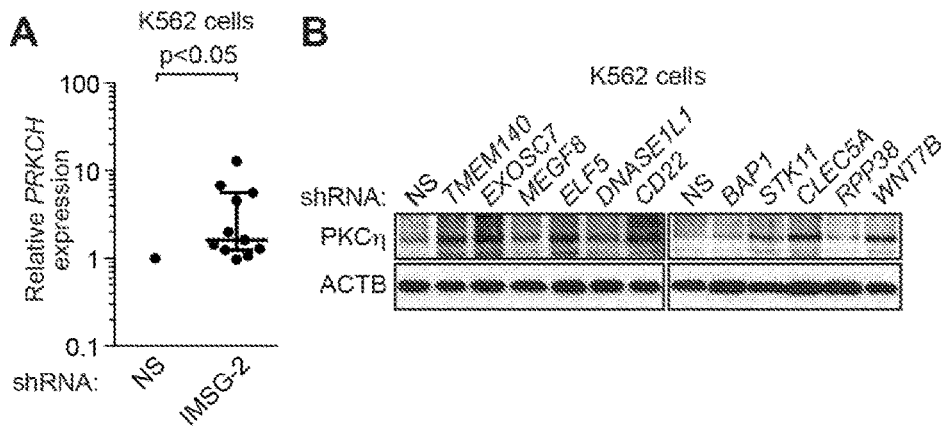
Figures 13A-B
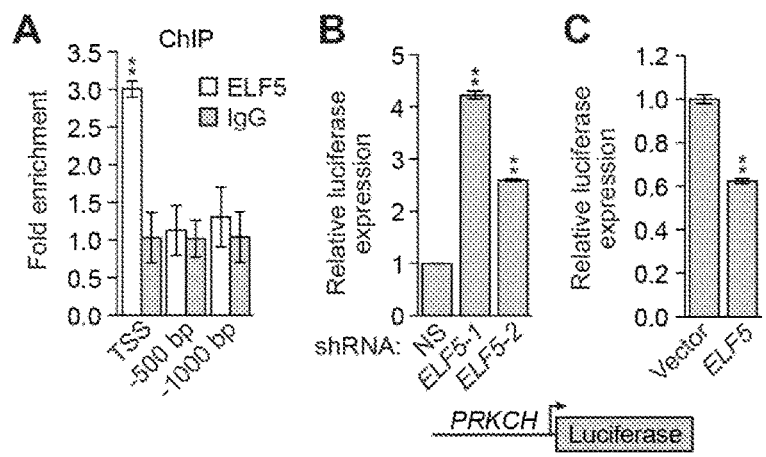
Figures 14A-C

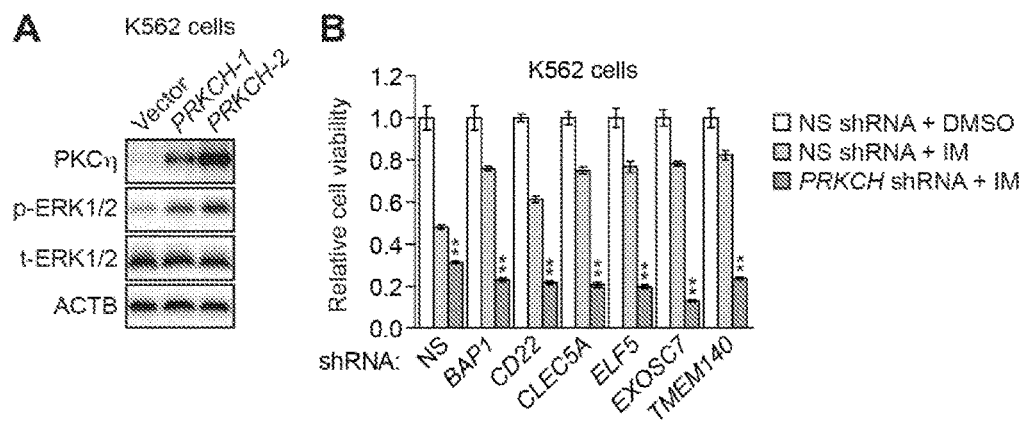
Figures 15A-B
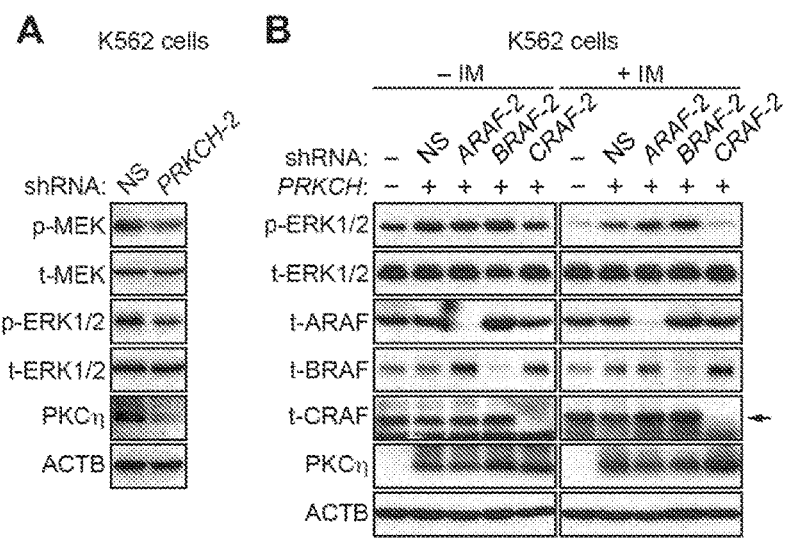
Figures 16A-B

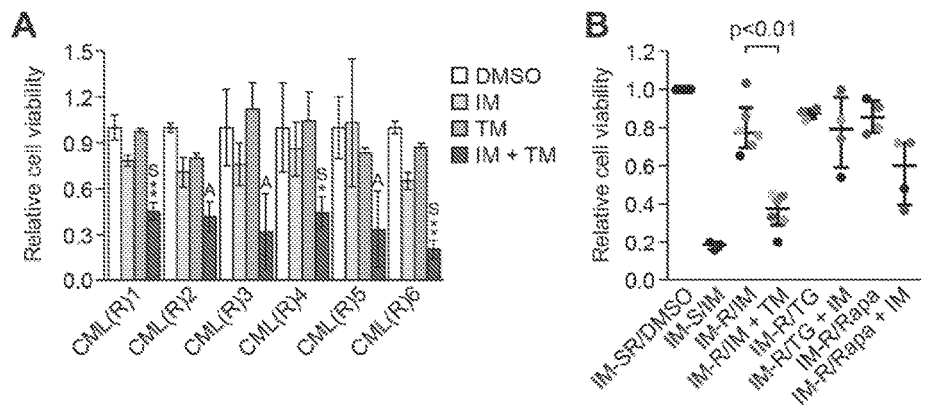
Figures 17A-B
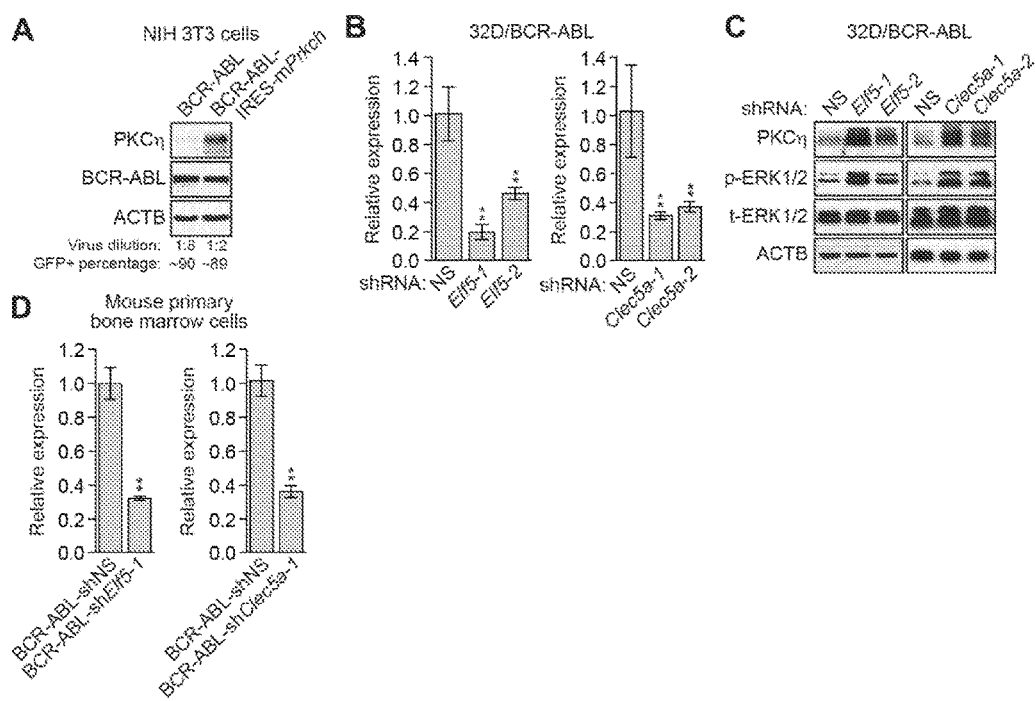
Figures 18A-D

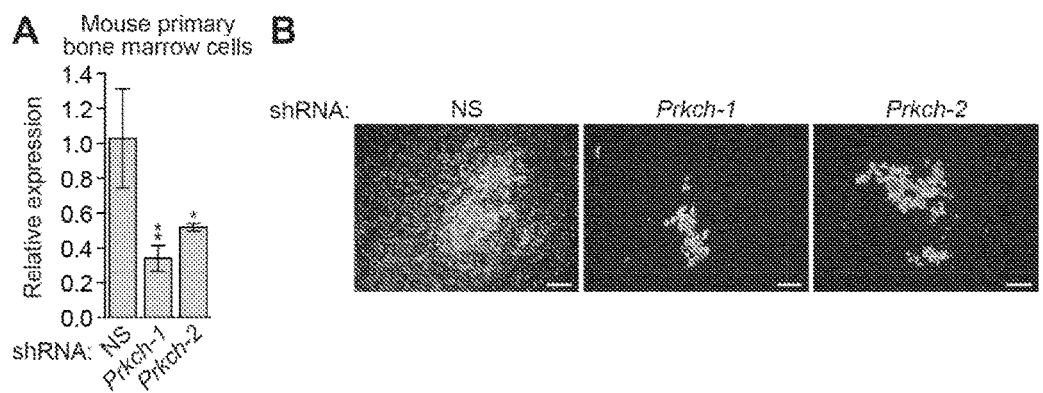
Figures 19A-B
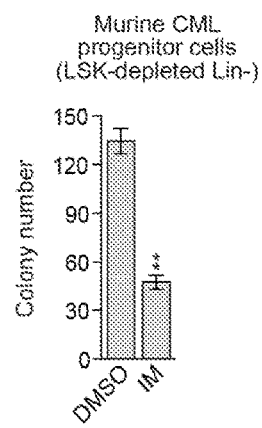
Figure 20

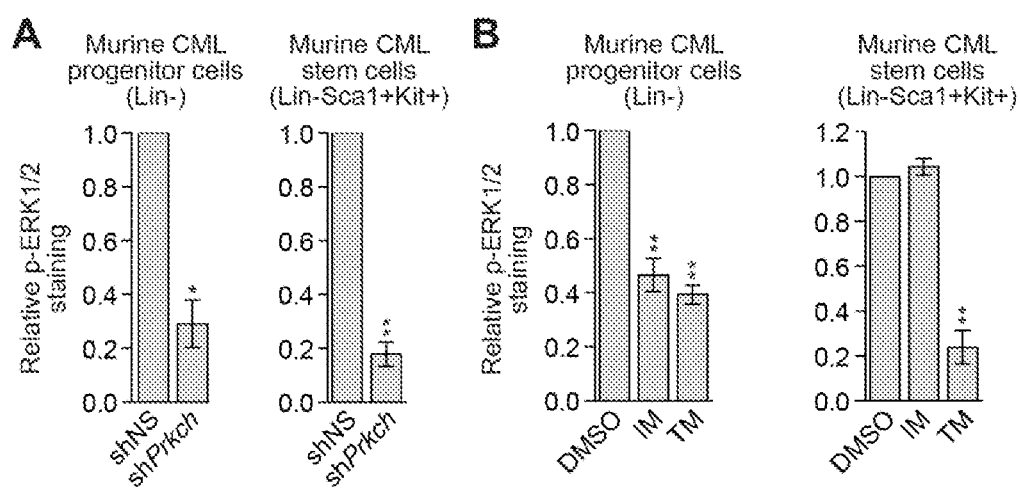
Figures 21A-B

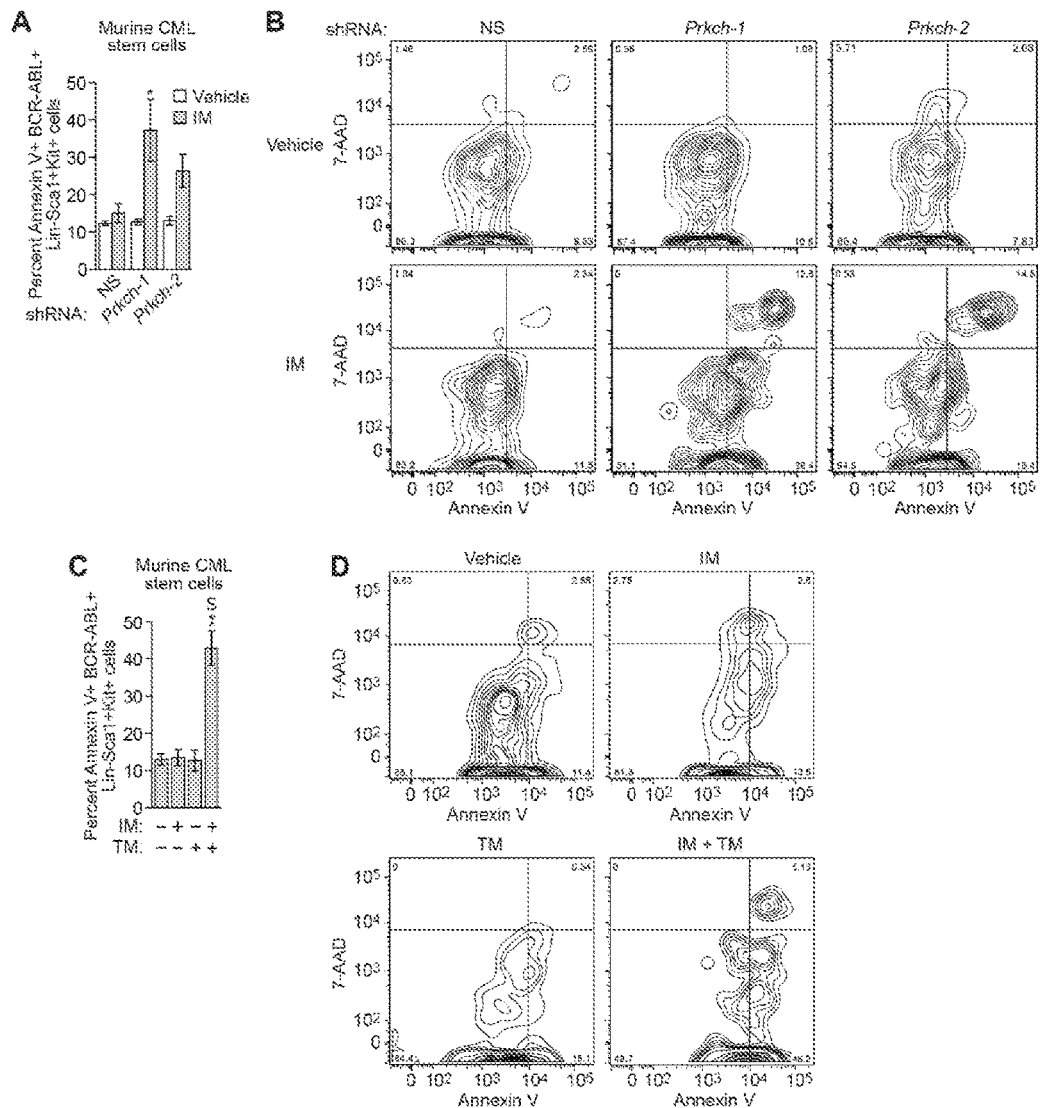
Figures 22A-D

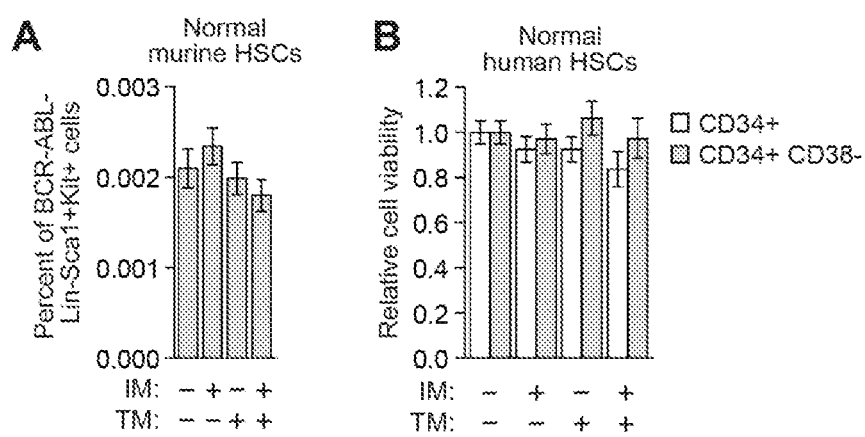
Figures 23A-B

TREATING CHRONIC MYELOGENOUS LEUKEMIA (CML)

CLAIM OF PRIORITY

This application is a U.S. National Phase Application under 35 U.S.C. § 371 of International Patent Application No. PCT/US2015/030908, filed May 14, 2015, which claims the benefit of U.S. Provisional Patent Application Ser. Nos. 61/994,689, filed on May 16, 2014, and 62/032,117, filed on Aug. 1, 2014. The entire contents of the foregoing are hereby incorporated by reference.

FEDERALLY SPONSORED RESEARCH OR DEVELOPMENT

This invention was made with Government support under Grant No. R01 CA163926 awarded by the National Institutes of Health. The Government has certain rights in the invention.

TECHNICAL FIELD

The present invention relates to methods for treating chronic myeloid leukemia (CML), e.g., BCR-ABL inhibitor imatinib mesylate (IM)-resistant CML, using combination treatments, e.g., combined treatment with a BCR-ABL inhibitor, e.g., IM, and a MEK inhibitor, e.g., trametinib.

BACKGROUND

Chronic myeloid leukemia (CML) is a hematopoietic malignancy characterized by an increase and unregulated growth of predominantly myeloid cells in the bone marrow, and their accumulation in the blood (1). A hallmark of CML is the Philadelphia chromosome resulting from a reciprocal translocation between the long arms of chromosomes 9 and 22 (2, 3). This chromosomal translocation leads to expression of BCR-ABL, an oncogenic fusion-protein with a constitutively activated ABL tyrosine kinase. BCR-ABL can transform myeloid progenitor cells and drives the development of 95% of CML cases. BCR-ABL promotes leukemogenesis by activating downstream signaling proteins that increase cell survival and proliferation (4). These pathways include, but are not limited to, the RAS/mitogen-activated protein kinase (RAF/MEK/ERK), phosphatidylinositol 3-kinase/AKT (PI3K/AKT), and JAK/STAT signaling cascades (5).

The first-line treatment for CML is imatinib mesylate (IM), which binds to the ABL kinase domain and inhibits phosphorylation of substrates (6). Although IM dramatically improves patient survival when used to treat early-stage disease, the drug is not curative. Resistance to IM can develop, especially in advanced-stage disease, leading to disease relapse and progression (7). Resistance to IM can result from multiple mechanisms that can be broadly classified as either BCR-ABL-dependent or BCR-ABL-independent (8). BCR-ABL-dependent resistance is most commonly due to the acquisition of point mutations in the ABL kinase domain that interfere with IM binding and subsequent kinase inhibition (9-11). However, in 50% or more of IM-resistant CML patients there is no mutation in BCR-ABL (12, 13) and the basis of such BCR-ABL-independent IM resistance is not understood.

SUMMARY

Previous studies have shown that a human BCR-ABL+ CML cell line, K562R, is resistant to IM due to over-expression of the Src family kinase LYN (Donato et al., Blood 101, 690-698 (2003)), however the clinical relevance of this finding is not well established. Our results reveal a previously-unknown survival pathway that promotes BCR-ABL-independent IM resistance and also contributes to the intrinsic IM resistance of CML stem cells. The mechanism described herein is therapeutically targetable and clinically relevant, which was confirmed by showing the efficacy of combined treatment with IM and trametinib both in cell culture and in IM-resistant CML mouse models.

Combined treatment with IM and trametinib represents a promising new therapeutic approach for treating CML patients with BCR-ABL-independent IM resistance. Furthermore, combined treatment with IM and trametinib synergistically kills CML stem cells with negligible effect on normal hematopoietic cells; currently, the intrinsic IM-resistance of CML stem cells is a major obstacle in long-term treatment of CML and essentially prevents a cure for the disease. Thus, the methods described herein have the potential to cure CML as opposed to the current treatment, which is effective only for the long-term management of CML.

Thus, in a first aspect, the invention provides methods for treating chronic myeloid leukemia (CML) in a mammalian subject that include administering a combination of a BCR-ABL inhibitor and a MEK inhibitor. Also provided herein is the use of a BCR-ABL inhibitor and a MEK inhibitor in the treatment of chronic myeloid leukemia (CML) in a mammalian subject.

In some embodiments, the CML is BCR-ABL inhibitor imatinib mesylate (IM)-resistant CML, e.g., BCR-ABL independent IM-resistant CML, wherein the BCR-ABL is wild-type or lacks a mutation that confers IM-resistance.

In some embodiments, the BCR-ABL inhibitor is imatinib, Nilotinib (AMN107); Dasatinib (BMS-345825); Bosutinib (SKI-606); Ponatinib (AP24534); Bafetinib (INNO-406); thiazol or a thiazol derivatives, e.g., 1,3,4 thiadiazole derivatives.

In some embodiments, the BCR-ABL inhibitor is imatinib.

In some embodiments, the MEK inhibitor is Trametinib (GSK1120212), Selumetinib, MEK162, PD-325901, cobimetinib (XL518; [3,4-Difluoro-2-(2-fluoro-4-iodoanilino)phenyl]{3-hydroxy-3-[(2S)-piperidin-2-yl]azetidin-1-yl}methanone), CL-1040, or PD035901.

In some embodiments, the MEK inhibitor is trametinib.

In some embodiments, the subject is human.

In another aspect, the invention provides methods for selecting a subject with chronic myeloid leukemia (CML) for treatment with a BCR-ABL inhibitor and a MEK inhibitor. The methods include detecting a level of PRKCH mRNA or PKCeta protein in a sample comprising leukemic cells, e.g., leukemic stem cells, from the subject; comparing the level of PRKCH mRNA or PKCeta protein in the sample to a reference level; selecting a subject who has a level of PRKCH mRNA or PKCeta protein above the reference level for treatment with a BCR-ABL inhibitor and a MEK inhibitor; and optionally administering the treatment to the selected subject.

In some embodiments, the CML is BCR-ABL inhibitor imatinib mesylate (IM)-resistant CML, e.g., BCR-ABL independent IM-resistant CML, wherein the BCR-ABL is wild-type or lacks a mutation that confers IM-resistance. In some embodiments, the methods include determining that the subject has BCR-ABL independent IM-resistant CML, e.g., determining that the BCR-ABL is wild-type or lacks a mutation that confers IM-resistance.

In some embodiments, the CML is BCR-ABL inhibitor imatinib mesylate (IM)-resistant CML.

In some embodiments, the BCR-ABL inhibitor is imatinib, Nilotinib (AMN107); Dasatinib (BMS-345825); Bosutinib (SKI-606); Ponatinib (AP24534); Bafetinib (INNO-406); thiazol or a thiazol derivatives, e.g., 1,3,4 thiadiazole derivatives.

In some embodiments, the BCR-ABL inhibitor is imatinib.

In some embodiments, the MEK inhibitor is Trametinib (GSK1120212), Selumetinib, MEK162, PD-325901, cobimetinib (XL518; [3,4-Difluoro-2-(2-fluoro-4-iodoanilino)phenyl]{3-hydroxy-3-[(2S)-piperidin-2-yl]azetidin-1-yl}methanone), CL-1040, or PD035901.

In some embodiments, the MEK inhibitor is trametinib.

In some embodiments, the level of PRKCH mRNA is determined using RNA in situ hybridization, Southern or Northern analyses, polymerase chain reaction analyses and probe arrays.

In some embodiments, the level of PKCeta protein is determined using an immunoassay.

In some embodiments, determining that the BCR-ABL is wild-type or lacks a mutation that confers IM-resistance comprises sequencing the BCR-ABL gene or a kinase domain thereof in leukemic cells of the subject, e.g., a mutation known in the art or described herein. Methods known in the art can be used to determine whether a new mutation confers IM-resistance.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and Figures, and from the claims.

DESCRIPTION OF DRAWINGS

FIG. 12. Relative IC50IM of candidate IMSG KD K562 cells. The NS control used here is the same as that used in FIG. 1E, which was derived from the same experiment. Data are represented as mean±SD (n=4).

FIGS. 13A-B. Confirmation that IMSG knockdown in K562 cells increases PRKCH and PKCη levels. (A) qRT-PCR analysis monitoring expression of PRKCH in K562 cells expressing a second shRNA targeting each IMSG, unrelated to that used in FIG. 3A. The results were normalized to that obtained with the NS control shRNA, which was set to 1. The scatter dot plot shows the median line with interquartile range. Statistical tests and exact P values are provided in table 4. (B) Immunoblot analysis showing the level of PKCη in IMSG KD K562 cells. beta-actin (ACTB) was monitored as a loading control.

FIGS. 14A-C. Demonstration that ELF5 is a direct transcriptional repressor of PRKCH. (A) Chromatin immunoprecipitation assay monitoring binding of ELF5 to the PRKCH promoter at the transcription start site (TSS) and at 500 and 1000 bp upstream of the TSS (n=3). The results were normalized to that obtained with an IgG control antibody, which was set to 1. (B and C) Expression of a luciferase reporter driven by the PRKCH promoter in K562 cells expressing a NS shRNA or one of two unrelated ELF5 shRNAs (B; n=3) or in K562 cells ectopically expressing ELF5 or, as a control, empty vector (C; n=3). Shown are firefly luciferase activities normalized to that of *Renilla luciferase*. Data are represented as mean±SD. *P≤0.05, **P≤0.01. Statistical tests and exact P values are provided in table 4.

FIGS. 15A-B. Confirmation of elevated PKCη levels in K562/PRKCH cells, and role of PRKCH in IM resistance. (A) Immunoblot analysis showing the levels of PKCη and phosphorylated and total ERK1/2 (p-ERK1/2 and t-ERK1/2, respectively) in K562 cells expressing empty vector and in two independently derived K562 clonal cell lines ectopically expressing PRKCH. (B) MTT assay measuring relative viability of representative IMSG KD K562 cell lines expressing a NS or PRKCH shRNA, and treated in the presence or absence of IM. Data are represented as mean±SD (n=4). Asterisks indicate comparisons between the two IM-treated samples. *P≤0.05, **P≤0.01. Statistical tests and exact P values are provided in table 4.

FIGS. 16A-B. Confirmation that PKCη functions through CRAF to increase RAF/MEK/ERK signaling. (A) Immunoblot analysis showing RAF/MEK/ERK activity (as measured by p- and t-MEK and p- and t-ERK1/2) in K562 cells expressing a second PRKCH shRNA unrelated to that used in FIG. 3F. The level of PKCη was monitored as a control. β-actin (ACTB) was monitored as a loading control. (B) Immunoblot analysis showing p- and t-ERK1/2 levels in K562/PRKCH-1 cells, treated in the absence or presence of IM, expressing a second ARAF, BRAF or CRAF shRNA unrelated to that used in FIG. 3G. The levels of total (t-) ARAF, BRAF and CRAF, and PKCη were monitored as controls. ACTB was monitored as a loading control.

FIGS. 17A-B. Comparison of combined treatment with IM and trametinib to IM and a JAK-STAT or PI3K inhibitor. (A) Cell viability, as measured by trypan blue cell counting, of primary leukemic cells from BCR-ABL-independent IM-resistant CML patients (n=6) treated with DMSO. 5 μM IM, 5 μM TM or a combination of the two drugs. The results were normalized to that observed with DMSO, which was set to 1. Data are represented as mean±SD. The data are the same as those shown in FIG. 4D, but plotted to show the results for each individual patient sample. Asterisks indicate comparisons between the combined drug treatment and single drug treatments. Combined drug treatment was synergistic (S) or additive (A). (B) Relative viability, as measured by trypan blue cell counting, of primary leukemic cells isolated from IM-sensitive CML patients and treated with 5 μM IM (n=3), or isolated from BCR-ABL-independent IM-resistant CML patients and treated with 5 μM IM, 5 μM TM or a combination (n=6), or treated with 0.5 μM TG101348 (TG, a JAK-STAT inhibitor) or 10 nM rapamycin (Rapa, a PI3K inhibitor) alone or in combination with 5 μM IM (n=4). The results were normalized to those obtained by DMSO treatment of the same samples, which was set to 1. Error bars indicate median with interquartile range. Matched samples from the same patient are indicated by dots of the same color. Samples IM-SR/DMSO, IM-S/IM, IM-R/IM and IM-R/IM+TM are the same as those in FIG. 4D and are shown to facilitate comparison. The results presented here and in FIG. 4D were derived from a single experiment. For statistical significance, only comparisons between double treatments and IM alone were made. Statistical tests and exact P values are provided in table 4.

FIGS. 18A-D. Effectiveness of retroviruses co-expressing BCR-ABL and either PRKCH or an Elf5 or Clec5a shRNA. (A) Immunoblot analysis monitoring levels of PKCη and BCR-ABL in NIH 3T3 cells transduced with a retrovirus expressing BCR-ABL or one co-expressing BCR-ABL and murine Prkch. The percentage of GFP+ cells obtained was similar using both retroviruses, demonstrating equivalent virus titers. The same virus titers were used for transduction of primary mouse bone marrow cells. (B) qRT-PCR analysis monitoring knockdown efficiencies in 32D/BCR-ABL cells of one of two unrelated Elf5 (left) or Clec5a (right) shRNAs. Data are represented as mean±SD (n=3). *P≤0.05, **P≤0.01. (C) Immunoblot analysis monitoring levels of PKCη and phosphorylated and total ERK1/2 (p-ERK1/2 and t-ERK1/2, respectively) in 32D/BCR-ABL cells expressing an NS, Elf5 or Clec5a shRNA. (D) qRT-PCR analysis monitoring knockdown efficiencies of Elf5 (left) and Clec5a (right) in mouse primary bone marrow cells transduced with a retrovirus co-expressing BCR-ABL and either an Elf5 or Clec5a shRNA. The most effective Elf5 shRNA (Elf5-1) and Clec5a shRNA (Clec5a-1), as determined by the results in (B), were used here and in FIGS. 4 F and H. Data are represented as mean±SD (n=3). *P≤0.05, **P≤0.01. Statistical tests and exact P values are provided in table 4.

FIGS. 19A-B. Knockdown of PRKCH in BCR-ABL+ cells decreases colony formation. (A) qRT-PCR analysis monitoring knockdown efficiency of Prkch in mouse primary bone marrow cells expressing one of two unrelated Prkch shRNAs. The results were normalized to that obtained with a NS control, which was set to 1. Data are represented as mean±SD (n=3). *P≤0.05, **P≤0.01. Statistical tests and exact P values are provided in table 4. (B) Micrograph showing typical colonies of BCR-ABL+ mouse primary bone marrow cells expressing a NS shRNA or one of two unrelated Prkch shRNAs. Scale bar, 100 µm.

FIG. 20. Confirmation of IM sensitivity of murine CML progenitor cells. Colony formation assay monitoring survival of BCR-ABL+ murine progenitor cells (Lin–Sca1+Kit+-depleted Lin– cells) expressing a NS shRNA and treated with DMSO or 0.1 µM IM (n=3). Data are represented as mean±SD. As a comparison, see FIG. 7C, which shows the results of a similar analysis of IM-resistant murine CML stem cells. *P≤0.05, **P≤0.01. Statistical tests and exact P values are provided in table 4.

FIGS. 21A-B. Analysis of phosphorylated-ERK1/2 levels in CML progenitor and stem cells. (A) Intracellular phosphorylated ERK1/2 levels in Lin– and Lin–Sca1+Kit+ BCR-ABL+ Prkch KD or control bone marrow cells (n=3). The results were background corrected and then normalized to that obtained with the NS control shRNA, which was set to 1. Data are represented as mean±SEM. (B) Intracellular phosphorylated-ERK1/2 levels in Lin– and Lin–Sca1+Kit+ BCR-ABL+ bone marrow cells treated with DMSO, IM or trametinib. (n=4). The results were background corrected and then normalized to that obtained with DMSO, which was set to 1. Data are represented as mean±SEM. *P≤0.05, **P≤0.01. Statistical tests and exact P values are provided in table 4. These results accompany the representative experiment shown in FIGS. 7, A and B.

FIGS. 22A-D. Synergistic induction of apoptosis in murine CML stem cells by IM and trametinib. (A) Apoptosis assay. CML mice (n=5) were orally gavaged with vehicle or IM. BCR-ABL+ bone marrow cells were stained with a Lin/Sca1/Kit antibody cocktail, then with Annexin V and 7-AAD followed by FACS. Data are represented as mean±SEM. (B) FACS analysis showing representative Annexin V/7-AAD staining of murine CML stem cells expressing a NS shRNA or one of two unrelated Prkch shRNAs isolated from mice treated with vehicle or IM. These data provided the basis for the bar graph in (A). (C) Apoptosis assay. Mice were orally gavaged with vehicle (n=6), IM (n=6), TM (n=5) or both (n=5). BCR-ABL+ bone marrow cells were stained as described in (A). Data are represented as mean±SEM. (D) FACS analysis showing representative Annexin V/7-AAD staining of murine CML stem cells isolated from mice treated with vehicle, IM, TM or a combination of IM and TM. These data provided the basis for the bar graph in (C). *P≤0.05, **P≤0.01. Statistical tests and exact P values are provided in table 4.

FIGS. 23A-B. Effect of IM and trametinib on normal hematopoietic stem cells. (A) FACS determination of the percentage of normal (BCR-ABL-) murine Lin–Sca1+Kit+ bone marrow cells after treatment with vehicle (n=21), IM (n=21), TM (n=9) or both IM and TM (n=9). Data are represented as mean±SEM. (B) Relative viability, as measured by trypan blue cell counting, of normal human hematopoietic CD34+ cells and hematopoietic stem cells (CD34+CD38–) treated with DMSO, IM, TM or a combination of drugs (n=4). The results were normalized to that obtained in cells treated with DMSO, which was set to 1. Data are represented as mean±SD. *P≤0.05, **P≤0.01. Statistical tests and exact P values are provided in table 4.

DETAILED DESCRIPTION

CML, like several other malignancies, is propagated by a small population of stem cells, elimination of which is likely required to achieve long-term remission and cure (14, 15). An important limitation of IM treatment is that although IM inhibits BCR-ABL activity in CML stem cells, these cells do not depend on BCR-ABL activity for survival and are thus not eliminated (16, 17). These findings imply that CML stem cells use survival signals other than BCR-ABL to maintain viability in the presence of IM. Understanding the mechanism by which CML stem cells are intrinsically resistant to IM is essential for devising strategies to eradicate residual leukemia. To gain insight into how IM resistance can occur in the absence of BCR-ABL mutations, an RNA interference (RNAi) screen was performed to identify genes that regulate IM responsiveness. Our results reveal a survival pathway that promotes BCR-ABL-independent IM resistance and also contributes to the IM resistance of CML stem cells.

Figure 8:
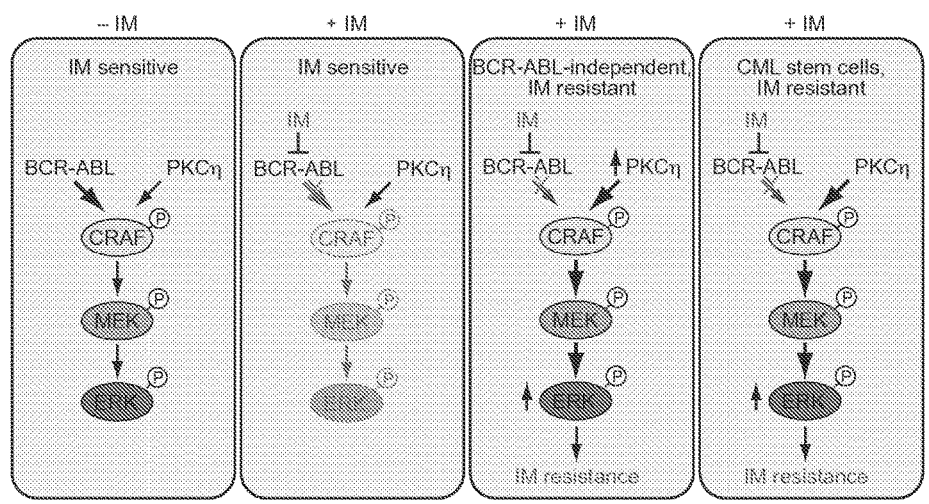
FIG. 8. Elevated PKCη levels lead to IM resistance in CML and CML stem cells. Relative contributions of BCR-ABL and PKCη to RAF/MEK/ERK signaling are indicated by arrow size and shading.

Without wishing to be bound by theory, the present inventors have identified a molecular pathway whose increased activity promotes BCR-ABL-independent IM resistance and also contributes to the IM resistance of CML stem cells. See, e.g., the schematic model in FIG. 8 and below. In typical IM-sensitive CML cells, BCR-ABL is the major contributor to RAF/MEK/ERK signaling. Thus, treatment with IM substantially reduces RAF/MEK/ERK signaling, leading to inhibition of proliferation and induction of apoptosis. In BCR-ABL-independent, IM resistant CML cells, elevated levels of Protein Kinase C eta (PKCη), due to decreased expression of one or more IM-sensitizing genes (IMSGs), results in phosphorylation and activation of CRAF, thereby augmenting RAF/MEK/ERK signaling. Following treatment with IM, RAF/MEK/ERK signaling is sustained, resulting in drug resistance.

A previous study analyzing IM resistance resulting from mutations in BCR-ABL found that IM treatment "paradoxically" increased RAF/MEF/ERK signaling through a RAS-directed pathway (Konuma et al. Exp Hematol 39, 697-709 e695 (2011)). Although the IM-resistance mechanism we describe, like that in Packer et al. (Cancer Cell 20, 715-727 (2011)), involves increased RAF/MEK/ERK signaling, there are several important differences. For example, in the experiments described herein the increased RAF/MEK/ERK signaling was not dependent upon RAS but rather initiated by PKCη, was constitutive and not induced by IM, and, as discussed below, was also relevant to the intrinsic IM resistance of CML stem cells. In addition, several reports have described experimentally derived BCR-ABL-independent IM-resistant CML cell lines in which RAF/MEK/ERK signaling is increased by a mechanism that was not determined (Aceves-Luquero et al., PLoS One 4, e6124 (2009); Hentschel et al., Int J Oncol 39, 585-591 (2011); Nambu et al., Cancer Sci 101, 137-142 (2010).) or have provided other evidence that RAF/MEK/ERK signaling can contribute to IM resistance (Chang et al., Blood 110, 994-1003 (2007); Chu et al., Blood 103, 3167-3174 (2004); Mizuchi et al., Biochem Biophys Res Commun 326, 645-651 (2005); Pellicano et al., Leukemia 25, 1159-1167 (2011)).

The mechanistic basis by which IMSGs regulate PRKCH expression is largely unknown. One of the IMSGs identified, ELF5, is directly bound at the transcription start-site of PRKCH, and can decrease PRKCH expression. Thus, ELF5 is a direct transcriptional repressor of PRKCH, explaining why decreased ELF5 levels result in increased PRKCH expression. Whether other IMSGs function directly or indirectly to regulate PRKCH expression remained to be determined.

It is possible that the RNAi screen described herein, like other large-scale RNAi screens (Mullenders and Bernards, Oncogene 28, 4409-4420 (2009)), was not saturating and thus there may be other IMSGs, and regulators of PRKCH expression, that remain to be identified. The present results suggest that a variety of diverse perturbations can increase PRKCH expression. A previous expression profiling study revealed that the level of PRKCH in CML cells increased following one week of IM treatment (Bruennert et al., Leukemia 23, 983-985 (2009)), perhaps due to selection of and enrichment for cells with high PRKCH expression. This finding may also be explained by induction of PRKCH expression by IM treatment, although we found in IMSG KD K562 cell lines and CML stem cells that PRKCH is highly expressed in the absence of IM. In addition to its role in IM resistance, elevated Prkch expression also accelerates disease progression in a mouse model of CML. Consistent with this idea, in a previous expression profiling study, PRKCH levels were found to increase during disease progression in CML patients. In the same study, the expression levels of seven of nine IMSGs analyzed decreased during disease progression (Radich et al., Proc Nat Acad Sci USA 103, 2794-2799 (2006)).

The IM-resistance mechanism described herein is therapeutically targetable, which was demonstrated by the showing that combined treatment with IM and the FDA-approved MEK inhibitor trametinib synergistically kills BCR-ABL+ IMSG KD cells and prolongs survival in several mouse models of BCR-ABL-independent IM-resistant CML. These results are also relevant to another current challenge of CML treatment: the intrinsic resistance of CML stem cells to IM. Both human and murine CML stem cells contain high levels of PRKCH and provide evidence that this is responsible, at least in part, for their IM resistance. The high PRKCH levels in CML stem cells promotes RAF/MEK/ERK signaling, which helps explain why CML stem cells are not dependent upon BCR-ABL for survival (16, 17). Collectively, these results provide a rationale for our finding that CML stem cells, but not normal hematopoietic stem cells, are efficiently killed by combined treatment with IM and trametinib, and suggest a therapeutic strategy for their eradication.

Chronic Myelogenous Leukemia (CML)

CML is a clonal stem cell disorder that is typically associated with the presence in more than 95% of patients of leukemic cells that have the Philadelphia chromosome (Ph1) (see, e.g., Kurzrock et al., Ann Intern Med 138 (10): 819-30, 2003; Goldman and Melo, N Engl J Med 349 (15): 1451-64, 2003), a reciprocal translocation between chromosomes 9 and 22. The Ph1 translocation results in the transfer of the Abelson (ABL) oncogene from chromosome 9 to the breakpoint cluster region (BCR) of chromosome 22, creating a fused BCR/ABL gene that codes for an abnormal, constitutively active tyrosine kinase that is essential to the growth and survival of leukemic cells. The Ph1 can be detected in bone marrow aspirate or peripheral blood samples using known methods, including cytogenetic studies, Southern blot analysis, Fluorescent in situ hybridization, or RT-PCR. See also the National Cancer Institute: PDQ® Chronic Myelogenous Leukemia Treatment. Bethesda, Md.: National Cancer Institute. Date last modified Mar. 28, 2014. Available at: http://www.cancer.gov/cancertopics/pdq/treatment/CML/HealthProfessional. Accessed May 6, 2014.

Bone marrow sampling is often done to assess cellularity, fibrosis, and cytogenetics. CML is typically staged into three phases: chronic, accelerated, and blastic phases based on myoblasts counts. Chronic-phase CML is characterized by less than 10% blasts and promyelocytes in the peripheral blood and bone marrow. Accelerated-phase CML is characterized by 10% to 19% blasts in either the peripheral blood or bone marrow. Blastic-phase CML is characterized by 20% or more blasts in the peripheral blood or bone marrow. When 20% or more blasts are present along with fever, malaise, and progressive splenomegaly, the patient has entered blast crisis (Cortes J E, et al., Cancer 106 (6): 1306-15, 2006).

IM-Resistant CML

Although imatinib is successful in treating many patients, development of resistance against imatinib is common (Valenti, Biologics. 1(4): 433-448, 2007). As noted above, resistance may be the result of one or several mechanisms, including molecular resistance caused by mutation of the BCR/ABL gene, or BCR/ABL independent resistance, e.g., associated with stem cell-specific survival factors, e.g., associated with increased RAF/MEK/ERK signaling that is not dependent upon RAS but rather initiated by PKCη. Patients with CML are considered to be imatinib-resistant when response is lost or is not seen with a daily dose of >400 mg imatinib (Valenti, 2007; Kantarjian et al., Blood. 101 (2):473, 2003; Baccarani et al., Blood. 108(6):1809-20, 2006).

Methods of Treating CML

Described herein are methods for treating CML, e.g., treating or reducing the risk of developing IM-resistant CML, that include the use of a combination of at least one BCR/ABL inhibitor and at least one MEK inhibitor.

Subject Selection

The methods described herein are useful in the treatment of subjects with CML, e.g., IM-resistant CML, e.g., in which the IM-resistant subject lacks a mutation in BCR-ABL that confers drug-resistance (i.e., BCR-ABL independent IM-resistance).

Any method known in the art can be used to diagnose CML in a subject, including detecting the presence of the Ph1 translocation in leukemic cells of the subject, e.g., as described above. Other methods can also be used.

As described herein, CML stem cells have elevated levels of PRKCH expression and PKCη protein. Thus in some embodiments the methods can include detecting levels of PRKCH mRNA, or PKCη protein or activity, in leukemic cells, e.g., stem cells of the subject. Routine methods can be used to detect expression levels. A nucleic acid sequence of human PRKCH cDNA is in GenBank at accession no. NM_006255.3; the sequence of human PKCη protein is at accession no. NP_006246.2. For example, antibodies (including antibodies that bind specifically to the phosphorylated form) are commercially available from Abcam, Cell Sciences, Life Technologies, MBL International, Novus Biologicals, Bethyl Laboratories, and Santa Cruz Biotechnology, Inc. The presence and/or level of a protein can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289 (5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of PKCη.

The presence and/or level of mRNA in a sample can also be evaluated using methods known in the art, e.g., both by in situ and/or by in vitro formats. For example, isolated mRNA can be used in hybridization or amplification assays that include, but are not limited to, RNA in situ hybridization (RNA ISH, e.g., a branched DNA assay), Southern or Northern analyses, polymerase chain reaction analyses and probe arrays. One method for the detection of mRNA levels involves contacting the isolated mRNA with a nucleic acid molecule (probe) that can hybridize to the mRNA encoded by the PRKCH gene being detected. The nucleic acid probe can be, for example, a full-length PRKCH nucleic acid, such as the cDNA deposited with ATCC as Accession Number NM_006255.3, or a portion thereof, such as an oligonucleotide of at least 7, 15, 30, 50, 100, 250 or 500 nucleotides in length and sufficient to specifically hybridize under stringent conditions to PRKCH mRNA or genomic DNA. Other suitable probes for use in the assays are described herein. Alternatively, levels or presence of PRKCH mRNA can be detected with nucleic acid amplification, e.g., by rtPCR (Mullis (1987) U.S. Pat. No. 4,683,202), ligase chain reaction (Barany (1991) Proc. Natl. Acad. Sci. USA 88:189-193), self-sustained sequence replication (Guatelli et al., (1990) Proc. Natl. Acad. Sci. USA 87:1874-1878), transcriptional amplification system (Kwoh et al., (1989), Proc. Natl. Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. The level of PRKCH mRNA, or PKCeta protein, can then be compared to a reference level, and a subject who has a level at or above the reference level, or above the reference level, can be selected for treatment using the methods described herein.

Suitable reference values can be determined using methods known in the art, e.g., using standard clinical trial methodology and statistical analysis. The reference values can have any relevant form. In some cases, the reference comprises a predetermined value for a meaningful level of PRKCH, e.g., a control reference level that represents a normal level of PRKCH, e.g., a level in an unaffected subject or a subject who is not at risk of developing CML, and/or a disease reference that represents a level of the proteins associated with CML.

Figure 1:
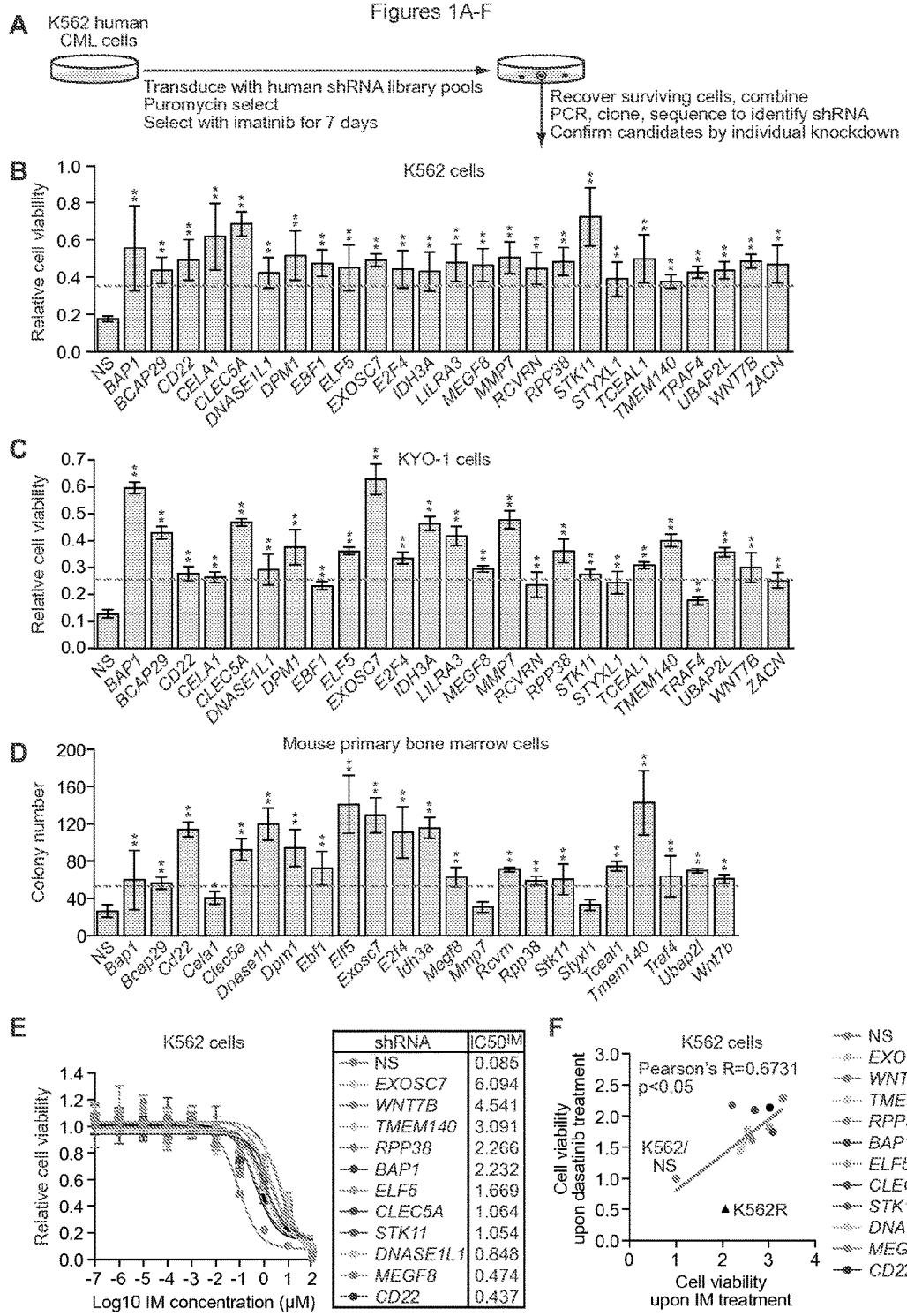
FIGS. 1A-F. A large-scale shRNA screen identifies IMSGs. (A) Schematic summary of the screen. (B) Relative viability of IMSG KD K562 cells in the presence of IM, as measured by MTT assay (n=4). The results were normalized to that obtained with DMSO-treated cells, which was set to 1. IMSG shRNAs that conferred >2-fold increase in cell survival (indicated by the red line) relative to the NS control shRNA were considered positive. (C) Relative viability of IMSG KD KYO-1 cells in the presence of IM, as measured by MTT assay (n=4). The results were normalized and positives determined as described in (B). (D) Colony formation assay monitoring survival of BCR-ABL+ mouse primary bone marrow cells expressing an IMSG shRNA in the presence of IM (n=3). IMSG shRNAs that conferred >2-fold increase in colony number (indicated by the red line) relative to the NS control shRNA were considered positive. (E) Relative IC50$^{TM}$ of IMSG KD K562 cells (n=4). (F) Cell viability, as measured by MTT assay, of IMSG KD K562 cells treated with 500 nM dasatinib or 10 µM IM for 3 days (n=4). K562 cells expressing an NS shRNA (K562/NS) and IM-resistant K562 cells (K562R) were analyzed as controls. Data are represented as mean±SD. *P≤0.05, **P≤0.01. Statistical tests and exact P values are provided in table 4.

In some embodiments, the subject has imatinib-resistant CML, and the methods are used to treat the IM-resistant CML in the subject. In some embodiments, the subject has CML but has not yet developed imatinib resistance, and the methods are used to treat CML in the subject or to prevent or reduce the risk of development of IM-resistant CML in the subject. In some embodiments, the subject has BCR-ABL independent IM-resistance, i.e., is IM-resistant but has no mutations in the BCR-ABL kinase domain that would confer drug-resistance (i.e., no mutations in the region of the sequence at GenBank Acc No. NM_005157.4 that encodes amino acids 235 to 497 of GenBank NP_005148.2, shown underlined below, that would confer resistance). More than 90 BCR-ABL point mutations have been identified, including mutations in the P-loop, the C-helix, SH2 domain, substrate binding site, activation loop and C-terminal lobe M237I; M244V; L248V; G250A; G250E; G250V; Q252H; Y253F; Y253H; E255D; E255K; E255R; E255V; E275K; D276G; E281K; E285N; E292K; F311V; T315I; F317C; F317L; F317V; G321E; D325N; S348L; M351T; Y353H; E355A; E355G; E355K; F359C; F359V; E373G; V379I; A380S; L387A; M388H; H396P; H396R; see Bixby and Talpaz, Hematology: 461-476 (2009); Soverini et al., Clin Cancer Res 12: 7374-7379 (2006); also FIG. 1 of Soverini et al., Blood, 118:1208-1215 (2011). Nine of these mutations account for more than 85% of all mutations: M244V, G250E, Y253F/H, E255K/V, T315I, M351T, and F359V. The T315I mutation (shown in bold and upper case below) is the most clinically relevant.

Reference sequence of human bcr/abl gene product; the kinase domain is underlined. From GenBank Acc No. NM_005157.4

```
                                                            (SEQ ID NO: 1)
      1    mleiclklvg ckskkglsss sscyleealq rpvasdfepq glseaarwns kenllagpse 61    ndpnlfvaly dfvasgdntl sitkgeklry lgynhngewc eaqtkngqgw vpsnyitpvn 121    slekhswyhg pvsrnaaeyl lssgingsfl vresesspgq rsislryegr vyhyrintas 181    dgklyvsses rfntlaelvh hhstvadgli ttlhypapkr nkptvygvsp nydkwemert 241    ditmkhklgg gqygevyegv wkkysltvav ktlkedtmev eeflkeaavm keikhpnlvq 301    llqvctrepp fyiiTefmty qnlldylrec nrqevnavvl lymatqissa meylekknfi 361    hrdlaarncl vqenhlvkva dfqlsrlmtq dtytahaqak fpikwtapes laynkfsiks 421    dvwafgvllw eiatyqmspy pqidlsqvye llekdyrmer peqcpekvye lmracwqwnp 481    sdrpsfaeih qafetmfqes sisdevekel gkqgvrgays tllqapelpt ktrtsrraae 541    hrdttdvpem phskgqgesd pldhepaysp llprkergpp egglnederl lpkdkktnlf 601    salikkkkkt aptppkrsss fremdgqper rgageeegrd isngalaftp ldtadpaksp 661    kpsngagvpn galresggsg frsphlwkks stltssrlat geeegggsss krflrscsas 721    cvphgakdte wrsvtlprdl qstgrqfdss tfgghksekp alprkragen rsdqvtrgtv 781    tppprlvkkn eeaadevfkd imesspgssp pnitpkplrr qvtvapasgl phkeeaekgs 841    algtpaaaep vtptskagsg apggtskgpa eesrvrrhkh ssespgrdkg klsrlkpapp 901    pppaasagka ggkpsqspsq eaageavlga ktkatslvda vnsdaakpsq pgeglkkpvl
```

```
-continued
 961    patpkpqsak psgtpispap vpstlpsass alagdqpsst afiplistry slrktrqppe 1021    riasgaitkg vvldstealc laisrnseqm ashsavleag knlytfcvsy vdsiqqmrnk 1081    fafreainkl ennlrelqic patagsgpaa tqdfskllss vkeisdivqr
```

Methods for identifying mutations in subjects with CML are also known in the art, and include direct sequencing, optionally combined with nested PCR and/or denaturing-high performance liquid chromatography (D-HPLC) analysis; allele-specific PCR (e.g., fluorescent allele-specific PCR); pyrosequencing; high resolution melting; double gradient denaturing electrophoresis; MALDT-TOF mass spectrometry; nanofluidic array (Oehler et al., Leukemia 2008); fluorescence PCR and PNA clamping; fluorescence polarization template-directed dye-terminator incorporation (FP-TDI); and microarray analysis. Other methods of nucleic acid analysis can include direct manual sequencing (Church and Gilbert, *Proc. Natl. Acad. Sci. USA* 81:1991-1995 (1988); Sanger et al., *Proc. Natl. Acad. Sci. USA* 74:5463-5467 (1977); Beavis et al., U.S. Pat. No. 5,288,644); automated fluorescent sequencing; single-stranded conformation polymorphism assays (SSCP) (Schafer et al., *Nat. Biotechnol.* 15:33-39 (1995)); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., *Proc. Natl. Acad. Sci. USA* 86:232-236 (1989)); denaturing high performance liquid chromatography (DHPLC, Underhill et al., *Genome Res.* 7:996-1005 (1997)); infrared matrix-assisted laser desorption/ionization (IR-MALDI) mass spectrometry (WO 99/57318); mobility shift analysis (Orita et al., *Proc. Natl. Acad. Sci. USA* 86:2766-2770 (1989)); restriction enzyme analysis (Flavell et al., *Cell* 15:25 (1978); Geever et al., *Proc. Natl. Acad. Sci. USA* 78:5081 (1981)); quantitative real-time PCR (Raca et al., *Genet Test* 8(4):387-94 (2004)); heteroduplex analysis; chemical mismatch cleavage (CMC) (Cotton et al., *Proc. Natl. Acad. Sci. USA* 85:4397-4401 (1985)); RNase protection assays (Myers et al., *Science* 230:1242 (1985)); use of polypeptides that recognize nucleotide mismatches, e.g., *E. coli* mutS protein; and combinations of such methods. See, e.g., Gerber et al., U.S. Patent Publication No. 2004/0014095 which is incorporated herein by reference in its entirety. Other methods can also be used.

Although the methods described herein refer to treatment of CML, the methods can also be used to treat other IM-resistant BCR-ABL+ leukemia, e.g., Ph+ Acute Lymphoblastic Leukemia (~20% in adult, 5% in children), Ph+ Acute Myelogenous Leukemia (~2%), and potentially KIT+ gastrointestinal stromal tumors (GIST, as Imatinib can also inhibit KIT kinase) as well.

BCR-ABL Inhibitors

A number of BCR/ABL inhibitors are known in the art. For example, imatinib (GLEEVEC) has been successfully used in the treatment of CML. Additional BCR/ABL inhibitors include Nilotinib (AMN107); Dasatinib (BMS-345825); Bosutinib (SKI-606); Ponatinib (AP24534); Bafetinib (INNO-406); and thiazol and thiazol derivatives, e.g., 1,3,4 thiadiazole derivatives.

MEK Inhibitors

A number of MEK inhibitors (which specifically inhibit mitogen-activated protein kinase kinase enzymes MEK1 and/or MEK2) are known in the art. For example, Trametinib (GSK1120212) has been used for the treatment of certain cancers. Other examples of MEK inhibitors include Selumetinib, MEK162, PD-325901, cobimetinib (XL518; [3,4-Difluoro-2-(2-fluoro-4-iodoanilino)phenyl]{3-hydroxy-3-[(2S)-piperidin-2-yl]azetidin-1-yl} methanone), CL-1040, and PD035901.

Pharmaceutical Compositions

The methods described herein include the manufacture and use of pharmaceutical compositions, which include a BCR-ABL inhibitor, e.g., IM, and a MEK inhibitor, e.g., trametinib as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811. The pharmaceutical compositions can be included in a container, pack, or dispenser together with instructions for administration.

Dosing

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Alternatively, doses approved by the FDA can be used, e.g., for trametinib, 1-2 mg orally once a day, and up to a maximum of 800 mg/day of imatinib.

EXAMPLES

The invention is further described in the following examples, which do not limit the scope of the invention described in the claims.

Materials and Methods

The following materials and methods were used in the Examples set forth herein.

Study Design

The overall study objective was to identify mechanisms underlying BCR-ABL-independent IM-resistance in CML and CML stem cells. The study used cultured human CML cell lines, BCR-ABL+ mouse primary bone marrow cells, mouse models of BCR-ABL-independent IM-resistant CML, and bone marrow or blood samples from CML patients. The study consisted of a series of controlled laboratory experiments and measured multiple parameters including gene expression, cell viability, apoptosis, cell signaling pathway activity, and leukemic progression as described below. For animal experiments, mice were randomly allocated to each group for drug treatment after bone marrow transplantation, and were subsequently analyzed in a non-blinded fashion. Animal sample sizes were selected based on precedent established by previous publications and an understanding that at least n=5 is generally required to achieve statistical significance. Human CML samples were selected on the basis of sample availability and a requirement to achieve statistical significance. For mouse experiments involving shRNAs, the most efficacious shRNA of multiple shRNAs tested and validated in cell culture was used, a criterion that was established prospectively. All quantitative data were collected from experiments performed in at least triplicate.

Clone IDs for individual shRNAs used in this study are listed in table 5 and primer sequences used for qRT-PCR analysis are listed in table 6.

TABLE 5

List of clone IDs for shRNAs obtained from Open Biosystems/Thermo Scientific.

| Human Gene | First shRNA | Second shRNA |
| --- | --- | --- |
| ABCB6 | TRCN0000060318 | |
| ADARB2 | TRCN0000051893 | |
| AIFM3 | TRCN0000064545 | |
| AKR1C1 | TRCN0000036544 | |
| AKR1C3 | TRCN0000026540 | |
| ANO2 | TRCN0000138764 | |
| ARAF | TRCN0000000571 | TRCN0000000568 |
| ASAH3L | TRCN0000050685 | |
| BAP1 | TRCN0000007373 | TRCN0000007372 |
| BAZ2A | TRCN0000015571 | |
| BCAP29 | TRCN0000060447 | TRCN0000060444 |
| BMI1 | TRCN0000020158 | |
| BMP6 | TRCN0000058615 | |
| BRAF | TRCN0000006291 | TRCN0000006292 |
| C6orf224 | TRCN0000140490 | |
| CCL14 | TRCN0000057850 | |
| CD22 | TRCN0000057623 | TRCN0000057625 |
| CELA1 | TRCN0000003679 | TRCN0000003681 |
| CHRNA1 | TRCN0000060992 | |
| CLEC5A | TRCN0000054035 | TRCN0000054034 |
| CMYA5 | TRCN0000129695 | |
| CRAF | TRCN0000001067 | TRCN0000001068 |
| CUBN | TRCN0000055649 | |
| CYP46A1 | TRCN0000063810 | |

TABLE 5-continued

List of clone IDs for shRNAs obtained from Open Biosystems/Thermo Scientific.

| Human Gene | First shRNA | Second shRNA |
| --- | --- | --- |
| DGKD | TRCN0000000672 | |
| DNASE1L1 | TRCN0000049688 | TRCN0000049690 |
| DPM1 | TRCN0000036188 | TRCN0000036186 |
| DUSP13 | TRCN0000003064 | |
| EBF1 | TRCN0000013828 | TRCN0000013830 |
| EFEMP2 | TRCN0000053336 | |
| EFNA3 | TRCN0000058722 | |
| EHD2 | TRCN0000053473 | |
| ELF5 | TRCN0000013875 | TRCN0000013877 |
| EXOSC7 | TRCN0000051072 | TRCN0000051070 |
| E2F4 | TRCN0000013809 | TRCN0000013810 |
| FAHD1 | TRCN0000050068 | |
| FAM92A1 | TRCN0000136349 | |
| GDAP1L1 | TRCN0000136540 | |
| GFRA2 | TRCN0000060710 | |
| GHRH | TRCN0000083152 | |
| GRK5 | TRCN0000000842 | |
| GTF3C4 | TRCN0000013402 | |
| IDH3A | TRCN0000027270 | TRCN0000027310 |
| IDS | TRCN0000051546 | |
| IFT140 | TRCN0000147721 | |
| IL1A | TRCN0000059211 | |
| ITCH | TRCN0000002087 | |
| KCNC4 | TRCN0000044942 | |
| KCNH3 | TRCN0000044593 | |
| KIR2DL2 | TRCN0000061458 | |
| LEP | TRCN0000058353 | |
| LGALS9 | TRCN0000057446 | |
| LILRA3 | TRCN0000056945 | TRCN0000056946 |
| LMO7 | TRCN0000006490 | |
| LRAT | TRCN0000035998 | |
| MED8 | TRCN0000052951 | |
| MEGF8 | TRCN0000055555 | TRCN0000055554 |
| MEP1A | TRCN0000050903 | |
| MMP7 | TRCN0000051847 | TRCN0000051844 |
| MOV10 | TRCN0000049978 | |
| NCBP1 | TRCN0000059506 | |
| OBFC2A | TRCN0000134695 | |
| OR2D2 | TRCN0000060969 | |
| PAG1 | TRCN0000123270 | |
| POLR1C | TRCN0000052904 | |
| PRKCH | TRCN0000006296 | TRCN0000006295 |
| PRSS1 | TRCN0000052119 | |
| PSMD10 | TRCN0000058074 | |
| RASL10B | TRCN0000047610 | |
| RCVRN | TRCN0000053264 | TRCN0000053263 |
| RFK | TRCN0000037600 | |
| RIN2 | TRCN0000062647 | |
| RPP38 | TRCN0000049875 | TRCN0000049876 |
| RPS6KB1 | TRCN0000003162 | |
| SEC23IP | TRCN0000064955 | |
| SGK493 | TRCN0000037531 | |
| SH3TC1 | TRCN0000062611 | |
| SOX18 | TRCN0000017449 | |
| STK11 | TRCN0000000408 | TRCN0000000409 |
| STYXL1 | TRCN0000003054 | TRCN0000003052 |
| TCEAL1 | TRCN0000013415 | TRCN0000013413 |
| TM4SF18 | TRCN0000122444 | |
| TMEM140 | TRCN0000138719 | TRCN0000138320 |
| TRAF4 | TRCN0000034239 | TRCN0000034241 |
| TRIM24 | TRCN0000021262 | |
| UBAP2L | TRCN0000007681 | TRCN0000007679 |
| WDR45L | TRCN0000148944 | |
| WDR92 | TRCN0000053730 | |
| WNT7B | TRCN0000061877 | TRCN0000061875 |
| ZACN | TRCN0000060205 | TRCN0000060204 |
| ZFP82 | TRCN0000016086 | |
| ZHX1 | TRCN0000020354 | |
| ZKSCAN3 | TRCN0000017750 | |
| Mouse Gene | | |
| Bap1 | TRCN0000030719 | TRCN0000030721 |
| Bcap29 | TRCN0000099810 | TRCN0000099811 |
| Cd22 | TRCN0000067945 | TRCN0000067946 |
| Cela1 | TRCN0000092406 | TRCN0000092407 |

TABLE 5-continued

List of clone IDs for shRNAs obtained from Open Biosystems/Thermo Scientific.

| Human Gene | First shRNA | Second shRNA |
|---|---|---|
| Clec5a | TRCN0000067713 | TRCN0000067715 |
| Dnase1l1 | TRCN0000108731 | TRCN0000108730 |
| Dpm1 | TRCN0000111999 | TRCN0000111996 |
| Ebf1 | TRCN0000086578 | TRCN0000086580 |
| Human Gene | | |
| Elf5 | TRCN0000081940 | TRCN0000081938 |
| Exosc7 | TRCN0000051070 | TRCN0000051068 |
| E2f4 | TRCN0000085633 | TRCN0000085634 |
| Idh3a | TRCN0000041785 | TRCN0000041786 |
| Megf8 | V3LMM_497156 | V3LMM_457695 |
| Mmp7 | TRCN0000031250 | TRCN0000031251 |
| Prkch | TRCN0000022812 | TRCN0000022811 |
| Rcvrn | TRCN0000053267 | V3LMM_504872 |
| Rpp38 | TRCN0000099598 | TRCN0000099599 |
| Stk11 | TRCN0000024146 | TRCN0000024147 |
| Styxl1 | TRCN0000071409 | TRCN0000071412 |
| Tceal1 | TRCN0000108607 | TRCN0000108608 |
| Tmem140 | TRCN0000177850 | TRCN0000178239 |
| Traf4 | TRCN0000067747 | TRCN0000067743 |
| Ubap2l | TRCN0000007677 | TRCN0000007679 |
| Wnt7b | TRCN0000071779 | TRCN0000071780 |

TABLE 6

List of primer sequences used for quantitative real-time RT-PCR.

| Human Gene | Forward primer sequence (5' → 3') | # | Forward primer sequence (5' → 3') | # |
|---|---|---|---|---|
| BAP1 | ATCTGGGTCCTGTCATCAGC | 1. | GCTGCCTTGGATTGGTCTG | 2. |
| BCAP29 | AACTAGTAGAAGACCAGGAG | 3. | CGAAAGTCTCTCTGACTGC | 4. |
| CD22 | CACCTCAATGACAGTGGTCAG | 5. | TGGATCGGATACCCATAGCAG | 6. |
| CELA1 | TCCAGCTCCTCCTACTGG | 7. | CAGAATACTTGCCATTCACC | 8. |
| CLEC5A | AGGTGGCGTTGGATCAACAA | 9. | TTAGGCCAATGGTCGCACAG | 10. |
| DNASE1L1 | CTGCACACCACTCCTAAGGC | 11. | CAGGCGCTTTTTGGTCAGT | 12. |
| DPM1 | ATGGATGCTGATCTCTCACACC | 13. | CCATTTCCTTTGTAGCGAGTTCC | 14. |
| EBF1 | CCTGGTGTTGTGGAAGTCACA | 15. | GCTCAACGAACCCACCATC | 16. |
| ELF5 | GCTGATTCCAACTGCTTGAAAAC | 17. | CAGTTTTCTTCAGGAGATAGAAGC | 18. |
| EXOSC7 | CCAAATGAAGGCTACTTGGAGT | 19. | TAGAGGGTGTTAGCGATCTCG | 20. |
| E2F4 | ATCGGGCTAATCGAGAAAAAGTC | 21. | TGCTGGTCTAGTTCTTGCTCC | 22. |
| IDH3A | AGCCGGTCACCCATCTATGAA | 23. | TAGAGACACATGGTCGGACAT | 24. |
| LILRA3 | GCTCACTCAGCTCCAACC | 25. | TCACCAGCCTTGGATTCG | 26. |
| LYN | TTCTGGTCTCCGAGTCACTCA | 27. | GCCGTCCACTTAATAGGGAACT | 28. |
| MEGF8 | CGCCTGTCTTCGTCACGTC | 29. | CTGCTGAAAGGTGAGCAAGT | 30. |
| MMP7 | GTGGAGTGCCAGATGTTGC | 31. | ATCGATCCACTGAATATGCG | 32. |
| PRKCH | GTGACTTGATGTTCCACATTCAG | 33. | ATTGTCCAGTTTCAGATCTCTATAG | 34. |
| RCVRN | CACGCCGGAAAAGCGAGC | 35. | GGATCAGTCGCAGAATTTCC | 36. |
| RPP38 | GACTTTGTGGACGAAGTAAGAGC | 37. | GCTTTCCAGAGGTTCAGTCTC | 38. |
| STK11 | CTGCAAGCAGCAGTGAGG | 39. | AACCGGCAGGAAGACTGAG | 40. |
| STYXL1 | GACCCCAAGATTCAGAAGG | 41. | TCCGGGGAATCTTCTATCC | 42. |
| TCEAL1 | TCGTTCTCGCCCGCAATTTAG | 43. | GATAAGGACGGCTCCGTTTTG | 44. |
| TMEM140 | TCGGCTTCTATAACTTCTGCCT | 45. | CTGTTGCACTGGGCTAGGAG | 46. |
| TRAF4 | TGCCTATCCGCTGCATCC | 47. | TTCATGGGGCAGCGATTAGC | 48. |
| UBAP2L | ATAGCAGCGGCAATACGTGG | 49. | GAAGACACATTAGAGGCAGTGAA | 50. |

TABLE 6-continued

List of primer sequences used
for quantitative real-time RT-PCR.

| | Forward primer sequence (5' → 3') | # | Forward primer sequence (5' → 3') | # |
|---|---|---|---|---|
| WNT7B | GAAGCAGGGCTACTACAACCA | 51. | CGGCCTCATTGTTATGCAGGT | 52. |
| ZACN | GAGAGGGGAACAGCGAGAG | 53. | CAGTCTCAGGCCAGCTTCTC | 54. |
| Mouse Gene | | | | |
| Bap1 | TAGTCCTCCCAGCAAATGTAAG | 55. | GTCTTCCTCCTCCTGCATAG | 56. |
| Bcap29 | TTCTGTCTGCCCTTTATTCCTCC | 57. | TCTTACTTCTCTCACGGCATCT | 58. |
| Cd22 | AAGCTGGATGTCCATTATGCTC | 59. | TCTGTAGGAGGTGACGTCTG | 60. |
| Cela1 | TCTGGATGCCAGGGTGATTC | 61. | TATTCATCCAGGAAATGTAAGCAG | 62. |
| Mclec5a | GAAACTGGGATTTTCACCAAGG | 63. | TCCTGAAGATACTTCAGTTTCTC | 64. |
| Dnase1l1 | TATGTGTATATCTACAGGTCTGAC | 65. | ACCACACTTGGAAGAGTTTTGC | 66. |
| Dpm1 | GTAATTTTGATATTGTCTCTGGAAC | 67. | CTTCTTTTCGGTATAATCTGAAGC | 68. |
| Ebf1 | CTCACCCTATGCCATTGTGC | 69. | CGAAAGCACTCTTCTGTTTCAC | 70. |
| Elf5 | TGCCTTTGAGCATCAGACAG | 71. | TACTGGTCGCAGCAGAATTG | 72. |
| Exosc7 | GTGATGACCTTGGCACAGAG | 73. | CATTCCAGCAGCAGCACATC | 74. |
| E2f4 | ACATCTGAGATTGCAGTGAGTG | 75. | TACTACTATCCAGCAGTGCAG | 76. |
| Idh3a | TGGGTGTCCAAGGTCTCTC | 77. | CTCCCACTGAATAGGTGCTTTG | 78. |
| Megf8 | CTGCCAGTGTTCTAGGAAACTAC | 79. | ATGTGAGTAACGGCCACTAGG | 80. |
| Mmp7 | TGAGGACGCAGGAGTGAAC | 81. | CGTCCTTTGTAAGACTGAAGTC | 82. |
| Prkch | TCCGGCACGATGAAGTTCAAT | 83. | TACGCTCACCGTCAGGTAGG | 84. |
| Rcvrn | ACGACGTAGACGGCAATGG | 85. | CCGCTTTTCTGGGGTGTTTT | 86. |
| Rpp38 | CTTCTGCTCAGGGTTTTCAAG | 87. | ATGTCTTCTCTCTCCAAGGTG | 88. |
| Stkl1 | AGTATGACTGTAGTGCCCTAC | 89. | CAGGACCTGTCCAGGCAC | 90. |
| Styxl1 | CTGCTTTTCTGCGAGCCAAC | 91. | TGTCGTTTTGATCGGACATCC | 92. |
| Tceal1 | GTATCCGCCCTCAATTCATAG | 93. | CTCCGTTTTGCCTTCCAATGC | 94. |
| Tmem140 | CAGCGTTGGTTTTTGTCTCCC | 95. | GAGGAGAGCGTAGAACATCAG | 96. |
| Traf4 | CCCGGCTTCGACTACAAGTTC | 97. | TCAGGGCATTTGAAGACTCCT | 98. |
| Ubap2l | TGCTACAACTTCAGGAAAAGCTC | 99. | GTCTGGAGCATCTGTAAATCATC | 100. |
| Wnt7b | CCCGATGCCATCATTGTGATC | 101. | GTAGGGAGTCGAGAGGCTG | 102. |

, SEQ ID NO.

Cell Lines and Culture

BCR-ABL+ positive human CML cell lines K562 (ATCC), K562R (kindly provided by Nicholas J. Donato, University of Michigan) and KYO-1 (kindly provided by Brian Druker) were maintained in RPMI 1640 medium containing 10% fetal bovine serum (FBS), 4 mM L-glutamine, 100 units/ml penicillin, and 100 µg/ml streptomycin. 32D/BCR-ABL cells (kindly provided by Tomasz Skorski, Temple University) were maintained in RPMI 1640 with 10% FBS.

RNAi Screen

The RNAi Consortium (TRC) lentiviral human shRNA library (Open Biosystems/Thermo Scientific) was obtained through the University of Massachusetts RNAi Core facility. Twenty-two lentivirus pools, each comprising 5000 shRNA clones, were generated with titers of ~2×10$^7$ cfu/ml, as previously described (47). 2×10$^6$ K562 cells were transduced at a multiplicity of infection <1 with the lentiviral stocks in 6-well plates, and 2 days later puromycin selected (1 µg ml$^{-1}$) for 5 days. Cells were then treated with 20 µM IM (LC Laboratories) for 7 days, and washed twice with fresh medium until >99% of control cells (i.e., those expressing a non-silencing shRNA) died off. Surviving cells from all shRNA pools were combined and allowed to recover in IM-free medium with 1 µg/µl puromycin for 4 days. Live cells were sorted out with a Dead Cell Removal kit (Miltenyi Biotec) and harvested, and genomic DNA was prepared for sequencing identification of the integrated shRNA as previously described (Gavin et al., Nature 449, 1073-1077 (2007)).

Cell Viability Assay

To validate candidates, K562 or KYO-1 cells were stably transduced with a lentivirus carrying an individual shRNA and puromycin selected for 5 days. $2.5 \times 10^3$ IMSG KD K562 cells or $1 \times 10^4$ IMSG KD KYO-1 cells were plated in 96-well plates, and IM (10 µM for K562 cells or 0.1 µM for KYO-1 cells) or vehicle (DMSO) was added for 3 days. MTT reagent (Promega) or Alamar Blue (Invitrogen) was added to each well in 1:10 volume and incubated, and absorbance at 570 nm was recorded using a VICTOR$^3$ (PerkinElmer) or SpectraMAX M5 (Molecular Devices) plate reader.

Figure 3:
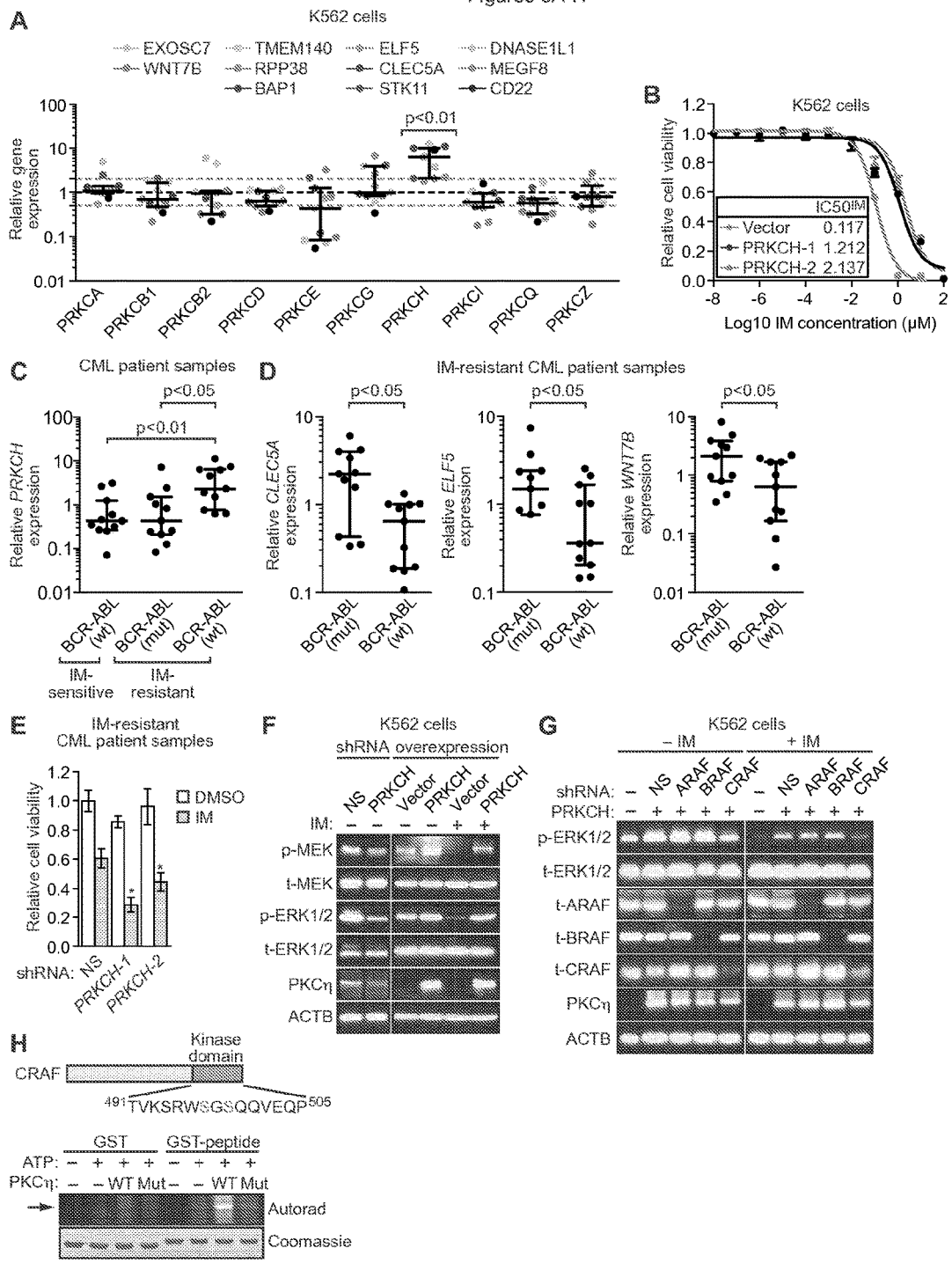
FIGS. 3A-H. IMSG knockdown increases RAF/MEK/ERK signaling through upregulation of PKCη, an activator of CRAF. (A) qRT-PCR analysis monitoring expression of different PKC isotypes in IMSG KD K562 cells. Each colored dot represents an individual IMSG KD K562 cell line. Error bars indicate median with interquartile range. The results were normalized to that obtained with the NS control shRNA, which was set to 1. The dashed lines indicate >2-fold change in gene expression relative to that obtained with the NS shRNA. (B) Relative IC50$^{TM}$ in K562 cells expressing empty vector and in two independently derived K562 clonal cell lines ectopically expressing PRKCH (n=4). Data are represented as mean±SD. (C) qRT-PCR analysis monitoring expression of PRKCH in BCR-ABL wild-type IM-sensitive patient samples (n=11), and BCR-ABL mutant (n=11) or BCR-ABL wild-type (n=11) IM-resistant CML patient samples. Error bars indicate median with interquartile range. (D) qRT-PCR analysis monitoring expression of three IMSGs in BCR-ABL mutant (n=11) or BCR-ABL wild-type (n=11) IM-resistant CML patient samples. For ELF5, BCR-ABL mutant (n=9). Error bars indicate median with interquartile range. (E) Relative viability, as measured by trypan blue cell counting, of primary leukemic cells from BCR-ABL independent IM-resistant CML patient samples (n=5) expressing a NS or PRKCH shRNA and treated with DMSO or IM. The results were normalized to that obtained with DMSO-treated cells expressing a NS shRNA, which was set to 1. Data are represented as mean±SEM. *P≤0.05, **P≤0.01. Statistical tests and exact P values are provided in table 4. (F) Immunoblot analysis monitoring RAF/MEK/ERK activity (as measured by p- and t-MEK and p- and t-ERK1/2) in PRKCH KD K562 cells (left) and in K562/PRKCH-1 cells in the absence or presence of IM (right). (G) Immunoblot analysis monitoring p- and t-ERK1/2 levels in K562/PRKCH-1 cells expressing an ARAF, BRAF or CRAF shRNA, treated with DMSO or IM for 1 h. (H) (Top) Schematic of CRAF showing the kinase domain bearing a potential PKC phosphorylation site at S497/S499. (Bottom) In vitro phosphorylation assay. Wild-type (WT) or kinase-dead mutant (Mut; K384R) PKCη was used in an in vitro phosphorylation reaction containing either GST or a GST-CRAF(aa491-505) fusion-protein. The phosphorylated product was visualized by autoradiography. The Coomassie-stained gel shows the abundance of each protein.

For other cell viability assays, IMSG KD K562 cells or K562/PRKCH cells were treated for 3 days with a range of IM concentrations as indicated (FIGS. 1E and 3B), or 0.1 µM IM, 1.5 nM trametinib or both (FIGS. 4, A and B), and analyzed as described above. For FIGS. 1E and 3B and FIG. 12, data were plotted in GraphPad Prism and a dose response curve was fit with nonlinear regression to calculate IC50$^{IM}$. For FIG. 1F, IMSG KD K562 cells were treated with 10 µM IM or 500 nM dasatinib (ChemieTeK) and cell viability was analyzed as described above. The curve was fit with linear regression and correlation coefficient was calculated using GraphPad Prism.

Colony Formation Assay

Figure 4:
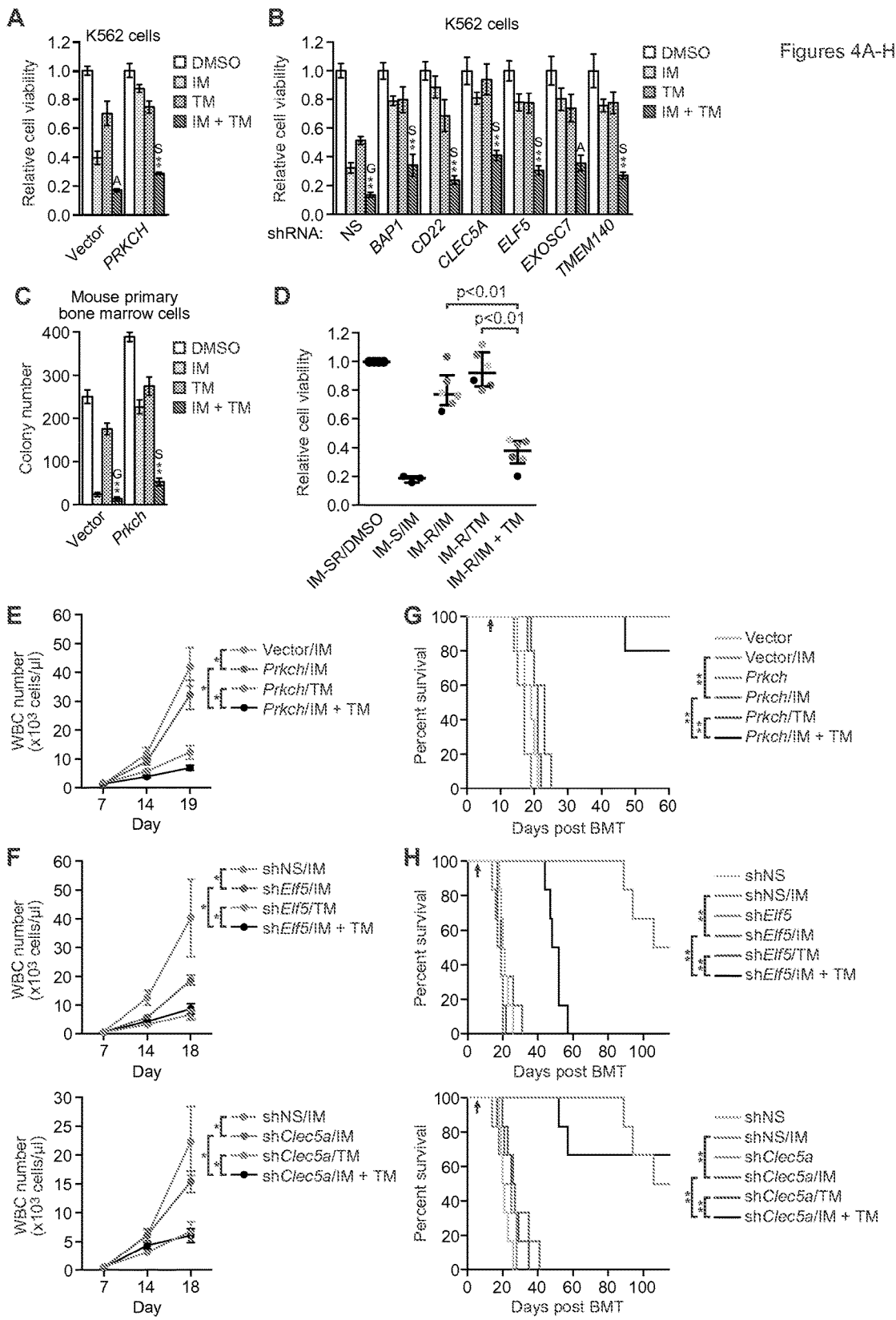
FIGS. 4A-H. Combined treatment with IM and a MEK inhibitor has beneficial effects. (A and B) Cell viability, as measured by MTT assay, of K562/PRKCH-1 (A; n=4) or IMSG KD K562 cells (B; n=3 or 4) treated with 0.1 µM IM, 1.5 nM trametinib (TM) or a combination of the two drugs, as indicated. The results were normalized to that observed with DMSO, which was set to 1. Data are represented as mean±SD. Asterisks indicate comparisons between the combined drug treatment and single drug treatments. Combined drug treatment was synergistic (S), additive (A) or antagonistic (G). (C) Colony formation assay monitoring survival of BCR-ABL+ mouse primary bone marrow cells ectopically expressing Prkch and treated with IM, TM or a combination, as described in (A) (n=3). Data are represented as mean±SD. (D) Relative viability, as measured by trypan blue cell counting, of primary leukemic cells isolated from IM-sensitive (IM-S) CML patients and treated with 5 μM IM (n=3), or isolated from BCR-ABL-independent IM-resistant (IM-R) CML patients and treated with 5 μM IM, 5 μM TM or a combination (n=6). The results were normalized to those obtained by DMSO treatment of the same samples (IM-S or IM-R [IM-SR]), which was set to 1. Error bars indicate median with interquartile range. Matched samples from the same patient are indicated by dots of the same color. (E and F) White blood cell (WBC) count of leukemic mice derived by transplantation of BCR-ABL+ mouse primary bone marrow cells ectopically expressing Prkch (E) or knocked down for an IMSG (F), and treated at day 7 with either IM, TM or a combination of the two drugs as indicated (n=4 or 5 mice per group). Data are represented as mean±SEM. The same NS control is used in the two graphs shown in (F), which were derived from a single experiment. (G and H) Kaplan-Meier survival curves of leukemic mice derived as described in (E and F). The indicated cohorts of mice (n=5 for Prkch overexpression and n=6 for IMSG knockdown) were treated with either vehicle, IM (100 mg/kg twice a day), TM (2 mg/kg once a day), or both IM and TM by oral gavage starting at day 7 (indicated by the arrow). The same NS control is used in the curves shown in (H), which were derived from a single experiment. *P≤0.05, **P≤0.01. Statistical tests and exact P values are provided in table 4.
Figure 5:
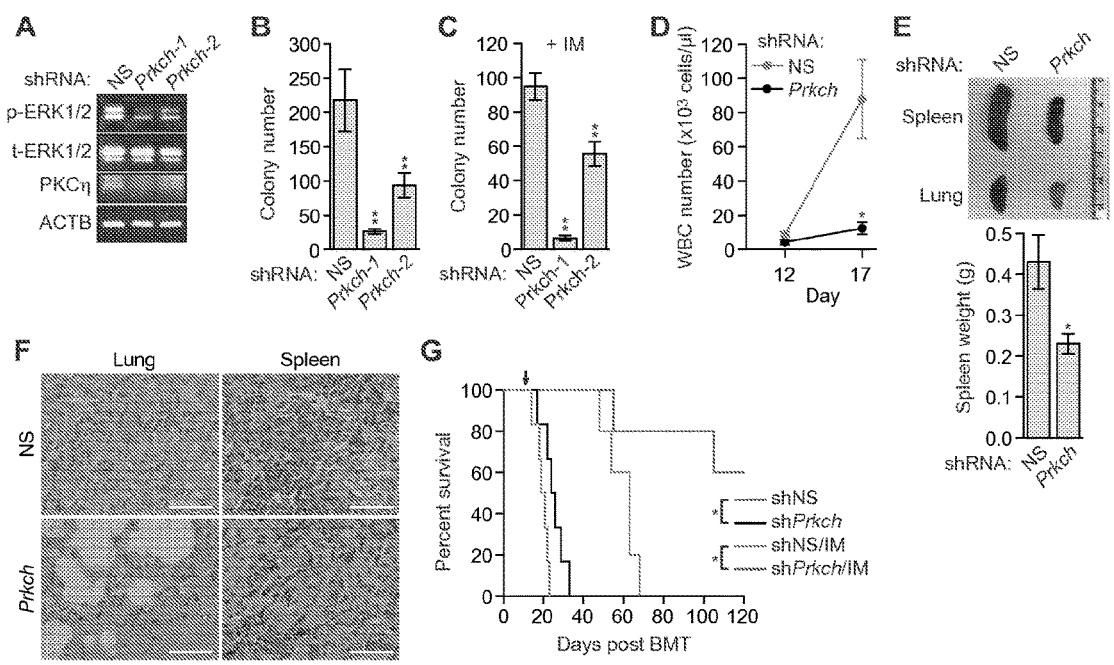
FIGS. 5A-G. PRKCH modulates proliferation of BCR-ABL+ cells, disease progression, and IM-sensitivity. (A) Immunoblot analysis monitoring p- and t-ERK1/2 levels in BCR-ABL+ mouse primary bone marrow cells expressing an NS shRNA or one of two Prkch shRNAs. (B) Colony formation assay after knockdown of Prkch in BCR-ABL+ mouse primary bone marrow cells (n=3). Data are represented as mean±SD. (C) Colony formation assay monitoring survival of BCR-ABL+ mouse primary bone marrow cells expressing a NS or one of two Prkch shRNAs and treated with 0.1 μM IM. Data are represented as mean±SD. (D) WBC count of leukemic mice derived by transplantation of Prkch KD BCR-ABL+ mouse primary bone marrow cells (n=4 or 5). Data are represented as mean±SEM. (E) (Top) Representative spleen and lung images of leukemic mice derived as described in (D). Mice were sacrificed at day 17. (Bottom) Spleen weight of mice (n=4). Data are represented as mean±SEM. (F) Hematoxylin and eosin (H&E) staining of spleen and lung sections from leukemic mice derived as described in (D). Scale bars, 50 μm. (G) Kaplan-Meier survival curve of untreated leukemic mice (n=6) or leukemic mice treated with IM at day 14 (indicated by the arrow) (n=5), derived as described in (D). *P≤0.05, **P≤0.01. Statistical tests and exact P values are provided in table 4.

For FIG. 1D, mouse primary bone marrow cells were harvested from CML mice as described below, and subjected to two rounds of infection with a mouse IMSG shRNA lentivirus (listed in table 5). Two days later, $5 \times 10^4$ IMSG KD cells were mixed with cytokine-free methylcellulose-based medium (MethoCult M3234; STEMCELL Technologies) and 0.5 µM IM and plated in 35 mm dishes. Colonies were counted under brightfield microscope at day 7. For FIG. 4C, primary bone marrow cells were transduced for two rounds with a retrovirus expressing Prkch, generated by PCR amplifying mouse Prkch cDNA (an MGC clone; Open Biosystems/Thermo Scientific) using forward (5'-ATAGGTTAACGCCACCATGTCGTCCGGCACGATGA-3'; SEQ ID NO:103) and reverse (5'-ATAGGAATTCCTACAGTTGCAATTCCGGTGA-3'; SEQ ID NO:104) primers, and digesting the PCR product with HpaI and EcoRI and cloning it into MSCV-IRES-GFP (Addgene plasmid 20672). Two days after transduction, $5 \times 10^4$ cells were mixed with methylcellulose and 0.5 µM IM, 2 nM trametinib (ChemieTek) or both. For FIGS. 5 B and C, primary bone marrow cells were collected from Prkch knockdown CML mice (generated using a retrovirus co-expressing BCR-ABL and a Prkch shRNA; see below), and 1×105 cells were plated in methylcellulose in the absence (FIG. 5B) or presence of 0.1 µM IM (FIG. 5C). For FIG. 7C, primary bone marrow cells were collected from either NS or Prkch knockdown CML mice, BCR-ABL+ murine stem cells (Lin−Sca1+Kit+) were isolated from the mice by fluorescence activated cell sorting (FACS), and IM sensitivity determined as described above for FIGS. 5, B and C.

Immunoblot Analysis

After 5 days puromycin selection, $\sim 1 \times 10^6$ IMSG KD K562 cells were plated into 6-well dishes and treated with 10 µM IM for 36 hours. Cells were harvested and lysed with RIPA buffer (10×, 200 mM HEPES pH 6.8, 1400 mM NaCl, 25 mM $MgCl_2$, 25 mM $CaCl_2$, 10% NP40, and 5% sodium deoxycholate) plus phosphatase (Sigma) and protease inhibitors (Roche). Blots were probed with the following primary antibodies, all obtained from Cell Signaling Technology: BCR-ABL PathScan (p-BCR-ABL, p-STAT5, p-CRKL) (#5300S), total BCR-ABL (#2862S), p-ERK1/2 (#4377S), total ERK1/2 (#4695S), t-STAT5 (#9358S), p-AKT (#4060S), t-AKT (#4685S), p-SFK (#2105S), t-LYN (#2796S), t-CRKL (#3182S), p-MARCKS (#8722S), t-MARCKS (#5607S), ARAF (#4432S), BRAF (#9433S), CRAF (#9422S). The PKCη antibody (Santa Cruz Technology; C-15) was diluted in 5% skim milk at 1:150. The β-actin antibody (Sigma; AC-74) diluted in 5% BSA at 1:5000. Blots were developed with Pico/Femato super signal (Sigma) and visualized using autoradiography or a Bio-Rad ChemiDoc MP Imaging System.

RNA Preparation and qRT-PCR

Total RNA was isolated from cells using TriPure Isolation Reagent (Roche) followed by treatment with turbo DNase (Ambion) to remove contaminating genomic DNA. Reverse transcription was performed using MMLV reverse transcriptase (NEB) followed by qPCR using Fast SYBR Green Master Mix (Applied Biosystems) using primers listed in table 6. The expression level of each gene was normalized to that of GAPDH. Knockdown efficiency was calculated relative to that obtained with a control non-silencing shRNA.

In Vitro Kinase Assay

A plasmid expressing Flag-tagged PKCη was generated by PCR amplifying PRKCH from a cDNA clone (Open Biosystems/Thermo Scientific), and cloning the PCR product into expression vector p3xFlag-Myc-CMV-25 (Sigma). The kinase-dead K384R mutant was generated by PCR-based site-directed mutagenesis using PfuTurbo DNA polymerase (Agilent). Plasmids were transfected individually into 293T cells, and proteins were immunopurified from cell lysate using an anti-Flag antibody (Sigma). In vitro phosphorylation reactions were set up in a 20 µl reaction volume as follows: 1 µl $^{32}$P-γ-ATP (10 mCi), 1 µl 10 µM ATP, 0.2 mM microcystin, 4 µl 5× kinase buffer [23 mM MOPS, 11.5 mM β-glycerophosphate, 23 mM $MgCl_2$, 4.6 mM EGTA, 1.8 mM EDTA, 0.25 mM DTT (pH 7.0)], 60 nM purified Flag-PKCη diluted in 1× kinase buffer, and 10 µM substrate (GST or GST fused to a peptide corresponding to amino acids 491-505 of CRAF, purified from E. coli) diluted in 1× kinase buffer. Reactions were incubated for 30 min at 30° C. and stopped using 2× Laemmli Sample Buffer. Incorporation of the radiolabel into the peptide was monitored by autoradiography.

Flow Cytometry Analysis

Fifteen days after induction of CML-like disease (see below), bone marrow cells were flushed out of femur and tibia bones with RBC lysis buffer (155 mM $NH_4Cl$, 12 mM $NaHCO_3$, 0.1 mM EDTA), spun down at 1,000 rpm for 10 min, and washed once with PBS. $2-5 \times 10^6$ cells from each sample were aliquoted for staining. A cocktail of primary antibodies [APC-conjugated Sca-1 antibody (eBioscience), PE-conjugated c-Kit antibody (eBioscience) and Biotin-conjugated Lineage antibody cocktail (Miltenyi Biotec)] was added to each sample in a total volume of 100 µl, incubated on ice for 30 min, washed once by adding PBS (1 ml) and spin down at 1,000 rpm for 10 min. The secondary antibody (APC-eFluor780-conjugated Streptavidin; eBioscience) was added in a total volume of 100 µl, incubated for 20 min on ice, and then washed once with PBS. FACS analysis was performed immediately using an LSR II flow cytometer (BD Biosciences). The Lin+ population was separated from the Lin− population by magnetic beads (Miltenyi Biotec). GFP+Lin−Sca1+Kit+ and GFP+Lin− cells were then FACS sorted from the Lin− population, and GFP+Lin+ Gr1+ cells were FACS sorted from the Lin+ population.

For Lin−Sca1+Kit+ apoptosis staining, 5 µl Annexin-V antibody [eFluor450-conjugated Annexin V (eBioscience)] was added to each sample after the last wash, and incubated for 20 min in the dark at room temperature. Samples were washed once, and 2 µl 7AAD (eBioscience) was added within 4 h before FACS analysis.

For intracellular phosphorylated-ERK1/2 analysis, bone marrow cells isolated from leukemic mice were treated with 5 µM IM or 10 nM trametinib for 3 hours, fixed in 4% paraformaldehyde (Electron Microscopy Sciences) for 10 min at 37° C., washed twice with wash buffer (0.05% BSA in 1×PBS), spun down, and resuspended in 100 µl wash buffer. Ice-cold methanol (900 µl) was added to the cells while gently vortexing to reach a final 90% for permeabilization. Samples were incubated on ice for 30 min, washed twice, and resuspended in 100 µl wash buffer. IgG control antibody (Cell signaling) was added (at 1:100 dilution) for 10 min at room temperature for blocking, followed by addition of 2 µl conjugated IgG control (Pacific Blue-conjugated IgG$^{XP}$ Rabbit mAb, Cell Signaling) or phospho-ERK antibody (Pacific Blue-conjugated P-p44/42(T202/Y204)$^{XP}$ Rabbit mAb, Cell Signaling). Samples were gently mixed and incubated at room temperature for 1 hour. Thirty minutes after the start of the incubation, a cocktail of primary antibodies for cell surface markers (described above) was added, incubated for a further 30 min, washed once with PBS, and incubated with the secondary antibody for 20 min on ice. Samples were then washed once with wash buffer prior to FACS analysis. Relative phosphorylated ERK1/2 staining was calculated by first subtracting the IgG background staining and then normalizing the absolute fluorescence intensity (median) of the treatment group (Prkch knockdown or IM or trametinib treatment) to that of the control group (NS shRNA or DMSO).

Construction of BCR-ABL/shRNA or BCR-ABL/Prkch Co-Expression Plasmids shRNAs were subcloned from an effective TRC shRNA plasmid into the MluI site downstream of GFP in the retroviral vector MSCV-BCR-ABL-IRES-GFP (22) (using forward [5'-ATAG ACGCGTTTCTTGGCTTTATATATCTTGTGG-3'; SEQ ID NO:105] and reverse [5'-ATAG ACGCGTCAAAGTGGATCTCTGCTGTC-3'; SEQ ID NO:106] primers, where underlining indicates the MluI site) to ensure the shRNA would be expressed in the same transcript as BCR-ABL and GFP. Similarly, mouse Prkch cDNA was subcloned into MSCV-BCR-ABL-IRES-GFP as described above to generate an MSCV-BCR-ABL-IRES-mPRKCH-IRES-GFP triple gene expression construct. Virus titer was tested in NIH 3T3 cells. Briefly, 5×10$^4$ cells were plated in each well of a 6-well plate, and virus was added at 1:1 dilution with fresh DMEM medium (10% FBS) plus Polybrene (Qiagen), and then cultured for 48 hours. FACS was performed to analyze GFP percentage. Only those viruses showing ≥90% infection were used for in vivo CML induction.

Mouse Models of CML

Mice with CML-like disease were generated as previously described (22). Briefly, wild-type male C57BL/6 mice 6-8 weeks of age (Jackson Laboratory) were tail-vein injected with 5-fluorouracil (200 mg/kg; Sigma) for 4 days to enrich for slow-cycling hematopoietic stem cells. At day 5, bone marrow cells were harvested and pre-incubated overnight in the presence of IL-3, IL-6 and SCF (all from PeproTech) to increase infection efficiency. At days 6 and 7, bone marrow cells were infected with a BCR-ABL retrovirus by co-sedimentation method at 3,000 rpm for 90 min at room temperature. Four hours after the second round of retroviral infection, 0.5×10$^6$ bone marrow cells were injected into the tail vein of syngeneic recipient mice that had been lethally irradiated (twice at 550 R). Mice were randomly allocated to each group after bone marrow transplantation.

For drug treatment, mice were oral gavaged twice a day with IM (dissolved in filtered ddH$_2$O) at 100 mg/kg and/or once a day with trametinib (dissolved in 0.5% hydroxypropylmethylcellulose and 0.2% Tween-80 in filtered ddH$_2$O) at 2 mg/kg.

White Blood Count

Peripheral blood (~25 µl) was collected from mouse tail veins into Microtainer tubes (BD Biosciences), and analyzed using a Hemavet 950 FS (Drew Scientific, Inc) cell counter within 3 hours after blood collection.

Acquisition and Storage of CML Patient Samples

After informed consent in accordance with Institutional Review Board (IRB)-approved protocols, bone marrow aspirate or peripheral blood samples were collected from CML patients. For samples provided by the Druker lab and Emory University, mononuclear cells were isolated by Ficoll gradient and, depending on the number of viable cells available, cells were stored as pellets or guanidinium thiocynate (GTC) lysates (resuspended in Qiagen RLT lysis buffer+beta-mercaptoethanol) at −80° C., or resuspended in fetal bovine serum (FBS)+10% DMSO, frozen slowly overnight, and then transferred to liquid nitrogen for long-term storage. For samples provided by the University of Massachusetts Medical School, white blood cells were isolated by red cell lysis, and cells were resuspended in FBS+10% DMSO, frozen slowly overnight, and then transferred to liquid nitrogen for long-term storage. All samples were provided in a deidentified manner. Samples from normal donors were purchased from a commercial vendor (AllCells or Lonza).

Analysis of Human CML Patient Samples

To analyze gene expression in IM-sensitive and IM-resistant CML patient samples (FIGS. 3, C and D), RNA was obtained in the form of purified RNA or extracted independently from GTC lysate or Trizol stock, and qRT-PCR was performed as described above.

To culture primary cells derived from CML patients and normal individuals for functional experiments (FIGS. 3E, 4D and 7F-G and FIGS. 17A-B and 23B), frozen patient cells were first warmed for 10 min at 37° C. 1 ml of pre-warmed thawing medium (Iscove's Modified Dulbecco's Media [IMDM] with 5% FBS, 0.1 mg/ml DNase, and 400 U/ml heparin) was added slowly, followed by 10 ml of wash medium (IMDM with 5% FBS, 0.1 mg/ml DNase). After passing through a 70 µm filter, cells were spun at 300 g for 10 min. Cell pellets were then resuspended in an adequate amount of culture medium (IMDM with 20% BIT [STEMCELL Technologies], 20 ng/ml IL-3, 20 ng/ml IL-6, 20 ng/ml FLT3, 100 ng/ml granulocyte colonystimulating factor (G-CSF), and 100 ng/ml SCF [PeproTech]) and incubated overnight at 37° C. Cells were then either directly used, or further enriched for the CD34+ population using CD34 MicroBead Kit UltraPure (Miltenyi Biotec).

For PRKCH knockdown, a volume of PRKCH shRNA-GFP lentivirus equal to the volume of cells was used to infect cells at 2,000 g for 90 min at room temperature. After culturing for an additional 16-24 hours, cells were pelleted at 300 g for 10 min and resuspended in culture medium with 1% of initial cytokines, a more physiologically relevant concentration. Cells were then treated with DMSO, 5 µM IM, 5 nM trametinib, or both drugs for 4 days. The cell viability of the target population was then calculated by multiplying the percentage of target population, which was obtained by FACS analysis, and the total number of live cells, which was determined by trypan blue staining.

To analyze PRKCH expression in human CML stem cells (CD34+CD38−) and progenitor cells (CD34+CD38+) (FIG. 6B), freshly thawed CML cells or CD34+− enriched CML cells were directly stained for CD34 and CD38 cell surface markers. The target population was isolated by FACS and total RNA was extracted by Trizol for qRT-PCR analysis as described above. For bioinformatic analysis (FIG. 6C), CEL files were downloaded from Gene Expression Omnibus (GEO accession GSE43754), and PRKCH expression analysis was performed using the R program 'RMA' in the BioConductor 'oligo' package (66) with full probeset annotation.

Chromatin Immunoprecipitation (ChIP)

K562 cells (1×107) were crosslinked with 1% formaldehyde for 12 min at room temperature, followed by addition of 0.125 mM glycine for 10 min. Cells were washed twice and lysed in ChIP lysis buffer (50 mM HEPES pH 8.0, 150 mM NaCl, 1 mM EDTA, 0.1% Na-deoxycholate, 1% TritonX-100, 0.1% SDS, plus protease inhibitor) for 15 min on ice. The lysate was sonicated for 12 rounds (30 seconds on, 1 minute 30 seconds off, power output 6.0) using Sonicator 3000 (Qsonica), and clarified by centrifugation. 50 µl 50% protein-G agarose bead slurry was used to pre-clear 5 mg of chromatin for over 4 hours at 4° C. For ChIP experiments, 500 µg pre-cleared chromatin were incubated overnight with either 5 µg anti-ELF5 antibody ((N-20) X, Santa Cruz) or IgG, followed by addition of 50 µl 50% protein-G agarose bead slurry and incubation for 4 hours at 4° C. Beads were pelleted by centrifugation and washed twice with ChIP lysis buffer, once with high salt lysis buffer (ChIP lysis buffer adjusted to 1M NaCl), thrice with LiCl wash buffer (50 mM HEPES pH 8.0, 250 mM LiCl, 1 mM EDTA, 0.5% deoxycholate, 0.5% NP40, plus protease inhibitor), and once with Tris-EDTA buffer. After the last wash, the supernatant was removed and 400 µl elution buffer (1% SDS, 0.1% NaHCO3) was added and incubated for 15 min at 65° C. with occasional vortexing. Beads were pelleted, and the supernatant was transferred to a new tube and reverse-crosslinked overnight at 65° C. RNase A (2 µl of 10 mg/ml) was added to each ChIP sample and incubated for 1 hour at 37° C., followed by addition of 5 µl Protease K (20 mg/ml, Promega) and incubation for 2 hours at 55° C. DNA was phenol:chloroform extracted and isopropanol precipitated, and subjected to qPCR with the following primers: TSS-for (5'-AGGAGGAGAAGCAAGAGGAG-3'; SEQ ID NO:107) and TSS-rev (5'-CCGACCGTCCCTTCCAAG-3'; SEQ ID NO:108), 500-for (5'-GACCTTTCCTGCTCTAT-GTG-3'; SEQ ID NO:109) and 500-rev (5'-CTGCAGAG-GCTAATTACACAG-3'; SEQ ID NO:110), and 1000-for (5'-CATAGCAGCGTAGGCTAAAA G-3'; SEQ ID NO:111) and 1000-rev (5'-CGGAAGAAATTGCCTCT-TCTAG-3'; SEQ ID NO:112). Fold enrichment was calculated by setting the IgG control to a value of 1.

Luciferase Reporter Assays

A 2 kb genomic DNA region upstream of the PRKCH transcription start site was PCR amplified from a BAC clone (RP11-1069E8) using forward and reverse primers (5'-ATAGGCTAGCGTTCTGAACAGGGCCTTAGAG-3'; SEQ ID NO:113 and 5'-ATAGAAGCTTGATGCGGAC-CCTCAAATAGC-3'; SEQ ID NO:114, respectively), digested with NheI and HindIII, and ligated into the firefly luciferase reporter vector PGL4.14[luc2/Hygro] (Promega). 2 µg of this reporter and 40 ng of pRL-TK Renilla luciferase control reporter vector (Promega) were co-transfected into ELF5 knockdown or overexpression K562 cells by electroporation. After 48 hours of culturing, cells were lysed and centrifuged. Supernatants were incubated with luciferase substrate (Promega) and the luciferase activity was recorded by VICTOR3 (PerkinElmer) plate reader.

Statistics

All quantitative data were collected from experiments performed in at least triplicate, and expressed as mean+/−standard deviation. Animal experiments were expressed as mean+/−standard error of the mean. Statistical analyses were performed using R, a system for statistical computation and graphics (Ihaka and Gentleman, J Comput Graph Stat 5, 299-314 (1996)). Relative cell viability data (FIGS. 1, B and C, 3E, 4D, 7F, 7G, 9, 10A, 17B and 23B) and cell death data (FIG. 22A) were first arcsine transformed to homogenize the variance. Colony number (FIG. 1D and FIGS. 11B and 20) and cell number (FIG. 7D) data were first log transformed. Levene's test was performed to test for homogeneity of variance. When the assumption of homogeneity of variances was met, ANOVA was performed followed by predetermined contrasts within the ANOVA framework. When the assumption was violated, a non-parametric counterpart of ANOVA (Kruskal-Wallis test for completely randomized design or Friedman rank sum test for randomized complete block design) was performed. In some instances, P values were adjusted to counteract the problem of multiple comparisons (Benjamini and Hochberg, J. Roy. Statist Soc Ser B 57, 289-300 (1995)). Significant differences were considered when $P<0.05$; $*P \leq 0.05$ and $**P \leq 0.01$. Statistical tests and exact P values are provided in table 4.

Statistical analysis for drug synergy was performed using R (Ihaka and Gentleman, J Comput Graph Stat 5, 299-314 (1996)) to assess whether the combined effects from IM and trametinib were additive (responses were equal to the sum of the single-drug effects), synergistic (greater than the sum of the single-drug effects) or antagonistic (less than the sum of the single-drug effects). Two-way analysis of variance (ANOVA) was used to test for the main effects of IM and trametinib and their interaction on cell viability and apoptosis. Benjamini and Hochberg (BH)-adjusted P value was calculated to counteract the problem of multiple comparisons (Benjamini and Hochberg, J. Roy. Statist Soc Ser B 57, 289-300 (1995)). The difference between observed effects and the expected additive effects for the cell lines exposed to both drugs were compared as previously described (Slinker, J Mol Cell Cardiol 30, 723-731 (1998)). The difference was estimated as the interaction coefficient in ANOVA. For cell viability, if there was a significant positive difference (interaction coefficient >0 and BH-adjusted P value <0.05), then the impact from the combined drugs was classified as antagonism; if there was a significant negative difference (interaction coefficient <0 and BH-adjusted P value <0.05), then the impact from the combined drugs was classified as synergistic; if there was no significant difference, then the impact from the combined drugs was classified as additive. For apoptosis, if there was a significant positive difference, then the impact from the combined drugs was classified as synergism; if there was a significant negative difference, then the impact from the combined drugs was classified as antagonism.

Example 1. A Large-Scale shRNA Screen Identifies IM-Sensitizing Genes

To identify IM-sensitizing genes (IMSGs), IM-sensitive human CML K562 cells (18) were stably transduced with pools of a genome-wide human short hairpin RNA (shRNA) library (19) followed by IM treatment (FIG. 1A). Surviving cells from all pools were combined and shRNAs, corresponding to 89 genes, were identified by sequence analysis.

Figure 9:
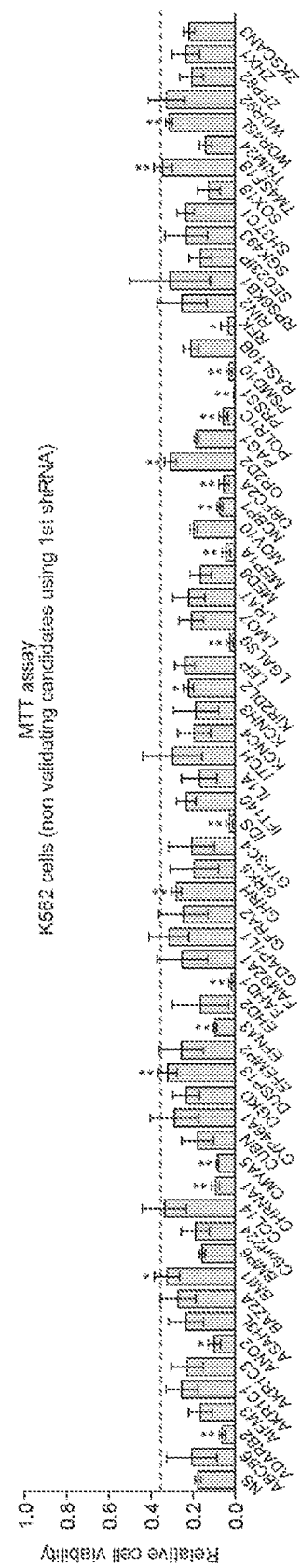
FIG. 9. IM sensitivity of non-validating candidates isolated from the primary shRNA screen. MTT assay showing relative viability of IMSG KD K562 cells in the presence of IM. The results were normalized to that obtained with DMSO-treated cells, which was set to 1. The red line indicates a 2-fold increase in cell survival relative to that of the non-silencing (NS) control shRNA; none of the shRNAs shown here were considered positive. The NS control is the same as that used in FIG. 1B. Data are represented as mean±SD (n=4). *P≤0.05, **P≤0.01. Statistical tests and exact P values are provided in table 4.
Figure 10:
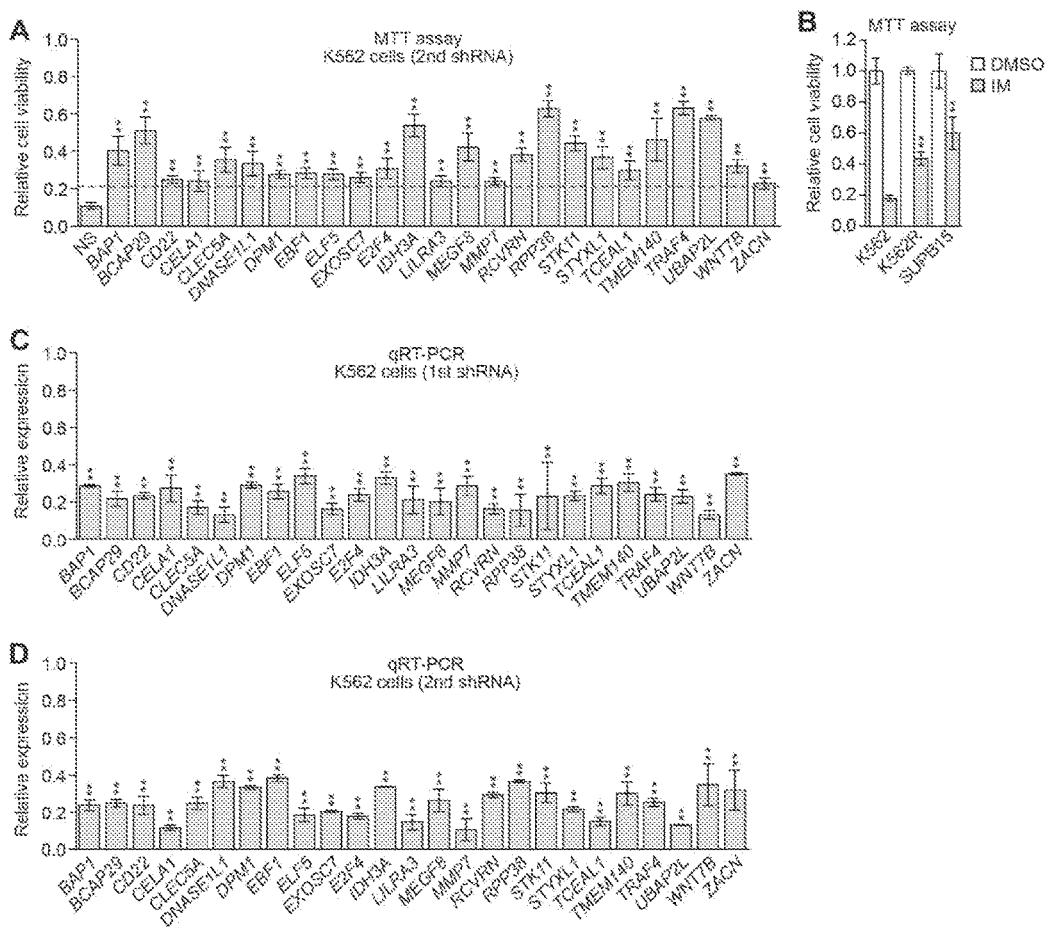
FIGS. 10A-D. Confirmation of validating candidates using a second shRNA. (A) MTT assay showing relative viability of IM-treated K562 cells expressing a second IMSG shRNA unrelated to that isolated in the primary screen and used in FIG. 1B (n=4). The results were normalized as described in FIG. 1B. IMSG shRNAs that conferred >2-fold increase in cell survival (indicated by the red line) relative to that of the NS control shRNA were considered positive. (B) MTT assay showing relative viability of IM-sensitive K562 cells, experimentally-derived IM-resistant K562R cells, and IM-resistant patient-derived SUPB15 cells treated with 10 μM IM (n=4). The results were normalized to that obtained with DMSO-treated cells, which was set to 1. (C and D) qRT-PCR analysis monitoring knockdown efficiencies, in K562 cells, of IMSG shRNAs isolated from the primary screen (B; n=3) or a second, unrelated IMSG shRNA (C; n=3). Data are represented as mean±SD. *P≤0.05, **P≤0.01. Statistical tests and exact P values are provided in table 4.

Validation experiments with individual shRNAs corresponding to those isolated from the primary screen, as well as second, unrelated shRNAs targeting the same genes, confirmed that knockdown of 25 genes conferred >2-fold increased K562 cell survival in the presence of IM relative to a control non-silencing (NS) shRNA (FIG. 1B and FIGS. 9 and 10A). The extent of IM resistance after IMSG knockdown was roughly similar to that of the well-studied experimentally-derived IM-resistant cell line K562R and an IM-resistant patient-derived cell line, SUPB15 (FIG. 10B). Quantitative real-time RT-PCR (qRT-PCR) confirmed in all cases that expression of the target gene was decreased in the corresponding K562 knockdown (KD) cell line (FIGS. 10C and D).

Figure 11:
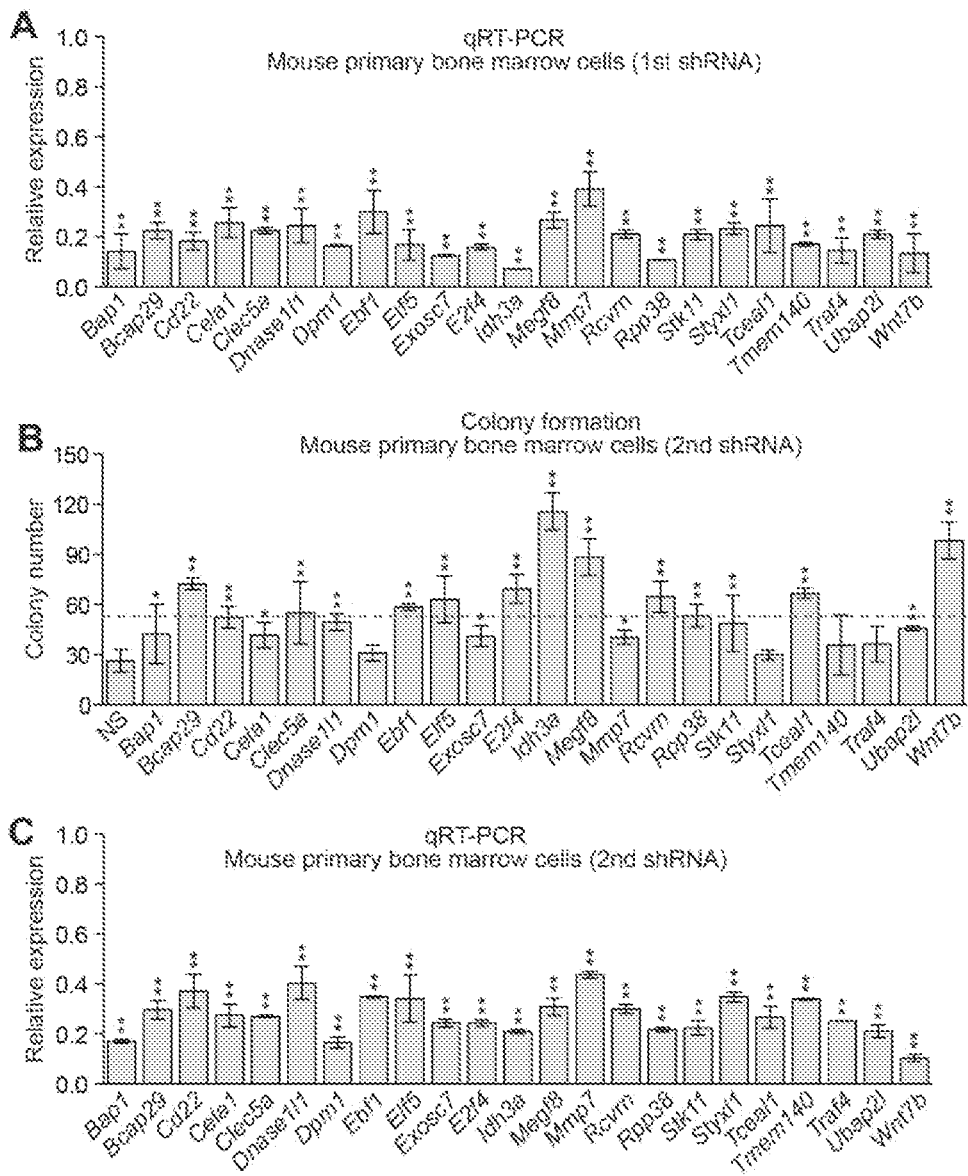
FIGS. 11A-C. IM sensitivity following candidate IMSG knockdown in mouse primary bone marrow cells. (A) qRT- PCR analysis monitoring knockdown efficiencies of mouse IMSG shRNAs in mouse primary bone marrow cells (n=3). (B) Colony formation assay monitoring survival of BCR-ABL+ mouse primary bone marrow cells expressing an IMSG shRNA in the presence of IM (n=3). IMSG shRNAs that conferred >2-fold increase in colony formation relative to that of the NS control shRNA (indicated by the red line) were considered positive. (C) qRT-PCR analysis monitoring knockdown efficiencies, in mouse primary bone marrow cells, of a second set of mouse IMSG shRNAs unrelated to those used in (A) but the same as those used in (B) (n=3). Data are represented as mean±SD. *P≤0.05, **P≤0.01. Statistical tests and exact P values are provided in table 4.

To confirm that these results were generalizable, the validated candidates were analyzed in KYO-1 cells, another IM-sensitive human CML cell line (20). FIG. 1C shows that 21 of the 25 shRNA candidates validated in KYO-1 cells. Finally, whether knockdown of the validated candidates would also confer IM resistance was tested in BCR-ABL+ mouse primary bone marrow cells. Toward this end, CML-like disease was induced in C57BL/6 mice using a BCR-ABL-expressing retrovirus (21, 22). Primary bone marrow cells were harvested, infected with a mouse candidate IMSG shRNA, and tested for their ability to form colonies in methylcellulose containing IM. Knockdown of 19 candidate IMSGs (FIG. 11A) rendered BCR-ABL+ primary bone marrow cells IM resistant (FIG. 1D). Equivalent results were obtained using a second, unrelated shRNA for each IMSG (FIGS. 11B and C).

To quantify IM resistance, we determined the IC50 for imatinib ($IC50^{IM}$) of IMSG KD K562 cells. Knockdown of 11 IMSGs increased the $IC50^{IM}$ greater than five-fold (FIG. 1E and FIG. 12), and we therefore focused on these IMSGs in our subsequent experiments. The IC50IMs of these 11 IMSG KD K562 cell lines were similar to those of IM-resistant cell lines derived from CML patients (Quentmeier et al., J Hematol Oncol 4, 6 (2011)). These 11 IMSGs are involved in diverse biological processes including transcriptional regulation, signal transduction, protein metabolism and DNA/RNA metabolism (table 1).

Next, whether knockdown of IMSGs would cause resistance to the second-generation tyrosine kinase inhibitor, dasatinib (23) was tested. As a control, K562R cells were analyzed in parallel, which are resistant to IM but sensitive to dasatinib due to over-expression of the Src family kinase (SFK) LYN (24). All of the IMSG shRNAs that conferred IM resistance also caused resistance to dasatinib (FIG. 1F).

TABLE 1

List of 11 IMSGs obtained from the genome-wide RNAi screen. All candidates were validated with a second, unrelated shRNA. Knockdown conferred IM resistance in BCR-ABL-transformed primary bone marrow cells and increased $IC50^{IM}$ greater than 5-fold in K562 cells.

| Biological process | Gene symbol | Gene name |
| --- | --- | --- |
| Cell signaling | CLEC5A | C-type lectin domain family 5, member A |
| | STK11 | Serine/threonine kinase 11 |
| | WNT7B | Wingless-type MMTV integration site family, member 7B |
| DNA/RNA metabolism | DNASE1L1 | Deoxyribonuclease I-like 1 |
| | EXOSC7 | Exosome component 7 |
| | RPP38 | Ribonuclease P/MRP 38 kDa subunit |
| Protein metabolism | BAP1 | BRCA1 associated protein-1 (ubiquitin carboxy-terminal hydrolase) |
| Transcriptional regulation | ELF5 | E74-like factor 5 (ets domain transcription factor) |
| Immunity | CD22 | CD22 molecule |
| Unknown | MEGF8 | Multiple EGF-like-domains 8 |
| | TMEM140 | Transmembrane protein 140 |

Figure 2:
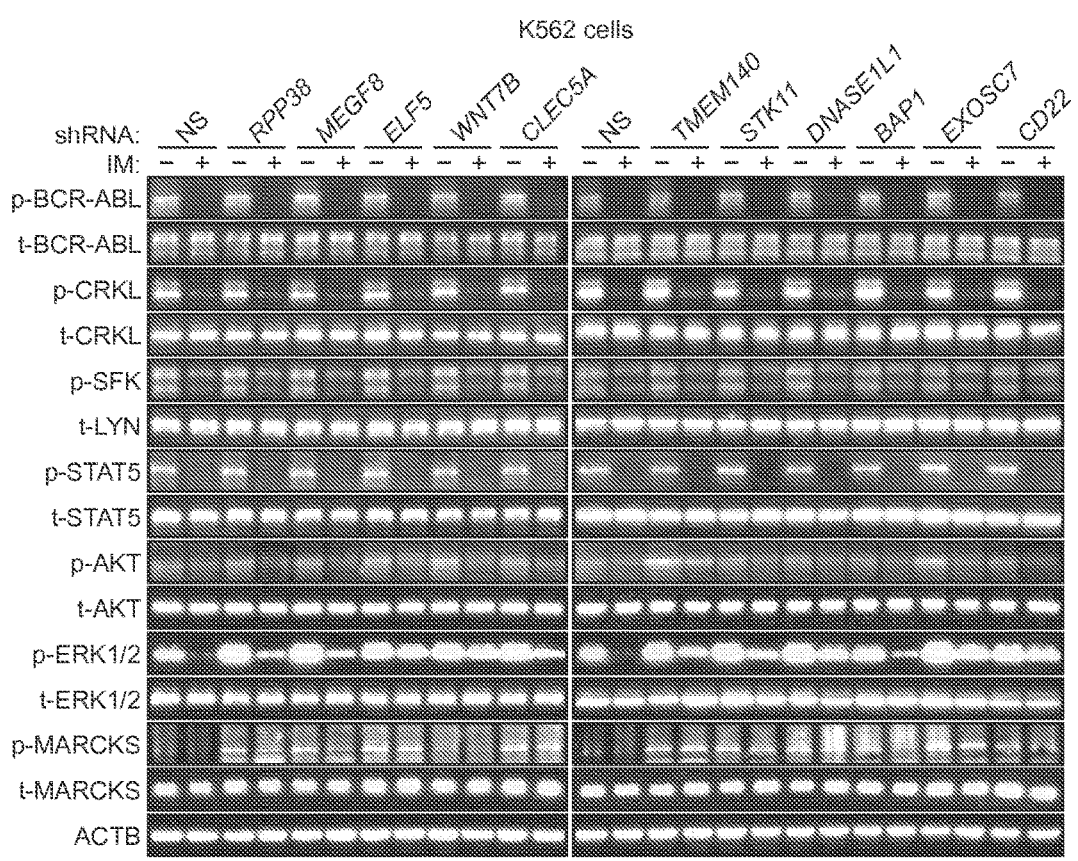
FIG. 2. Knockdown of IMSGs in BCR-ABL+ cells results in sustained RAF/MEK/ERK signaling after IM treatment. Immunoblot analysis monitoring the activity of BCR-ABL (as measured by phosphorylated (p) and total (t) BCR-ABL and CRKL), SFKs (p-SFK and t-LYN), JAK/STAT (p- and t-STAT5), PI3K/AKT (p- and t-AKT), MEK/ERK (p- and t-ERK1/2), and PKC (p- and t-MARCKS) pathways in IMSG KD K562 cells treated in the presence or absence of IM. β-actin (ACTB) was monitored as a loading control.

Example 2. Knockdown of IMSGs in BCR-ABL+ Cells Results in Sustained RAF/MEK/ERK Signaling after IM Treatment Next, a series of experiments was performed to identify the regulatory pathway(s) through which IMSGs promote IM sensitivity. IMSG KD K562 cell lines were cultured in the presence or absence of IM followed by immunoblotting for characteristic markers of relevant cell signaling pathways. The results, shown in FIG. 2, indicated that knockdown of IMSGs had no effect on total BCR-ABL levels. Moreover, in all IMSG KD K562 cell lines, IM inhibited BCR-ABL protein kinase activity, as evidenced by decreased BCR-ABL autophosphorylation and decreased phosphorylation of the BCR-ABL substrate CRKL (25). We also monitored the effect of IMSG knockdown on SFK activity, whose elevation, as mentioned above, is responsible for IM resistance in K562R cells. None of the IMSG KD K562 cell lines had elevated SFK activity or expression, consistent with their resistance to dasatinib.

The effect of IMSG knockdown was next analyzed on known downstream signaling pathways of BCR-ABL. All IMSG KD K562 cell lines had normal levels of phosphorylated STAT5 and AKT, indicating that JAK/STAT and PI3K/AKT signaling pathways were not affected by IMSG knockdown. In contrast, most of the IMSG KD K562 cell lines had increased RAF/MEK/ERK kinase pathway activity, as evidenced by increased phosphorylation of ERK1/2. As expected, after IM treatment of control K562 cells, there was a substantial decrease in phosphorylated-ERK1/2 levels. However, all of the IMSG KD K562 cell lines had, to varying extents, sustained levels of phosphorylation of ERK1/2 following IM treatment. Thus, in IMSG KD K562 cell lines there is an alternative pathway that activates RAF/MEK/ERK signaling after inhibition of BCR-ABL.

Previous studies have reported that the protein kinase C (PKC) pathway can stimulate RAF/MEK/ERK signaling (26-28). Therefore PKC pathway activity was analyzed in IMSG KD K562 cells by monitoring phosphorylation of a universal PKC substrate, MARCKS (29). Levels of MARCKS phosphorylation were elevated in all IMSG KD K562 cell lines, indicating elevated PKC activity.

Example 3. PRKCH is Upregulated in BCR-ABL-Independent IM-Resistant CML Cell Lines and Patient Samples Next, the PKC family member(s) responsible for the increased PKC activity were identified. The qRT-PCR results, shown in FIG. 3A, showed that PRKCH, which encodes PKCη, was upregulated in nearly all IMSG KD K562 cell lines. Similar results were obtained with a second shRNA targeting each IMSG (FIG. 13A). Immunoblot analysis confirmed that PKCη protein levels were also increased in the IMSG KD K562 cell lines (FIG. 13B).

As a first step toward understanding the basis by which IMSGs regulate PRKCH expression, one of the IMSGs, ELF5, a known transcriptional repressor (Chakrabarti et al., Nat Cell Biol 14, 1212-1222 (2012); Escamilla-Hernandez et al., BMC Mol Biol 11, 68 (2010)), was further analyzed. A chromatin immunoprecipitation assay was used; the results showed that ELF5 was directly bound at the transcription start site of PRKCH (FIG. 14A), consistent with the results of a study analyzing ELF5 occupancy genome-wide (Kalyuga et al., PLoS Biol 10, e1001461 (2012)). Moreover, we found that expression of a PRKCH promoter-*luciferase* reporter construct was increased by ELF5 knockdown and, conversely, decreased by ectopic expression of ELF5 (FIGS. 14B and C). Thus, ELF5 is a direct transcriptional repressor of PRKCH, explaining why decreased ELF5 levels result in increased PRKCH expression.

To verify that increased PKCη expression is responsible for the IM resistance, we derived K562 cell lines that over-expressed PRKCH (K562/PRKCH cells) to varying degrees. In several K562/PRKCH cell lines, PKCη levels were comparable to those found in IMSG KD K562 cells (FIG. 15A). The elevated PRKCH expression resulted in a 10-20-fold increase in IM resistance (FIG. 3B). Conversely, knockdown of PRKCH abrogated the IM resistance of representative IMSG KD K562 cell lines (FIG. 15B).

To determine the clinical relevance of these results, PRKCH mRNA levels were analyzed in IM-resistant CML patient samples harboring wild-type BCR-ABL. As a control, PRKCH mRNA levels were also analyzed in IM-resistant CML patient samples that contained a known IM-resistance mutation in BCR-ABL (table 2). The results shown in FIG. 3C show that PRKCH mRNA levels were significantly (P<0.01) higher in IM-resistant CML patient samples containing wild-type BCR-ABL compared to those with mutant BCR-ABL. In addition, the average expression levels of three IMSGs (CLEC5A, ELF5, and WNT7B) were significantly (P<0.01, <0.05, <0.05, respectively) lower in IM-resistant CML patient samples containing wild-type BCR-ABL compared to those with mutant BCR-ABL (FIG. 3D). Moreover, in all 11 IM-resistant CML patient samples containing wild-type BCR-ABL at least one IMSG was down-regulated >2-fold, and in 9/11 samples at least one IMSG was down-regulated >5-fold, relative to the average expression in IM-resistant mutant BCR-ABL samples (table 3). Finally, the results in FIG. 3E show that knockdown of PRKCH increased IM sensitivity of leukemic cells from BCR-ABL-independent IM-resistant CML patients.

[1]WT, BCR-ABL wild-type; Mut, BCR-ABL kinase domain mutant

[2]AP, accelerated phase; BC, blast crisis; CP, chronic phase; Ly BP, lymphoid blast crisis phase; My BP, myeloid blast crisis phase.

OHSU=Druker lab, OHSU Knight Cancer Institute; WCI=Hematology Bank, Winship Cancer Institute; UMMS=Department of Pathology, UMMS BM=Bone marrow; PB=Peripheral blood

TABLE 2

List of CML patient samples used

| Sample ID[1] | Source | BCR-ABL mutation | CML phase[2] | Origin | IM resistant/ sensitive | Basis of IM resistance | Relevant FIG. |
|---|---|---|---|---|---|---|---|
| WT-1 | OHSU | — | CP | BM | Resistant | Cytogenic relapse or suboptimal primary response to IM | FIG. 3C and 3D |
| WT-2 | OHSU | — | CP | BM | Resistant | Cytogenic relapse or suboptimal primary response to IM | FIG. 3C and 3D |
| WT-3 | OHSU | — | CP | BM | Resistant | Cytogenic relapse or suboptimal primary response to IM | FIG. 3C and 3D |
| WT-4 | OHSU | — | CP | BM | Resistant | Cytogenic relapse or suboptimal primary response to IM | FIG. 3C and 3D |
| WT-5 | WCI | — | My BP | BM | Resistant | Loss of hematological response | FIG. 3C and 3D |
| WT-6 | WCI | — | CP | BM | Resistant | Loss of cytogenic response | FIG. 3C and 3D |
| WT-7 | WCI | — | My BP | BM | Resistant | Lack of major cytgenic response | FIG. 3C and 3D |
| WT-8 | WCI | — | CP | BM | Resistant | Lack of major molecular response | FIG. 3C and 3D |
| WT-9 | WCI | — | CP | BM | Resistant | Lack of major cytgenic response | FIG. 3C and 3D |
| WT-10 | WCI | — | CP | PB | Resistant | Loss of complete cytogenic response | FIG. 3C and 3D |
| WT-11 | WCI | — | CP | PB | Resistant | Loss of hematological response | FIG. 3C and 3D |
| Mut-1 | OHSU | G250E | CP | BM | Resistant | Cytogenic relapse or suboptimal primary response to IM | FIG. 3C and 3D |
| Mut-2 | OHSU | M244V | AP | BM | Resistant | Cytogenic relapse or suboptimal primary response to IM | FIG. 3C and 3D |
| Mut-3 | OHSU | Y253F | CP | PB | Resistant | Cytogenic relapse or suboptimal primary response to IM | FIG. 3C and 3D |
| Mut-4 | OHSU | T315I | BC | Leuka- pheresis | Resistant | Cytogenic relapse or suboptimal primary response to IM | FIG. 3C and 3D |
| Mut-5 | OHSU | T315I | AP | PB | Resistant | Cytogenic relapse or suboptimal primary response to IM | FIG. 3C and 3D |
| Mut-6 | WCI | T315I, E255R | My BP | BM | Resistant | Transformation to blest phase on IM | FIG. 3C and 3D |
| Mut-7 | WCI | F317L | Ly BP | BM | Resistant | Transformation to blast phase on IM | FIG. 3C and 3D |
| Mut-8 | WCI | T315I | CP | BM | Resistant | Lack of hematological response | FIG. 3C and 3D |
| Mut-9 | WCI | T315I | CP | BM | Resistant | Loss of complete histological response | FIG. 3C and 3D |
| Mut-10 | WCI | T315I | CP | BM | Resistant | No complete histological response | FIG. 3C and 3D |
| Mut-11 | WCI | F317L | CP | PB | Resistant | Lack of major cytogenic response | FIG. 3C and 3D |
| CML(R)1 | UMMS | — | CP | PB | Resistant | Failure to achieve major molecular response | FIG. 3E and 4D and 17A-B |

TABLE 2-continued

List of CML patient samples used

Figure 6:
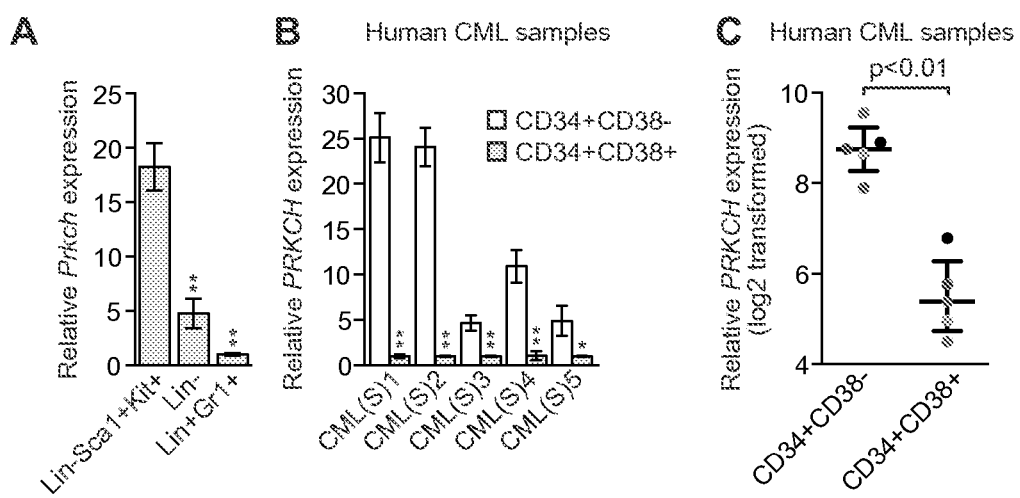
FIGS. 6A-C. IM-resistant murine and human CML stem cells contain high levels of PRKCH. (A) qRT-PCR analysis monitoring Prkch expression in BCR-ABL+ murine CML stem cells (Lin−Sca1+Kit+), progenitor cells (Lin−) and mature cells (Lin+Gr1+) (n=3). Data are represented as mean±SD. (B) qRT-PCR analysis monitoring PRKCH expression in human CML stem cells (CD34+CD38−) and progenitor cells (CD34+CD38+) isolated from CML patient samples (n=5). Data are from three technical replicates and are means±SD. (C) PRKCH expression in CD34+CD38− and CD34+CD38+ cells, mined from a previous expression profiling study (50). Matched samples from the same patient are indicated by dots of the same color. Error bars indicate median with interquartile range. *P≤0.05, **P≤0.01. Statistical tests and exact P values are provided in table 4.

| Sample ID[1] | Source | BCR-ABL mutation | CML phase[2] | Origin | IM resistant/ sensitive | Basis of IM resistance | Relevant FIG. |
|---|---|---|---|---|---|---|---|
| CML(R)2 | UMMS | — | CP | PB | Resistant | Loss of major molecular response/complete molecular response and complete cytogenic response | FIG. 3E and 4D and 17A-B |
| CML(R)3 | OHSU | — | CP | BM | Resistant | Cytogenic relapse or suboptimal primary response to IM | FIG. 3E and 4D and 17A-B |
| CML(R)4 | OHSU | — | CP | BM | Resistant | Cytogenic relapse or suboptimal primary response to IM | FIG. 3E and 4D and 17A-B |
| CML(R)5 | OHSU | — | CP | BM | Resistant | Cytogenic relapse or suboptimal primary response to IM | FIG. 3E and 4D and 17A-B |
| CML(R)6 | OHSU | — | BC | PB | Resistant | Cytogenic relapse or suboptimal primary response to IM | FIG. 4D and 17A-B |
| WT-1 | WCI | — | CP | PB | Sensitive | N/A | FIG. 3C |
| WT-2 | WCI | — | CP | PB | Sensitive | N/A | FIG. 3C |
| WT-3 | WCI | — | CP | PB | Sensitive | N/A | FIG. 3C |
| WT-4 | WCI | — | CP | BM | Sensitive | N/A | FIG. 3C |
| WT-5 | UMMS | — | CP | BM | Sensitive | N/A | FIG. 3C |
| WT-6 | UMMS | — | CP | BM | Sensitive | N/A | FIG. 3C |
| WT-7 | UMMS | — | CP | BM | Sensitive | N/A | FIG. 3C |
| WT-8 | UMMS | — | CP | PB | Sensitive | N/A | FIG. 3C |
| WT-9 | UMMS | — | CP | PB | Sensitrve | N/A | FIG. 3C |
| WT-10 | UMMS | — | CP | PB | Sensitive | N/A | FIG. 3C |
| WT-11 | UMMS | — | CP | PB | Sensitive | N/A | FIG. 3C |
| CML(S)1 | UMMS | — | CP | PB | Sensitive | N/A | FIG. 4D, 6B, 7F, 7G and 17A-B |
| CML(S)2 | UMMS | — | CP | PB | Sensitive | N/A | FIG. 4D, 6B, 7F, 7G and 17A-B |
| CML(S)3 | OHSU | — | CP | BM | Sensitive | N/A | FIG. 4D, 6B, 7F, 7G and 17A-B |
| CML(S)4 | OHSU | — | CP | BM | Sensitive | N/A | FIG. 6B |
| CML(S)5 | OHSU | — | CP | BM | Sensitive | N/A | FIG. 6B |

TABLE 3

Relative expression level of IMSGs in IM-resistant BCR-ABL-wt CML patient samples. Relative expression was calculated by determining the average expression of a given gene in all 11 mutant BCR-ABL patient samples, and dividing by the expression of the gene in the individual wild-type BCR-ABL sample. Thus, the value represents the fold down-regulation in wild-type BCR-ABL samples.
Table 3. Relative expression of IMSGs in IM-resistant BCR-ABL-wt CML patient samples.

| Sample ID | Relative expression | | | | | | | | | | | |
|---|---|---|---|---|---|---|---|---|---|---|---|---|
| | RAP1 | CD22 | CLEC5A | DNASE1L1 | ELF5 | EXOSC7 | MEGF8 | RPP38 | STK11 | TMEM140 | WNT7B | PRKCH |
| WT-1 | 0.498 | 3.723 | 13.781 | 1.231 | 9.882 | 1.299 | 3.806 | 0.541 | 0.607 | 3.559 | 15.608 | 0.204 |
| WT-2 | 1.294 | 5.749 | 2.379 | 1.198 | 8.263 | 3.765 | 9.764 | 1.872 | 2.876 | 7.013 | 10.095 | 0.688 |
| WT-3 | 1.086 | 0.651 | 12.468 | 1.058 | 1.963 | 3.295 | 0.915 | 0.784 | 1.710 | 1.780 | 1.552 | 0.176 |
| WT-4 | 0.723 | 1.042 | 1.828 | 1.401 | 1.208 | 5.210 | 1.713 | 7.357 | .0842 | 0.478 | 1.191 | 0.858 |
| WT-5 | 0.437 | 0.976 | 2.717 | 1.268 | 0.953 | .0332 | 1.431 | 0.437 | 3.192 | 0.503 | 4.125 | 0.116 |
| WT-6 | 1.222 | 0.655 | 2.400 | 0.918 | 0.790 | 1.807 | 0.696 | 2.904 | 2.692 | 0.404 | 1.341 | 0.287 |
| WT-7 | 7.906 | 16.193 | 22.845 | 2.368 | 13.862 | 0.195 | 5.888 | 5.464 | 1.770 | 3.420 | 96.887 | 2.075 |
| WT-8 | 5.844 | 3.436 | 3.760 | 2.744 | 13.486 | 2.027 | 3.055 | 1.708 | 5.362 | 3.521 | 10.836 | 1.735 |
| WT-10 | 0.574 | 0.569 | 7.508 | 0.852 | 1.954 | 2.260 | 1.537 | 0.102 | 0.795 | 0.438 | 2.595 | 2.107 |
| WT-11 | 3.589 | 2.881 | 12.961 | 1.870 | 5.556 | 0.682 | 15.511 | 7.422 | 1.651 | 8.578 | 31.855 | 0.565 |
| WT-12 | 1.509 | 2.863 | 2.445 | 1.921 | 5.634 | 1.999 | 3.179 | 0.611 | 2.273 | 1.422 | 1.549 | 0.208 |

Example 4. PKCη Increases RAF/MEK/ERK Signaling Through Phosphorylation and Activation of CRAF The next experiments were performed to understand in greater detail how PKCη increased RAF/MEK/ERK signaling. FIG. 3F shows that even a relatively modest knockdown of PRKCH in IM-sensitive K562 cells decreased both phosphorylated MEK and ERK1/2 (see also FIG. 10A) and increased IM sensitivity (FIG. 15B). Conversely, K562/PRKCH cells had increased levels of both phosphorylated MEK and ERK1/2 (FIG. 3F). Most importantly, K562/PRKCH cells maintained high levels of phosphorylated MEK and ERK1/2 after IM treatment (FIG. 3F).

The finding that PKCη affected both phosphorylated-MEK and -ERK1/2 levels indicated that PKCη functioned upstream of MEK by, for example, stimulating RAF activity. There are three known RAF kinases: ARAF, BRAF and CRAF (30). In K562/PRKCH cells, knockdown of CRAF, but not ARAF or BRAF, resulted in decreased phosphorylated-ERK1/2 levels (FIG. 3F and FIG. 15B). Most importantly, in IM-treated K562/PRKCH cells, knockdown of CRAF, but not ARAF or BRAF, resulted in loss of sustained phosphorylated-ERK1/2 levels.

To determine whether CRAF was a direct substrate of PKCη, a glutathione-S-transferase (GST) fusion-protein containing a CRAF peptide bearing a potential PKC phosphorylation site at S497/S499 (31, 32) was derived. The in vitro kinase assay showed (see FIG. 3H) that wild-type PKCη, but not a kinase-dead mutant (K384R) (33), could phosphorylate the CRAF S497/S499 site. These results are consistent with several previous findings including phosphorylation of CRAF by PKC isoforms (31, 32, 34-36), and reduced activity of a CRAF S497A/S499A mutant (32, 34).

Example 5. Combined Treatment with IM and a MEK Inhibitor Synergistically Kill BCR-ABL-Independent IM-Resistant CML Cells The results presented above show that BCR-ABL-independent IM resistance can result from increased PRKCH expression, leading to sustained RAF/MEK/ERK signaling after IM treatment. An implication of this conclusion is that simultaneous inhibition of BCR-ABL and RAF/MEK/ERK signaling might efficiently kill BCR-ABL-independent IM-resistant CML cells. To investigate this possibility, the effect of combining IM treatment with the FDA-approved MEK inhibitor trametinib (also called GSK1120212) was analyzed. Treatment with both IM and trametinib had a substantially greater effect than either drug alone in killing K562/PRKCH cells (FIG. 4A), representative IMSG KD K562 cell lines (FIG. 4B), and BCR-ABL+ mouse primary bone marrow cells over-expressing Prkch (FIG. 4C). In most instances, the effect of combined drug treatment was synergistic (table 4). The modest effect of trametinib alone on K562 cell lines likely reflects stimulation of RAF/MEK/ERK signaling by BCR-ABL. Finally, treatment with both IM and trametinib had a significantly ($P \leq 0.01$) greater effect than either drug alone in killing primary leukemic cells from BCR-ABL-independent IM-resistant CML patients (FIG. 4D and FIG. 17A). Moreover, these leukemic cells were killed more effectively by combined treatment with IM and trametinib than by IM and a JAK-STAT or PI3K inhibitor, and neither of these latter two drug combinations were significantly more effective than IM alone (FIG. 17B).

TABLE 4

Actual P values for all comparisons in this study.

| Sample | P value (shRNA vs NS) | BH-adjusted P value (shRNA vs NS) |
|---|---|---|
| FIG. 1B | | |
| Statistical test: One-way ANOVA (P value = 1.0406E-06) followed by predetermined contrasts within the ANOVA framework with Benjamini-Hochberg correction. | | |
| BAP1 | 1.07513E-06 | 5.59068E-06 |
| BCAP29 | 0.00040146 | 0.000497046 |
| CD22 | 3.00752E-05 | 8.36825E-05 |
| CELA1 | 2.68843E-08 | 2.32997E-07 |
| CLEC5A | 7.71503E-10 | 1.00295E-08 |
| DNASE1L1 | 0.000726651 | 0.000787205 |
| DPM1 | 9.38085E-06 | 4.06503E-05 |
| EBF1 | 7.19634E-05 | 0.000133646 |
| ELF5 | 0.000235868 | 0.000360739 |
| EXOSC7 | 3.21856E-05 | 8.36825E-05 |
| E2F4 | 0.000317805 | 0.000434891 |
| IDH3A | 0.000552982 | 0.000653525 |
| LILRA3 | 6.15163E-05 | 0.000123033 |
| MEGF8 | 0.00011352 | 0.000184469 |
| MMP7 | 1.8066E-05 | 6.71023E-05 |
| RCVRN | 0.000260338 | 0.000376044 |
| RPP38 | 4.7514E-05 | 0.000102947 |

TABLE 4-continued

Actual P values for all comparisons in this study.

| Sample | P value (shRNA vs NS) | BH-adjusted P value (shRNA vs NS) |
|---|---|---|
| STK11 | 2.38392E-11 | 6.19818E-10 |
| STYXL1 | 0.002841565 | 0.002955228 |
| TCEAL1 | 2.34123E-05 | 7.60901E-05 |
| TMEM140 | 0.004475609 | 0.004475609 |
| TRAF4 | 0.000616875 | 0.000697337 |
| UBAP2L | 0.000377057 | 0.000490174 |
| WNT7B | 4.09493E-05 | 9.67892E-05 |
| ZACN | 8.87069E-05 | 0.000153759 |
| FIG. 1C | | |
| Statistical test: One-way ANOVA (P value = 6.23277E-38) followed by predetermined contrasts within the ANOVA framework with Benjamini-Hochberg correction | | |
| BAP1 | 8.98213E-33 | 1.12277E-31 |
| BCAP29 | 2.17058E-22 | 9.04407E-22 |
| CD22 | 1.29641E-10 | 1.80057E-10 |
| CELA1 | 1.86785E-09 | 2.33481E-09 |
| CLEC5A | 4.92614E-25 | 3.07884E-24 |
| DNASE1L1 | 1.07278E-11 | 1.57761E-11 |
| DPM1 | 2.13891E-18 | 5.94141E-18 |
| EBF1 | 8.31631E-07 | 8.66282E-07 |
| ELF5 | 2.24623E-17 | 5.10507E-17 |
| EXOSC7 | 1.48547E-34 | 3.71366E-33 |
| E2F4 | 2.55704E-15 | 4.91739E-15 |
| IDH3A | 1.11839E-24 | 5.59197E-24 |
| LILRA3 | 1.43058E-21 | 5.1092E-21 |
| MEGF8 | 3.72116E-12 | 5.81431E-12 |
| MMP7 | 1.42847E-25 | 1.19039E-24 |
| RCVRN | 4.84833E-07 | 5.26993E-07 |
| RPP38 | 2.01321E-17 | 5.03303E-17 |
| STK11 | 2.26331E-10 | 2.97804E-10 |
| STYXL1 | 1.03672E-07 | 1.17809E-07 |
| TCEAL1 | 3.00559E-13 | 5.36713E-13 |
| TMEM140 | 2.36532E-20 | 7.39161E-20 |
| TRAF4 | 0.008468345 | 0.008468345 |
| UBAP2L | 4.54415E-17 | 9.46698E-17 |
| WNT7B | 1.88709E-12 | 3.14516E-12 |
| ZACN | 1.86812E-08 | 2.22395E-08 |
| FIG. 1D | | |
| Statistical test: One-way ANOVA (P value = 8.581e-15) followed by predetermined contrasts within the ANOVA framework with Benjamini-Hochberg correction | | |
| Bap1 | 0.000105724 | 0.000121582 |
| Bcap29 | 5.20E-05 | 6.29E-05 |
| Cd22 | 4.04E-11 | 1.55E-10 |
| Cela1 | 0.014187481 | 0.01553867 |
| Clec5a | 2.69E-09 | 6.86E-09 |
| Dnase1l1 | 1.74E-11 | 1.00E-10 |
| Dpm1 | 2.26E-09 | 6.49E-09 |
| Ebf1 | 5.32E-07 | 1.02E-06 |
| Elf5 | 8.98E-13 | 1.03E-11 |
| Exosc7 | 3.83E-12 | 2.94E-11 |
| E2f4 | 9.80E-11 | 3.22E-10 |
| Idh3a | 3.12E-11 | 1.44E-10 |
| Megf8 | 7.52E-06 | 1.24E-05 |
| Mmp7 | 0.357567304 | 0.357567304 |
| Rcvrn | 5.24E-07 | 1.02E-06 |
| Rpp38 | 2.06E-05 | 2.76E-05 |
| Stk11 | 2.16E-05 | 2.76E-05 |
| Styxl1 | 0.180762343 | 0.188978814 |
| Tceal1 | 2.13E-07 | 4.91E-07 |
| Tmem140 | 7.51E-13 | 1.03E-11 |

TABLE 4-continued

Actual P values for all comparisons in this study.

| Sample | P value (shRNA vs NS) | BH-adjusted P value (shRNA vs NS) |
|---|---|---|
| Traf4 | 1.10E−05 | 1.68E−05 |
| Ubap2l | 7.65E−07 | 1.35E−06 |
| Wnt7b | 1.20E−05 | 1.73E−05 |

FIG. 1F
Statistical test: Correlation analysis (performed in GraphPad Prism 6). Pearson's correlation coefficient was calculated to reach a two-tailed P value with 95% confidence interval.

| P value |
|---|
| 0.0117 |

Example 6. IM and a MEK Inhibitor Prolong Survival in Mouse Models of BCR-ABL-Independent IM-Resistant CML Based upon the cell culture results, the ability of this drug combination to prolong survival was analyzed in mouse models of BCR-ABL-independent IM-resistant CML. Briefly, mouse primary bone marrow cells were transduced with a retrovirus co-expressing BCR-ABL and either Prkch (FIG. 18A) or an shRNA targeting one of two representative IMSGs, Clec5A or Elf5 (FIG. 18B), followed by transplantation into lethally irradiated syngeneic mice. Combined treatment with IM and trametinib was substantially more effective than either drug alone at suppressing leukemic progression, as evidenced by a reduced white blood cell count (FIGS. 4, E and F), and prolonging survival (FIGS. 4, F and G). In addition to prolonged survival, the general appearance and behavior of mice treated with IM and trametinib was normal, suggesting minimal drug toxicity.

Example 7. PRKCH Modulates Proliferation of BCR-ABL+ Cells, Disease Progression, and IM Sensitivity The finding that knockdown of PRKCH in K562 cells reduced levels of phosphorylated-ERK1/2 (FIG. 3F) raised the possibility that PRKCH might modulate the proliferation and survival of BCR-ABL+ cells and thus affect disease progression. To investigate this possibility, mouse primary bone marrow cells were transduced with a retrovirus co-expressing BCR-ABL and a Prkch shRNA (FIG. 5A). Prkch knockdown led decreased levels of phosphorylated-ERK1/2, similar to the results in K562 cells. FIG. 5B shows that knockdown of Prkch (FIG. 19A) reduced the ability of untreated BCR-ABL+ mouse primary bone marrow cells to form colonies in methylcellulose (see also FIG. 19B). Moreover, the colony formation assay in FIG. 5C shows that knockdown of Prkch markedly increased the IM sensitivity of BCR-ABL+ mouse primary bone marrow cells.

Next, the Prkch KD bone marrow cells were transplanted into syngeneic mice to induce CML-like disease and analyzed the effect of Prkch knockdown on leukemic progression. In untreated mice, Prkch knockdown resulted in a lower white blood cell count (FIG. 5D), reduced spleen size (FIG. 5E), decreased infiltration of the lung and spleen by leukemic cells (FIG. 5F), and increased survival (FIG. 5G). Thus, in the absence of IM treatment, PRKCH promotes disease progression, although this effect may be relatively minor. More importantly, knockdown of Prkch markedly increased survival of IM-treated mice with CML-like disease (FIG. 5G).

Example 8. IM-Resistant Murine and Human CML Stem Cells Contain High Levels of PRKCH To investigate the possibility that PRKCH might contribute to the intrinsic resistance of CML stem cells to IM, a CML-like disease was induced in mice, and BCR-ABL+ murine stem cells (Lin−Sca1+Kit+), progenitor cells (Lin−) and mature cells (Lin+Gr1+) were isolated by fluorescence activated cell sorting (FACS) (Hamilton et al., Blood 119, 1501-1510 (2012); Neering et al., Blood 110, 2578-2585 (2007)). The qRT-PCR results, shown in FIG. 6A, demonstrated that IM-resistant murine CML stem cells (Hamilton et al., Blood 119, 1501-1510 (2012); Zhang et al., Cancer Cell 17, 427-442 (2010); Zhang et al., Nat Genet 44, 861-871 (2012)) and see below) had substantially higher expression of Prkch compared to murine CML progenitor and mature cells, both of which are IM sensitive ((Hamilton et al., Blood 119, 1501-1510 (2012); Li et al., Cancer Cell 21, 266-281 (2012)) and FIG. 20).

The next experiments asked whether PRKCH expression levels were also high in human CML stem cells. CML stem cells (CD34+CD38−) and CML progenitor cells (CD34+CD38+) (Corbin et al., J Clin Invest 121, 396-409 (2011); Jiang et al., Leukemia 21, 926-935 (2007); Lobo et al., Annu Rev Cell Dev Biol 23, 675-699 (2007)) were isolated from newly diagnosed CML patients. The qRT-PCR results in FIG. 6B show that IM-resistant human CML stem cells (Graham et al., Blood 99, 319-325 (2002); Corbin et al., J Clin Invest 121, 396-409 (2011); Bhatia et al., Blood 101, 4701-4707 (2003); Chomel et al., Blood 118, 3657-3660 (2011); Pellicano et al., Stem Cells 32, 1373-1379 (2014)) and see below) had substantially higher expression of PRKCH compared to human CML progenitor cells, which are IM sensitive (Corbin et al., J Clin Invest 121, 396-409 (2011); Jiang et al., Leukemia 21, 926-935 (2007)). Analysis of a published expression profiling study comparing highly enriched human CML stem and progenitor cell populations (Gerber et al., Oncotarget 4, 715-728 (2013)) revealed similar differences in PRKCH expression levels (FIG. 6C). Microarray analysis indicates that PRKCH expression is much higher in hematopoietic stem cells than in mature myeloid cells (Konuma et al., Exp Hematol 39, 697-709 e695 (2011); Bagger et al., Nucleic Acids Res 41, D1034-1039 (2013)), suggesting that high PRKCH expression may be a marker of stemness.

Figure 7:
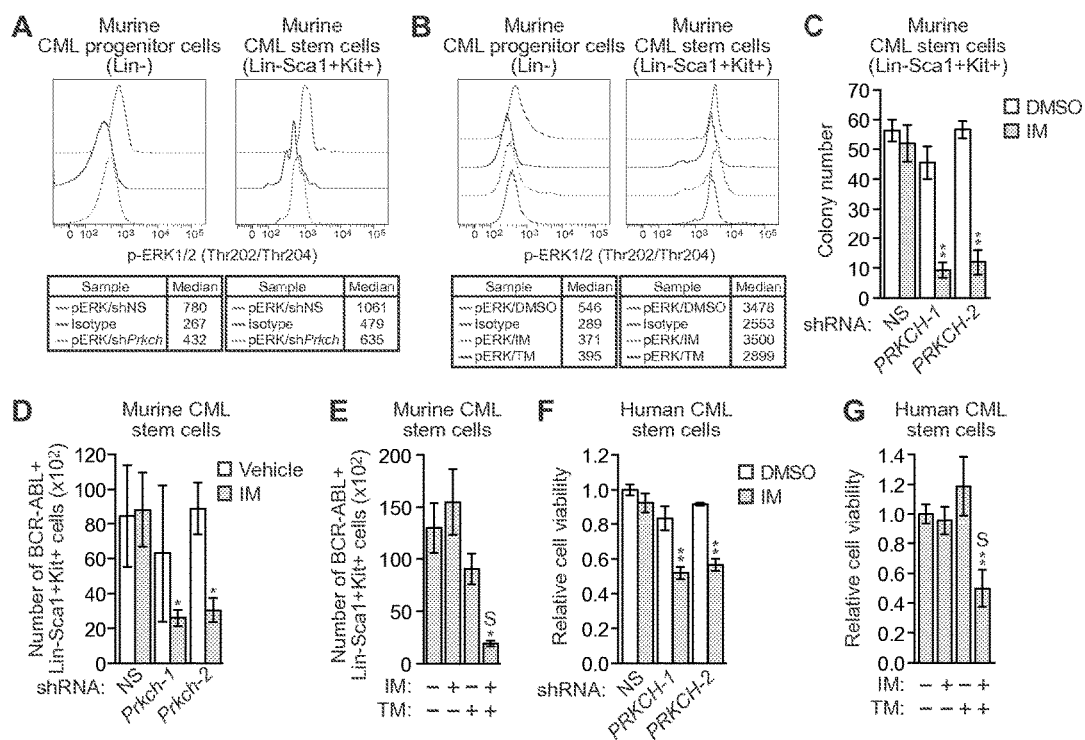
FIGS. 7A-G. High Prkch levels contribute to the IM resistance of CML stem cells. (A) Intracellular phosphorylated ERK1/2 levels in Lin− and Lin−Sca1+Kit+ BCR-ABL+ Prkch KD or control bone marrow cells. As a negative control, cells were incubated with a conjugated IgG isotype antibody. (B) Intracellular phosphorylated ERK1/2 levels in Lin− and Lin−Sca1+Kit+ BCR-ABL+ bone marrow cells treated with DMSO, IM or trametinib. (C) Colony formation assay monitoring survival of BCR-ABL+ murine stem cells expressing a NS or one of two Prkch shRNAs and treated with 0.1 μM IM (n=3). Data are represented as mean±SD. (D) FACS determination of the number of BCR-ABL+Lin−Sca1+Kit+ bone marrow cells expressing a NS or Prkch shRNA after IM treatment of mice (n=4 or 5). Data are represented as mean±SEM. (E) FACS determination of the number of BCR-ABL+ Lin−Sca1+Kit+ bone marrow cells after treatment of mice with vehicle (n=10), IM (n=12), TM (n=10) or both IM and TM (n=12). Data are represented as mean±SEM. Asterisks indicate comparisons between the combined drug treatment and single drug treatments. Combined drug treatment was synergistic (S). (F) Relative viability, as measured by trypan blue cell counting, of BCR-ABL+ human CML stem cells (CD34+CD38−) expressing a NS or Prkch shRNA and treated with DMSO or IM (n=3). Data are represented as mean±SEM. (G) Relative viability of BCR-ABL+ human CML stem cells treated with DMSO, IM, TM or a combination of drugs (n=3). Data are represented as mean±SEM. *P≤0.05, **P≤0.01. Statistical tests and exact P values are provided in table 4.

Example 9. High Prkch Expression Contributes to the IM Resistance of CML Stem Cells Several experiments were performed to determine whether the high Prkch levels in murine CML stem cells contributes to their IM resistance. First the contribution of Prkch, and as a comparison BCR-ABL, to RAF/MEK/ERK signaling was assessed in murine CML stem cells. Prkch KD bone marrow cells were isolated from leukemic mice, permeabilized and incubated with an antibody against phosphorylated-ERK1/2 or IgG isotype antibody as a negative control, and then analyzed by FACS to determine the phosphorylated-ERK1/2 levels in CML progenitor and stem cells. FIG. 7A shows that knockdown of Prkch reduced levels of phosphorylated ERK1/2 in both CML progenitor and stem cells (see also FIG. 21A).

To evaluate the role of BCR-ABL, bone marrow cells were isolated from leukemic mice and treated with either IM or trametinib, and phosphorylated ERK1/2 was monitored as described above. FIG. 7B shows, as expected, that trametinib reduced phosphorylated ERK1/2 in both CML progenitor and stem cells (see also FIG. 21B). In contrast, IM reduced levels of phosphorylated ERK1/2 in IM-sensitive CML progenitor cells but not in IM-resistant CML stem cells. Collectively, these results indicate that in CML stem cells PKCη has a more prominent role than BCR-ABL in promoting RAF/MEK/ERK signaling.

Next, a series of experiments was performed to determine whether Prkch affects survival of CML stem cells after IM treatment. In the first experiment, mouse primary bone marrow cells were transduced with a retrovirus co-expressing BCR-ABL and either Prkch or a control non-silencing (NS) shRNA, followed by transplantation into lethally irradiated syngeneic mice. BCR-ABL+ murine stem cells (Lin−Sca1+Kit+) were isolated from the mice and IM sensitivity determined in a colony formation assay. The results in FIG. 7C show that Prkch knockdown markedly increased the IM sensitivity of CML stem cells. In the second experiment, mice with CML-like disease were treated with either vehicle or IM in parallel for two weeks, and then sacrificed at the same time followed by quantification of CML stem cells by FACS analysis. FIG. 7D shows, as expected, that IM treatment had little effect on the number of CML stem cells expressing a control NS shRNA, confirming that murine CML stem cells are IM-resistant. In contrast, IM treatment markedly reduced the number of Prkch KD CML stem cells. Annexin V staining revealed that IM treatment induced a higher level of apoptosis in Prkch KD compared to control CML stem cells (FIGS. 22A and B). Finally, combined treatment with IM and trametinib synergistically killed murine CML stem cells (FIG. 7E), which was due, at least in part, to the induction of apoptosis (FIGS. 22C and D). By contrast, treatment with IM and trametinib had negligible effect on normal murine hematopoietic stem cells (FIG. 23A).

Knockdown of PRKCH also increased the IM sensitivity of IM-resistant human CML stem cells (FIG. 7F). Moreover, treatment with both IM and trametinib had a substantially greater effect than either drug alone in killing human CML stem cells (FIG. 7G), and a negligible effect on normal human hematopoietic CD34+ cells and hematopoietic stem cells (CD34+CD38−) (FIG. 23B). Collectively, these results indicate that PRKCH is expressed at relatively high levels in both mouse and human CML stem cells and this contributes to their IM resistance.

REFERENCES AND NOTES

1. S. Faderl, M. Talpaz, Z. Estrov, S. O'Brien, R. Kurzrock, H. M. Kantarjian, The biology of chronic myeloid leukemia. N Engl J Med 341, 164-172 (1999).
2. M. W. Deininger, J. M. Goldman, J. V. Melo, The molecular biology of chronic myeloid leukemia. Blood 96, 3343-3356 (2000).
3. R. Kurzrock, H. M. Kantarjian, B. J. Druker, M. Talpaz, Philadelphia chromosome-positive leukemias: from basic mechanisms to molecular therapeutics. Ann Intern Med 138, 819-830 (2003).
4. J. Colicelli, ABL tyrosine kinases: evolution of function, regulation, and specificity. Sci Signal 3, re6 (2010).
5. L. S. Steelman, S. C. Pohnert, J. G. Shelton, R. A. Franklin, F. E. Bertrand, J. A. McCubrey, JAK/STAT, Raf/MEK/ERK, PI3K/Akt and BCR-ABL in cell cycle progression and leukemogenesis. Leukemia 18, 189-218 (2004).
6. X. An, A. K. Tiwari, Y. Sun, P. R. Ding, C. R. Ashby, Jr., Z. S. Chen, BCR-ABL tyrosine kinase inhibitors in the treatment of Philadelphia chromosome positive chronic myeloid leukemia: a review. Leuk Res 34, 1255-1268 (2010).
7. N. von Bubnoff, C. Peschel, J. Duyster, Resistance of Philadelphia-chromosome positive leukemia towards the kinase inhibitor imatinib (STI571, Glivec): a targeted oncoprotein strikes back. Leukemia 17, 829-838 (2003).
8. A. Quintas-Cardama, H. M. Kantarjian, J. E. Cortes, Mechanisms of primary and secondary resistance to imatinib in chronic myeloid leukemia. Cancer Control 16, 122-131 (2009).
9. E. Jabbour, H. Kantarjian, D. Jones, M. Talpaz, N. Bekele, S. O'Brien, X. Zhou, R. Luthra, G. Garcia-Manero, F. Giles, M. B. Rios, S. Verstovsek, J. Cortes, Frequency and clinical significance of BCR-ABL mutations in patients with chronic myeloid leukemia treated with imatinib mesylate. Leukemia 20, 1767-1773 (2006).
10. N. P. Shah, J. M. Nicoll, B. Nagar, M. E. Gorre, R. L. Paquette, J. Kuriyan, C. L. Sawyers, Multiple BCR-ABL kinase domain mutations confer polyclonal resistance to the tyrosine kinase inhibitor imatinib (STI571) in chronic phase and blast crisis chronic myeloid leukemia. Cancer cell 2, 117-125 (2002).
11. E. Weisberg, P. W. Manley, S. W. Cowan-Jacob, A. Hochhaus, J. D. Griffin, Second generation inhibitors of BCR-ABL for the treatment of imatinib-resistant chronic myeloid leukaemia. Nature reviews. Cancer 7, 345-356 (2007).
12. N. J. Donato, J. Y. Wu, J. Stapley, H. Lin, R. Arlinghaus, B. B. Aggarwal, S. Shishodia, M. Albitar, K. Hayes, H. Kantarjian, M. Talpaz, Imatinib mesylate resistance through BCR-ABL independence in chronic myelogenous leukemia. Cancer research 64, 672-677 (2004).
13. J. S. Khorashad, M. Anand, D. Marin, S. Saunders, T. Al-Jabary, A. Iqbal, S. Margerison, J. V. Melo, J. M. Goldman, J. F. Apperley, J. Kaeda, The presence of a BCR-ABL mutant allele in CML does not always explain clinical resistance to imatinib. Leukemia 20, 658-663 (2006).
14. M. Dean, T. Fojo, S. Bates, Tumour stem cells and drug resistance. Nature reviews. Cancer 5, 275-284 (2005).
15. S. M. Graham, H. G. Jorgensen, E. Allan, C. Pearson, M. J. Alcorn, L. Richmond, T. L. Holyoake, Primitive, quiescent, Philadelphia-positive stem cells from patients with chronic myeloid leukemia are insensitive to STI571 in vitro. Blood 99, 319-325 (2002).
16. A. S. Corbin, A. Agarwal, M. Loriaux, J. Cortes, M. W. Deininger, B. J. Druker, Human chronic myeloid leukemia stem cells are insensitive to imatinib despite inhibition of BCR-ABL activity. The Journal of clinical investigation 121, 396-409 (2011).
17. A. Hamilton, G. V. Helgason, M. Schemionek, B. Zhang, S. Myssina, E. K. Allan, F. E. Nicolini, C. Muller-Tidow, R. Bhatia, V. G. Brunton, S. Koschmieder, T. L. Holyoake, Chronic myeloid leukemia stem cells are not dependent on Bcr-Abl kinase activity for their survival. Blood 119, 1501-1510 (2012).
18. L. C. Andersson, K. Nilsson, C. G. Gahmberg, K562—a human erythroleukemic cell line. International journal of cancer. Journal international du cancer 23, 143-147 (1979).

19. J. M. Silva, M. Z. Li, K. Chang, W. Ge, M. C. Golding, R. J. Rickles, D. Siolas, G. Hu, P. J. Paddison, M. R. Schlabach, N. Sheth, J. Bradshaw, J. Burchard, A. Kulkarni, G. Cavet, R. Sachidanandam, W. R. McCombie, M. A. Cleary, S. J. Elledge, G. J. Hannon, Second-generation shRNA libraries covering the mouse and human genomes. Nat Genet 37, 1281-1288 (2005).
20. T. Ohkubo, T. Kamamoto, K. Kita, A. Hiraoka, Y. Yoshida, H. Uchino, A novel Ph1 chromosome positive cell line established from a patient with chronic myelogenous leukemia in blastic crisis. Leukemia research 9, 921-926 (1985).
21. G. Q. Daley, R. A. Van Etten, D. Baltimore, Induction of chronic myelogenous leukemia in mice by the P210bcr/abl gene of the Philadelphia chromosome. Science 247, 824-830 (1990).
22. S. Li, R. L. Ilaria, Jr., R. P. Million, G. Q. Daley, R. A. Van Etten, The P190, P210, and P230 forms of the BCR/ABL oncogene induce a similar chronic myeloid leukemia-like syndrome in mice but have different lymphoid leukemogenic activity. The Journal of experimental medicine 189, 1399-1412 (1999).
23. N. P. Shah, C. Tran, F. Y. Lee, P. Chen, D. Norris, C. L. Sawyers, Overriding imatinib resistance with a novel ABL kinase inhibitor. Science 305, 399-401 (2004).
24. N. J. Donato, J. Y. Wu, J. Stapley, G. Gallick, H. Lin, R. Arlinghaus, M. Talpaz, BCR-ABL independence and LYN kinase overexpression in chronic myelogenous leukemia cells selected for resistance to STI571. Blood 101, 690-698 (2003).
25. J. ten Hoeve, R. B. Arlinghaus, J. Q. Guo, N. Heisterkamp, J. Groffen, Tyrosine phosphorylation of CRKL in Philadelphia+leukemia. Blood 84, 1731-1736 (1994).
26. T. Takahashi, H. Ueno, M. Shibuya, VEGF activates protein kinase C-dependent, but Ras-independent Raf-MEK-MAP kinase pathway for DNA synthesis in primary endothelial cells. Oncogene 18, 2221-2230 (1999).
27. Y. Ueda, S. Hirai, S. Osada, A. Suzuki, K. Mizuno, S. Ohno, Protein kinase C activates the MEK-ERK pathway in a manner independent of Ras and dependent on Raf. The Journal of biological chemistry 271, 23512-23519 (1996).
28. R. M. Uht, S. Amos, P. M. Martin, A. E. Riggan, I. M. Hussaini, The protein kinase C-eta isoform induces proliferation in glioblastoma cell lines through an ERK/Elk-1 pathway. Oncogene 26, 2885-2893 (2007).
29. A. Aderem, The MARCKS brothers: a family of protein kinase C substrates. Cell 71, 713-716 (1992).
30. C. Wellbrock, M. Karasarides, R. Marais, The RAF proteins take centre stage. Nature reviews. Molecular cell biology 5, 875-885 (2004).
31. M. P. Carroll, W. S. May, Protein kinase C-mediated serine phosphorylation directly activates Raf-1 in murine hematopoietic cells. The Journal of biological chemistry 269, 1249-1256 (1994).
32. W. Kolch, G. Heidecker, G. Kochs, R. Hummel, H. Vahidi, H. Mischak, G. Finkenzeller, D. Marme, U. R. Rapp, Protein kinase C alpha activates RAF-1 by direct phosphorylation. Nature 364, 249-252 (1993).
33. T. Suzuki, B. C. Elias, A. Seth, L. Shen, J. R. Turner, F. Giorgianni, D. Desiderio, R. Guntaka, R. Rao, PKC eta regulates occludin phosphorylation and epithelial tight junction integrity. Proceedings of the National Academy of Sciences of the United States of America 106, 61-66 (2009).
34. H. Cai, U. Smola, V. Wixler, I. Eisenmann-Tappe, M. T. Diaz-Meco, J. Moscat, U. Rapp, G. M. Cooper, Role of diacylglycerol-regulated protein kinase C isotypes in growth factor activation of the Raf-1 protein kinase. Molecular and cellular biology 17, 732-741 (1997).
35. D. C. Schonwasser, R. M. Marais, C. J. Marshall, P. J. Parker, Activation of the mitogen-activated protein kinase/extracellular signal-regulated kinase pathway by conventional, novel, and atypical protein kinase C isotypes. Molecular and cellular biology 18, 790-798 (1998).
36. O. Sozeri, K. Vollmer, M. Liyanage, D. Frith, G. Kour, G. E. Mark, 3rd, S. Stabel, Activation of the c-Raf protein kinase by protein kinase C phosphorylation. Oncogene 7, 2259-2262 (1992).
37. J. M. Gerber, J. L. Gucwa, D. Esopi, M. Gurel, M. C. Haffner, M. Vala, W. G. Nelson, R. J. Jones, S. Yegnasubramanian, Genome-wide comparison of the transcriptomes of highly enriched normal and chronic myeloid leukemia stem and progenitor cell populations. Oncotarget 4, 715-728 (2013).
38. L. M. Packer, S. Rana, R. Hayward, T. O'Hare, C. A. Eide, A. Rebocho, S. Heidorn, M. S. Zabriskie, I. Niculescu-Duvaz, B. J. Druker, C. Springer, R. Marais, Nilotinib and MEK inhibitors induce synthetic lethality through paradoxical activation of RAF in drug-resistant chronic myeloid leukemia. Cancer cell 20, 715-727 (2011).
39. J. Hentschel, I. Rubio, M. Eberhart, C. Hipler, J. Schielher, K. Schubert, I. F. Loncarevic, U. Wittig, A. Baniahmad, F. von Eggeling, BCR-ABL- and Ras-independent activation of Raf as a novel mechanism of Imatinib resistance in CML. Int J Oncol 39, 585-591 (2011).
40. T. Nambu, N. Araki, A. Nakagawa, A. Kuniyasu, T. Kawaguchi, A. Hamada, H. Saito, Contribution of BCR-ABL-independent activation of ERK1/2 to acquired imatinib resistance in K562 chronic myeloid leukemia cells. Cancer Sci 101, 137-142 (2010).
41. R. Chakrabarti, J. Hwang, M. Andres Blanco, Y. Wei, M. Lukacisin, R. A. Romano, K. Smalley, S. Liu, Q. Yang, T. Ibrahim, L. Mercatali, D. Amadori, B. G. Haffty, S. Sinha, Y. Kang, Elf5 inhibits the epithelial-mesenchymal transition in mammary gland development and breast cancer metastasis by transcriptionally repressing Snail2. Nature cell biology 14, 1212-1222 (2012).
42. R. Escamilla-Hernandez, R. Chakrabarti, R. A. Romano, K. Smalley, Q. Zhu, W. Lai, M. S. Halfon, M. J. Buck, S. Sinha, Genome-wide search identifies Ccnd2 as a direct transcriptional target of Elf5 in mouse mammary gland. BMC molecular biology 11, 68 (2010).
43. M. Kalyuga, D. Gallego-Ortega, H. J. Lee, D. L. Roden, M. J. Cowley, C. E. Caldon, A. Stone, S. L. Allerdice, F. Valdes-Mora, R. Launchbury, A. L. Statham, N. Armstrong, M. C. Alles, A. Young, A. Egger, W. Au, C. L. Piggin, C. J. Evans, A. Ledger, T. Brummer, S. R. Oakes, W. Kaplan, J. M. Gee, R. I. Nicholson, R. L. Sutherland, A. Swarbrick, M. J. Naylor, S. J. Clark, J. S. Carroll, C. J. Ormandy, ELF5 suppresses estrogen sensitivity and underpins the acquisition of antiestrogen resistance in luminal breast cancer. PLoS biology 10, e1001461 (2012).
44. J. Mullenders, R. Bernards, Loss-of-function genetic screens as a tool to improve the diagnosis and treatment of cancer. Oncogene 28, 4409-4420 (2009).
45. D. Bruennert, A. Czibere, I. Bruns, R. Kronenwett, N. Gattermann, R. Haas, F. Neumann, Early in vivo changes of the transcriptome in Philadelphia chromosome-positive CD34+ cells from patients with chronic myelogenous leukaemia following imatinib therapy. Leukemia 23, 983-985 (2009).

46. J. P. Radich, H. Dai, M. Mao, V. Oehler, J. Schelter, B. Druker, C. Sawyers, N. Shah, W. Stock, C. L. Willman, S. Friend, P. S. Linsley, Gene expression changes associated with progression and response in chronic myeloid leukemia. Proceedings of the National Academy of Sciences of the United States of America 103, 2794-2799 (2006).
47. C. Gazin, N. Wajapeyee, S. Gobeil, C. M. Virbasius, M. R. Green, An elaborate pathway required for Ras-mediated epigenetic silencing. Nature 449, 1073-1077 (2007).
48. B. S. Carvalho, R. A. Irizarry, A framework for oligonucleotide microarray preprocessing. Bioinformatics 26, 2363-2367 (2010).
49. R. Ihaka, R. Gentleman, R: A language for data analysis and graphics. J. Comput. Graph Stat. 5, 299-314 (1996).
50. Y. Benjamini, Y. Hochberg, Controlling the false discovery rate: a practical and powerful approach to multiple testing. J. Roy. Statist. Soc. Ser. B 57, 289-300 (1995).
51. B. K. Slinker, The statistics of synergism. J Mol Cell Cardiol 30, 723-731 (1998).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating BCR-ABL independent imatinib mesylate (IM)-resistant chronic myeloid leukemia (CML) in a mammalian subject, the method comprising:
    detecting a level of PRKCH mRNA in a sample comprising leukemic cells from the subject;
    comparing the level of PRKCH mRNA in the sample to a reference level; and
    administering a combination of a BCR-ABL inhibitor and a MEK inhibitor to a subject who has a level of PRKCH mRNA above the reference level.

2. The method of claim 1, wherein the BCR-ABL inhibitor is imatinib, Nilotinib; Dasatinib; Bosutinib; Ponatinib; Bafetinib; or thiazol or a thiazol derivative.

3. The method of claim 2, wherein the BCR-ABL inhibitor is imatinib.

4. The method of claim 1, wherein the MEK inhibitor is Trametinib, Selumetinib, MEK162, PD-325901, cobimetinib, CL-1040, or PD035901.

5. The method of claim 4, wherein the MEK inhibitor is trametinib.

6. The method of claim 1, wherein the subject is human.

7. The method of claim 1, wherein the level of PRKCH mRNA is determined using RNA in situ hybridization, Southern or Northern analyses, polymerase chain reaction analyses and probe arrays.

8. A method for treating BCR-ABL independent imatinib mesylate (IM)-resistant chronic myeloid leukemia (CIVIL) in a mammalian subject, the method comprising:
    detecting a level of PKCeta protein in a sample comprising leukemic cells from the subject;
    comparing the level of PKCeta protein in the sample to a reference level; and
    administering a combination of a BCR-ABL inhibitor and a MEK inhibitor to a subject who has a level of PKCeta protein above the reference level.

9. The method of claim 8, wherein the BCR-ABL inhibitor is imatinib, Nilotinib; Dasatinib; Bosutinib; Ponatinib; Bafetinib; or thiazol or a thiazol derivative.

10. The method of claim 9, wherein the BCR-ABL inhibitor is imatinib.

11. The method of claim 8, wherein the MEK inhibitor is Trametinib, Selumetinib, MEK162, PD-325901, cobimetinib, CL-1040, or PD035901.

12. The method of claim 11, wherein the MEK inhibitor is trametinib.

13. The method of claim 8, wherein the subject is human.

14. The method of claim 8, wherein the level of PKCeta protein is determined using an immunoassay.

* * * * *

```
                        SEQUENCE LISTING

<160> NUMBER OF SEQ ID NOS: 115

<210> SEQ ID NO 1
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 1
atctgggtcc tgtcatcagc                                                    20

<210> SEQ ID NO 2
<211> LENGTH: 19
<212> TYPE: DNA
<213> ORGANISM: Artificial Sequence
<220> FEATURE:
<223> OTHER INFORMATION: Synthetically generated primer

<400> SEQUENCE: 2
gctgccttgg attggtctg                                                     19

<210> SEQ ID NO 3
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 3
aactagtaga agaccaggag                                                    20

<210> SEQ ID NO 4
<211> LENGTH: 19
<212> TYPE: DNA
<213> ORGANISM: Artificial Sequence
<220> FEATURE:
<223> OTHER INFORMATION: Synthetically generated Primer

<400> SEQUENCE: 4
cgaaagtctc tctgactgc                                                     19

<210> SEQ ID NO 5
<211> LENGTH: 21
<212> TYPE: DNA
<213> ORGANISM: Artificial sequence
<220> FEATURE:
<223> OTHER INFORMATION: Synthetically generated primer

<400> SEQUENCE: 5
```
cacctcaatg acagtggtca g        21

<210> SEQ ID NO 6
<211> LENGTH: 21
<212> TYPE: DNA
<213> ORGANISM: Artificial sequence
<220> FEATURE:
<223> OTHER INFORMATION: Synthetically generated primer

<400> SEQUENCE: 6
tggatcggat acccatagca g        21

<210> SEQ ID NO 7
<211> LENGTH: 18
<212> TYPE: DNA
<213> ORGANISM: Artificial sequence
<220> FEATURE:
<223> OTHER INFORMATION: Synthetically generated primer

<400> SEQUENCE: 7
tccagctcct cctactgg        18

<210> SEQ ID NO 8
<211> LENGTH: 20
<212> TYPE: DNA
<213> ORGANISM: Artificial sequence
<220> FEATURE:
<223> OTHER INFORMATION: Synthetically generated primer

<400> SEQUENCE: 8
cagaatactt gccattcacc        20

<210> SEQ ID NO 9
<211> LENGTH: 20
<212> TYPE: DNA
<213> ORGANISM: Artificial sequence
<220> FEATURE:
<223> OTHER INFORMATION: Synthetically generated primer

<400> SEQUENCE: 9
aggtggcgtt ggatcaacaa        20

<210> SEQ ID NO 10
<211> LENGTH: 20
<212> TYPE: DNA
<213> ORGANISM: Artificial sequence
<220> FEATURE:
<223> OTHER INFORMATION: Synthetically generated primer

<400> SEQUENCE: 10
ttaggccaat ggtcgcacag        20

<210> SEQ ID NO 11
<211> LENGTH: 20
<212> TYPE: DNA
<213> ORGANISM: Artificial sequence
<220> FEATURE:
<223> OTHER INFORMATION: Synthetically generated primer

<400> SEQUENCE: 11
ctgcacacca ctcctaaggc        20

<210> SEQ ID NO 12
<211> LENGTH: 19
<212> TYPE: DNA
<213> ORGANISM: Artificial sequence

```
<220> FEATURE:
<223> OTHER INFORMATION: Synthetically generated primer

<400> SEQUENCE: 12
caggcgcttt ttggtcagt                                          19

<210> SEQ ID NO 13
<211> LENGTH: 22
<212> TYPE: DNA
<213> ORGANISM: Artificial sequence
<220> FEATURE:
<223> OTHER INFORMATION: Synthetically generated primer

<400> SEQUENCE: 13
atggatgctg atctctcaca cc                                      22

<210> SEQ ID NO 14
<211> LENGTH: 23
<212> TYPE: DNA
<213> ORGANISM: Artificial sequence
<220> FEATURE:
<223> OTHER INFORMATION: Synthetically generated primer

<400> SEQUENCE: 14
ccatttcctt tgtagcgagt tcc                                     23

<210> SEQ ID NO 15
<211> LENGTH: 21
<212> TYPE: DNA
<213> ORGANISM: Artificial sequence
<220> FEATURE:
<223> OTHER INFORMATION: Synthetically generated primer

<400> SEQUENCE: 15
cctggtgttg tggaagtcac a                                       21

<210> SEQ ID NO 16
<211> LENGTH: 19
<212> TYPE: DNA
<213> ORGANISM: Artificial sequence
<220> FEATURE:
<223> OTHER INFORMATION: Synthetically generated primer

<400> SEQUENCE: 16
gctcaacgaa cccaccatc                                          19

<210> SEQ ID NO 17
<211> LENGTH: 23
<212> TYPE: DNA
<213> ORGANISM: Artificial sequence
<220> FEATURE:
<223> OTHER INFORMATION: Synthetically generated primer

<400> SEQUENCE: 17
gctgattcca actgcttgaa aac                                     23

<210> SEQ ID NO 18
<211> LENGTH: 24
<212> TYPE: DNA
<213> ORGANISM: Artificial sequence
<220> FEATURE:
<223> OTHER INFORMATION: Synthetically generated primer

<400> SEQUENCE: 18
cagttttctt caggagatag aagc                                    24
```

<210> SEQ ID NO 19
<211> LENGTH: 22
<212> TYPE: DNA
<213> ORGANISM: Artificial sequence
<220> FEATURE:
<223> OTHER INFORMATION: Synthetically generated primer

<400> SEQUENCE: 19
ccaaatgaag gctacttgga gt                                              22

<210> SEQ ID NO 20
<211> LENGTH: 21
<212> TYPE: DNA
<213> ORGANISM: Artificial sequence
<220> FEATURE:
<223> OTHER INFORMATION: Synthetically generated primer

<400> SEQUENCE: 20
tagagggtgt tagcgatctc g                                               21

<210> SEQ ID NO 21
<211> LENGTH: 23
<212> TYPE: DNA
<213> ORGANISM: Artificial sequence
<220> FEATURE:
<223> OTHER INFORMATION: Synthetically generated primer

<400> SEQUENCE: 21
atcgggctaa tcgagaaaaa gtc                                             23

<210> SEQ ID NO 22
<211> LENGTH: 21
<212> TYPE: DNA
<213> ORGANISM: Artificial sequence
<220> FEATURE:
<223> OTHER INFORMATION: Synthetically generated primer

<400> SEQUENCE: 22
tgctggtcta gttcttgctc c                                               21

<210> SEQ ID NO 23
<211> LENGTH: 21
<212> TYPE: DNA
<213> ORGANISM: Artificial sequence
<220> FEATURE:
<223> OTHER INFORMATION: Synthetically generated primer

<400> SEQUENCE: 23
agccggtcac ccatctatga a                                               21

<210> SEQ ID NO 24
<211> LENGTH: 21
<212> TYPE: DNA
<213> ORGANISM: Artificial sequence
<220> FEATURE:
<223> OTHER INFORMATION: Synthetically generated primer

<400> SEQUENCE: 24
tagagacaca tggtcggaca t                                               21

<210> SEQ ID NO 25
<211> LENGTH: 18
<212> TYPE: DNA
<213> ORGANISM: Artificial sequence
<220> FEATURE:
<223> OTHER INFORMATION: Synthetically generated primer

```
<400> SEQUENCE: 25
gctcactcag ctccaacc                                          18

<210> SEQ ID NO 26
<211> LENGTH: 18
<212> TYPE: DNA
<213> ORGANISM: Artificial sequence
<220> FEATURE:
<223> OTHER INFORMATION: Synthetically generated primer

<400> SEQUENCE: 26
tcaccagcct tggattcg                                          18

<210> SEQ ID NO 27
<211> LENGTH: 21
<212> TYPE: DNA
<213> ORGANISM: Artificial sequence
<220> FEATURE:
<223> OTHER INFORMATION: Synthetically generated primer

<400> SEQUENCE: 27
ttctggtctc cgagtcactc a                                      21

<210> SEQ ID NO 28
<211> LENGTH: 22
<212> TYPE: DNA
<213> ORGANISM: Artificial sequence
<220> FEATURE:
<223> OTHER INFORMATION: Synthetically generated primer

<400> SEQUENCE: 28
gccgtccact taatagggaa ct                                     22

<210> SEQ ID NO 29
<211> LENGTH: 19
<212> TYPE: DNA
<213> ORGANISM: Artificial sequence
<220> FEATURE:
<223> OTHER INFORMATION: Synthetically generated primer

<400> SEQUENCE: 29
cgcctgtctt cgtcacgtc                                         19

<210> SEQ ID NO 30
<211> LENGTH: 20
<212> TYPE: DNA
<213> ORGANISM: Artificial sequence
<220> FEATURE:
<223> OTHER INFORMATION: Synthetically generated primer

<400> SEQUENCE: 30
ctgctgaaag gtgagcaagt                                        20

<210> SEQ ID NO 31
<211> LENGTH: 19
<212> TYPE: DNA
<213> ORGANISM: Artificial sequence
<220> FEATURE:
<223> OTHER INFORMATION: Synthetically generated primer

<400> SEQUENCE: 31
gtggagtgcc agatgttgc                                         19

<210> SEQ ID NO 32
```

```
<211> LENGTH: 20
<212> TYPE: DNA
<213> ORGANISM: Artificial sequence
<220> FEATURE:
<223> OTHER INFORMATION: Synthetically generated primer

<400> SEQUENCE: 32
atcgatccac tgaatatgcg                                              20

<210> SEQ ID NO 33
<211> LENGTH: 23
<212> TYPE: DNA
<213> ORGANISM: Artificial sequence
<220> FEATURE:
<223> OTHER INFORMATION: Synthetically generated primer

<400> SEQUENCE: 33
gtgacttgat gttccacatt cag                                          23

<210> SEQ ID NO 34
<211> LENGTH: 25
<212> TYPE: DNA
<213> ORGANISM: Artificial sequence
<220> FEATURE:
<223> OTHER INFORMATION: Synthetically generated primer

<400> SEQUENCE: 34
attgtccagt ttcagatctc tatag                                        25

<210> SEQ ID NO 35
<211> LENGTH: 18
<212> TYPE: DNA
<213> ORGANISM: Artificial sequence
<220> FEATURE:
<223> OTHER INFORMATION: Synthetically generated primer

<400> SEQUENCE: 35
cacgccggaa aagcgagc                                                18

<210> SEQ ID NO 36
<211> LENGTH: 20
<212> TYPE: DNA
<213> ORGANISM: Artificial sequence
<220> FEATURE:
<223> OTHER INFORMATION: Synthetically generated primer

<400> SEQUENCE: 36
ggatcagtcg cagaatttcc                                              20

<210> SEQ ID NO 37
<211> LENGTH: 23
<212> TYPE: DNA
<213> ORGANISM: Artificial sequence
<220> FEATURE:
<223> OTHER INFORMATION: Synthetically generated primer

<400> SEQUENCE: 37
gactttgtgg acgaagtaag agc                                          23

<210> SEQ ID NO 38
<211> LENGTH: 21
<212> TYPE: DNA
<213> ORGANISM: Artificial sequence
<220> FEATURE:
<223> OTHER INFORMATION: Synthetically generated primer

<400> SEQUENCE: 38
```
gctttccaga ggttcagtct c                                              21

<210> SEQ ID NO 39
<211> LENGTH: 18
<212> TYPE: DNA
<213> ORGANISM: Artificial sequence
<220> FEATURE:
<223> OTHER INFORMATION: Synthetically generated primer

<400> SEQUENCE: 39
ctgcaagcag cagtgagg                                                  18

<210> SEQ ID NO 40
<211> LENGTH: 19
<212> TYPE: DNA
<213> ORGANISM: Artificial sequence
<220> FEATURE:
<223> OTHER INFORMATION: Synthetically generated primer

<400> SEQUENCE: 40
aaccggcagg aagactgag                                                 19

<210> SEQ ID NO 41
<211> LENGTH: 19
<212> TYPE: DNA
<213> ORGANISM: Artificial sequence
<220> FEATURE:
<223> OTHER INFORMATION: Synthetically generated primer

<400> SEQUENCE: 41
gaccccaaga ttcagaagg                                                 19

<210> SEQ ID NO 42
<211> LENGTH: 19
<212> TYPE: DNA
<213> ORGANISM: Artificial sequence
<220> FEATURE:
<223> OTHER INFORMATION: Synthetically generated primer

<400> SEQUENCE: 42
tccggggaat cttctatcc                                                 19

<210> SEQ ID NO 43
<211> LENGTH: 21
<212> TYPE: DNA
<213> ORGANISM: Artificial sequence
<220> FEATURE:
<223> OTHER INFORMATION: Synthetically generated primer

<400> SEQUENCE: 43
tcgttctcgc ccgcaattta g                                              21

<210> SEQ ID NO 44
<211> LENGTH: 21
<212> TYPE: DNA
<213> ORGANISM: Artificial sequence
<220> FEATURE:
<223> OTHER INFORMATION: Synthetically generated primer

<400> SEQUENCE: 44
gataaggacg gctccgtttt g                                              21

<210> SEQ ID NO 45
<211> LENGTH: 22
<212> TYPE: DNA

```
<213> ORGANISM: Artificial sequence
<220> FEATURE:
<223> OTHER INFORMATION: Synthetically generated primer

<400> SEQUENCE: 45
tcggcttcta taacttctgc ct                                            22

<210> SEQ ID NO 46
<211> LENGTH: 20
<212> TYPE: DNA
<213> ORGANISM: Artificial sequence
<220> FEATURE:
<223> OTHER INFORMATION: Synthetically generated primer

<400> SEQUENCE: 46
ctgttgcact gggctaggag                                               20

<210> SEQ ID NO 47
<211> LENGTH: 18
<212> TYPE: DNA
<213> ORGANISM: Artificial sequence
<220> FEATURE:
<223> OTHER INFORMATION: Synthetically generated primer

<400> SEQUENCE: 47
tgcctatccg ctgcatcc                                                 18

<210> SEQ ID NO 48
<211> LENGTH: 20
<212> TYPE: DNA
<213> ORGANISM: Artificial sequence
<220> FEATURE:
<223> OTHER INFORMATION: Synthetically generated primer

<400> SEQUENCE: 48
ttcatggggc agcgattagc                                               20

<210> SEQ ID NO 49
<211> LENGTH: 20
<212> TYPE: DNA
<213> ORGANISM: Artificial sequence
<220> FEATURE:
<223> OTHER INFORMATION: Synthetically generated primer

<400> SEQUENCE: 49
atagcagcgg caatacgtgg                                               20

<210> SEQ ID NO 50
<211> LENGTH: 23
<212> TYPE: DNA
<213> ORGANISM: Artificial sequence
<220> FEATURE:
<223> OTHER INFORMATION: Synthetically generated primer

<400> SEQUENCE: 50
gaagacacat tagaggcagt gaa                                           23

<210> SEQ ID NO 51
<211> LENGTH: 21
<212> TYPE: DNA
<213> ORGANISM: Artificial sequence
<220> FEATURE:
<223> OTHER INFORMATION: Synthetically generated primer

<400> SEQUENCE: 51
gaagcagggc tactacaacc a                                             21
```

<210> SEQ ID NO 52
<211> LENGTH: 21
<212> TYPE: DNA
<213> ORGANISM: Artificial sequence
<220> FEATURE:
<223> OTHER INFORMATION: Synthetically generated primer

<400> SEQUENCE: 52
cggcctcatt gttatgcagg t                                              21

<210> SEQ ID NO 53
<211> LENGTH: 19
<212> TYPE: DNA
<213> ORGANISM: Artificial sequence
<220> FEATURE:
<223> OTHER INFORMATION: Synthetically generated primer

<400> SEQUENCE: 53
gagaggggaa cagcgagag                                                 19

<210> SEQ ID NO 54
<211> LENGTH: 20
<212> TYPE: DNA
<213> ORGANISM: Artificial sequence
<220> FEATURE:
<223> OTHER INFORMATION: Synthetically generated primer

<400> SEQUENCE: 54
cagtctcagg ccagcttctc                                                20

<210> SEQ ID NO 55
<211> LENGTH: 22
<212> TYPE: DNA
<213> ORGANISM: Artificial sequence
<220> FEATURE:
<223> OTHER INFORMATION: Synthetically generated primer

<400> SEQUENCE: 55
tagtcctccc agcaaatgta ag                                             22

<210> SEQ ID NO 56
<211> LENGTH: 20
<212> TYPE: DNA
<213> ORGANISM: Artificial sequence
<220> FEATURE:
<223> OTHER INFORMATION: Synthetically generated primer

<400> SEQUENCE: 56
gtcttcctcc tcctgcatag                                                20

<210> SEQ ID NO 57
<211> LENGTH: 23
<212> TYPE: DNA
<213> ORGANISM: Artificial sequence
<220> FEATURE:
<223> OTHER INFORMATION: Synthetically generated primer

<400> SEQUENCE: 57
ttctgtctgc cctttattcc tcc                                            23

<210> SEQ ID NO 58
<211> LENGTH: 22
<212> TYPE: DNA
<213> ORGANISM: Artificial sequence
<220> FEATURE:

```
<223> OTHER INFORMATION: Synthetically generated primer

<400> SEQUENCE: 58
tcttacttct ctcacggcat ct                                              22

<210> SEQ ID NO 59
<211> LENGTH: 22
<212> TYPE: DNA
<213> ORGANISM: Artificial sequence
<220> FEATURE:
<223> OTHER INFORMATION: Synthetically generated primer

<400> SEQUENCE: 59
aagctggatg tccattatgc tc                                              22

<210> SEQ ID NO 60
<211> LENGTH: 20
<212> TYPE: DNA
<213> ORGANISM: Artificial sequence
<220> FEATURE:
<223> OTHER INFORMATION: Synthetically generated primer

<400> SEQUENCE: 60
tctgtaggag gtgacgtctg                                                 20

<210> SEQ ID NO 61
<211> LENGTH: 20
<212> TYPE: DNA
<213> ORGANISM: Artificial sequence
<220> FEATURE:
<223> OTHER INFORMATION: Synthetically generated primer

<400> SEQUENCE: 61
tctggatgcc agggtgattc                                                 20

<210> SEQ ID NO 62
<211> LENGTH: 24
<212> TYPE: DNA
<213> ORGANISM: Artificial sequence
<220> FEATURE:
<223> OTHER INFORMATION: Synthetically generated primer

<400> SEQUENCE: 62
tattcatcca ggaaatgtaa gcag                                            24

<210> SEQ ID NO 63
<211> LENGTH: 22
<212> TYPE: DNA
<213> ORGANISM: Artificial sequence
<220> FEATURE:
<223> OTHER INFORMATION: Synthetically generated primer

<400> SEQUENCE: 63
gaaactggga ttttcaccaa gg                                              22

<210> SEQ ID NO 64
<211> LENGTH: 23
<212> TYPE: DNA
<213> ORGANISM: Artificial sequence
<220> FEATURE:
<223> OTHER INFORMATION: Synthetically generated primer

<400> SEQUENCE: 64
tcctgaagat acttcagttt ctc                                             23
```

```
<210> SEQ ID NO 65
<211> LENGTH: 24
<212> TYPE: DNA
<213> ORGANISM: Artificial sequence
<220> FEATURE:
<223> OTHER INFORMATION: Synthetically generated primer

<400> SEQUENCE: 65
tatgtgtata tctacaggtc tgac                                              24

<210> SEQ ID NO 66
<211> LENGTH: 22
<212> TYPE: DNA
<213> ORGANISM: Artificial sequence
<220> FEATURE:
<223> OTHER INFORMATION: Synthetically generated primer

<400> SEQUENCE: 66
accacacttg aagagttttt gc                                                22

<210> SEQ ID NO 67
<211> LENGTH: 25
<212> TYPE: DNA
<213> ORGANISM: Artificial sequence
<220> FEATURE:
<223> OTHER INFORMATION: Synthetically generated primer

<400> SEQUENCE: 67
gtaattttga tattgtctct ggaac                                             25

<210> SEQ ID NO 68
<211> LENGTH: 24
<212> TYPE: DNA
<213> ORGANISM: Artificial sequence
<220> FEATURE:
<223> OTHER INFORMATION: Synthetically generated primer

<400> SEQUENCE: 68
cttcttttcg gtataatctg aagc                                              24

<210> SEQ ID NO 69
<211> LENGTH: 20
<212> TYPE: DNA
<213> ORGANISM: Artificial sequence
<220> FEATURE:
<223> OTHER INFORMATION: Synthetically generated primer

<400> SEQUENCE: 69
ctcaccctat gccattgtgc                                                   20

<210> SEQ ID NO 70
<211> LENGTH: 22
<212> TYPE: DNA
<213> ORGANISM: Artificial sequence
<220> FEATURE:
<223> OTHER INFORMATION: Synthetically generated primer

<400> SEQUENCE: 70
cgaaagcact cttctgtttc ac                                                22

<210> SEQ ID NO 71
<211> LENGTH: 20
<212> TYPE: DNA
<213> ORGANISM: Artificial sequence
<220> FEATURE:
<223> OTHER INFORMATION: Synthetically generated primer
```

```
<400> SEQUENCE: 71
tgcctttgag catcagacag                                              20

<210> SEQ ID NO 72
<211> LENGTH: 20
<212> TYPE: DNA
<213> ORGANISM: Artificial sequence
<220> FEATURE:
<223> OTHER INFORMATION: Synthetically generated primer

<400> SEQUENCE: 72
tactggtcgc agcagaattg                                              20

<210> SEQ ID NO 73
<211> LENGTH: 20
<212> TYPE: DNA
<213> ORGANISM: Artificial sequence
<220> FEATURE:
<223> OTHER INFORMATION: Synthetically generated primer

<400> SEQUENCE: 73
gtgatgacct tggcacagag                                              20

<210> SEQ ID NO 74
<211> LENGTH: 20
<212> TYPE: DNA
<213> ORGANISM: Artificial sequence
<220> FEATURE:
<223> OTHER INFORMATION: Synthetically generated primer

<400> SEQUENCE: 74
cattccagca gcagcacatc                                              20

<210> SEQ ID NO 75
<211> LENGTH: 22
<212> TYPE: DNA
<213> ORGANISM: Artificial sequence
<220> FEATURE:
<223> OTHER INFORMATION: Synthetically generated primer

<400> SEQUENCE: 75
acatctgaga ttgcagtgag tg                                           22

<210> SEQ ID NO 76
<211> LENGTH: 21
<212> TYPE: DNA
<213> ORGANISM: Artificial sequence
<220> FEATURE:
<223> OTHER INFORMATION: Synthetically generated primer

<400> SEQUENCE: 76
tactactatc cagcagtgca g                                            21

<210> SEQ ID NO 77
<211> LENGTH: 19
<212> TYPE: DNA
<213> ORGANISM: Artificial sequence
<220> FEATURE:
<223> OTHER INFORMATION: Synthetically generated primer

<400> SEQUENCE: 77
tgggtgtcca aggtctctc                                               19

<210> SEQ ID NO 78
<211> LENGTH: 22
```

<212> TYPE: DNA
<213> ORGANISM: Artificial sequence
<220> FEATURE:
<223> OTHER INFORMATION: Synthetically generated primer

<400> SEQUENCE: 78
ctcccactga ataggtgctt tg                                    22

<210> SEQ ID NO 79
<211> LENGTH: 23
<212> TYPE: DNA
<213> ORGANISM: Artificial sequence
<220> FEATURE:
<223> OTHER INFORMATION: Synthetically generated primer

<400> SEQUENCE: 79
ctgccagtgt tctaggaaac tac                                   23

<210> SEQ ID NO 80
<211> LENGTH: 21
<212> TYPE: DNA
<213> ORGANISM: Artificial sequence
<220> FEATURE:
<223> OTHER INFORMATION: Synthetically generated primer

<400> SEQUENCE: 80
atgtgagtaa cggccactag g                                     21

<210> SEQ ID NO 81
<211> LENGTH: 19
<212> TYPE: DNA
<213> ORGANISM: Artificial sequence
<220> FEATURE:
<223> OTHER INFORMATION: Synthetically generated primer

<400> SEQUENCE: 81
tgaggacgca ggagtgaac                                        19

<210> SEQ ID NO 82
<211> LENGTH: 22
<212> TYPE: DNA
<213> ORGANISM: Artificial sequence
<220> FEATURE:
<223> OTHER INFORMATION: Synthetically generated primer

<400> SEQUENCE: 82
cgtcctttgt aagactgaag tc                                    22

<210> SEQ ID NO 83
<211> LENGTH: 21
<212> TYPE: DNA
<213> ORGANISM: Artificial sequence
<220> FEATURE:
<223> OTHER INFORMATION: Synthetically generated primer

<400> SEQUENCE: 83
tccggcacga tgaagttcaa t                                     21

<210> SEQ ID NO 84
<211> LENGTH: 20
<212> TYPE: DNA
<213> ORGANISM: Artificial sequence
<220> FEATURE:
<223> OTHER INFORMATION: Synthetically generated primer

<400> SEQUENCE: 84
tacgctcacc gtcaggtagg                                              20

<210> SEQ ID NO 85
<211> LENGTH: 19
<212> TYPE: DNA
<213> ORGANISM: Artificial sequence
<220> FEATURE:
<223> OTHER INFORMATION: Synthetically generated primer

<400> SEQUENCE: 85
acgacgtaga cggcaatgg                                               19

<210> SEQ ID NO 86
<211> LENGTH: 20
<212> TYPE: DNA
<213> ORGANISM: Artificial sequence
<220> FEATURE:
<223> OTHER INFORMATION: Synthetically generated primer

<400> SEQUENCE: 86
ccgcttttct ggggtgtttt                                              20

<210> SEQ ID NO 87
<211> LENGTH: 21
<212> TYPE: DNA
<213> ORGANISM: Artificial sequence
<220> FEATURE:
<223> OTHER INFORMATION: Synthetically generated primer

<400> SEQUENCE: 87
cttctgctca gggttttcaa g                                            21

<210> SEQ ID NO 88
<211> LENGTH: 21
<212> TYPE: DNA
<213> ORGANISM: Artificial sequence
<220> FEATURE:
<223> OTHER INFORMATION: Synthetically generated primer

<400> SEQUENCE: 88
atgtcttctc tctccaaggt g                                            21

<210> SEQ ID NO 89
<211> LENGTH: 21
<212> TYPE: DNA
<213> ORGANISM: Artificial sequence
<220> FEATURE:
<223> OTHER INFORMATION: Synthetically generated primer

<400> SEQUENCE: 89
agtatgactg tagtgcccta c                                            21

<210> SEQ ID NO 90
<211> LENGTH: 18
<212> TYPE: DNA
<213> ORGANISM: Artificial sequence
<220> FEATURE:
<223> OTHER INFORMATION: Synthetically generated primer

<400> SEQUENCE: 90
caggacctgt ccaggcac                                                18

<210> SEQ ID NO 91
<211> LENGTH: 20
<212> TYPE: DNA
<213> ORGANISM: Artificial sequence
<220> FEATURE:
<223> OTHER INFORMATION: Synthetically generated primer

<400> SEQUENCE: 91
ctgcttttct gcgagccaac                                              20

<210> SEQ ID NO 92
<211> LENGTH: 21
<212> TYPE: DNA
<213> ORGANISM: Artificial sequence
<220> FEATURE:
<223> OTHER INFORMATION: Synthetically generated primer

<400> SEQUENCE: 92
tgtcgttttg atcggacatc c                                            21

<210> SEQ ID NO 93
<211> LENGTH: 21
<212> TYPE: DNA
<213> ORGANISM: Artificial sequence
<220> FEATURE:
<223> OTHER INFORMATION: Synthetically generated primer

<400> SEQUENCE: 93
gtatccgccc tcaattcata g                                            21

<210> SEQ ID NO 94
<211> LENGTH: 21
<212> TYPE: DNA
<213> ORGANISM: Artificial sequence
<220> FEATURE:
<223> OTHER INFORMATION: Synthetically generated primer

<400> SEQUENCE: 94
ctccgttttg ccttccaatg c                                            21

<210> SEQ ID NO 95
<211> LENGTH: 21
<212> TYPE: DNA
<213> ORGANISM: Artificial sequence
<220> FEATURE:
<223> OTHER INFORMATION: Synthetically generated primer

<400> SEQUENCE: 95
cagcgttggt ttttgtctcc c                                            21

<210> SEQ ID NO 96
<211> LENGTH: 21
<212> TYPE: DNA
<213> ORGANISM: Artificial sequence
<220> FEATURE:
<223> OTHER INFORMATION: Synthetically generated primer

<400> SEQUENCE: 96
gaggagagcg tagaacatca g                                            21

<210> SEQ ID NO 97
<211> LENGTH: 21
<212> TYPE: DNA
<213> ORGANISM: Artificial sequence
<220> FEATURE:
<223> OTHER INFORMATION: Synthetically generated primer

<400> SEQUENCE: 97
cccggcttcg actacaagtt c                                            21

<210> SEQ ID NO 98
<211> LENGTH: 21
<212> TYPE: DNA
<213> ORGANISM: Artificial sequence
<220> FEATURE:
<223> OTHER INFORMATION: Synthetically generated primer

<400> SEQUENCE: 98
tcagggcatt tgaagactcc t                                                 21

<210> SEQ ID NO 99
<211> LENGTH: 23
<212> TYPE: DNA
<213> ORGANISM: Artificial sequence
<220> FEATURE:
<223> OTHER INFORMATION: Synthetically generated primer

<400> SEQUENCE: 99
tgctacaact tcaggaaaag ctc                                               23

<210> SEQ ID NO 100
<211> LENGTH: 23
<212> TYPE: DNA
<213> ORGANISM: Artificial sequence
<220> FEATURE:
<223> OTHER INFORMATION: Synthetically generated primer

<400> SEQUENCE: 100
gtctggagca tctgtaaatc atc                                               23

<210> SEQ ID NO 101
<211> LENGTH: 21
<212> TYPE: DNA
<213> ORGANISM: Artificial sequence
<220> FEATURE:
<223> OTHER INFORMATION: Synthetically generated primer

<400> SEQUENCE: 101
cccgatgcca tcattgtgat c                                                 21

<210> SEQ ID NO 102
<211> LENGTH: 19
<212> TYPE: DNA
<213> ORGANISM: Artificial sequence
<220> FEATURE:
<223> OTHER INFORMATION: Synthetically generated primer

<400> SEQUENCE: 102
gtagggagtc gagaggctg                                                    19

<210> SEQ ID NO 103
<211> LENGTH: 35
<212> TYPE: DNA
<213> ORGANISM: Artificial sequence
<220> FEATURE:
<223> OTHER INFORMATION: Synthetically generated primer

<400> SEQUENCE: 103
ataggttaac gccaccatgt cgtccggcac gatga                                  35

<210> SEQ ID NO 104
<211> LENGTH: 31
<212> TYPE: DNA
<213> ORGANISM: Artificial sequence
<220> FEATURE:
<223> OTHER INFORMATION: Synthetically generated primer

<400> SEQUENCE: 104
ataggaattc ctacagttgc aattccggtg a                                      31

<210> SEQ ID NO 105
<211> LENGTH: 34
<212> TYPE: DNA
<213> ORGANISM: Artificial sequence
<220> FEATURE:
<223> OTHER INFORMATION: Synthetically generated primer

<400> SEQUENCE: 105
atagacgcgt ttcttggctt tatatatctt gtgg                                   34

<210> SEQ ID NO 106
<211> LENGTH: 30
<212> TYPE: DNA
<213> ORGANISM: Artificial sequence
<220> FEATURE:
<223> OTHER INFORMATION: Synthetically generated primer

<400> SEQUENCE: 106
atagacgcgt caaagtggat ctctgctgtc                                        30

<210> SEQ ID NO 107
<211> LENGTH: 20
<212> TYPE: DNA
<213> ORGANISM: Artificial sequence
<220> FEATURE:
<223> OTHER INFORMATION: Synthetically generated primer

<400> SEQUENCE: 107
aggaggagaa gcaagaggag                                                   20

<210> SEQ ID NO 108
<211> LENGTH: 18
<212> TYPE: DNA
<213> ORGANISM: Artificial sequence
<220> FEATURE:
<223> OTHER INFORMATION: Synthetically generated primer

<400> SEQUENCE: 108
ccgaccgtcc cttccaag                                                     18

<210> SEQ ID NO 109
<211> LENGTH: 20
<212> TYPE: DNA
<213> ORGANISM: Artificial sequence
<220> FEATURE:
<223> OTHER INFORMATION: Synthetically generated primer

<400> SEQUENCE: 109
gacctttcct gctctatgtg                                                   20

<210> SEQ ID NO 110
<211> LENGTH: 21
<212> TYPE: DNA
<213> ORGANISM: Artificial sequence
<220> FEATURE:
<223> OTHER INFORMATION: Synthetically generated primer

<400> SEQUENCE: 110
ctgcagaggc taattacaca g                                                 21

<210> SEQ ID NO 111

```
<211> LENGTH: 20
<212> TYPE: DNA
<213> ORGANISM: Artificial sequence
<220> FEATURE:
<223> OTHER INFORMATION: Synthetically generated primer

<400> SEQUENCE: 111
catagcagcg taggctaaaa                                              20

<210> SEQ ID NO 112
<211> LENGTH: 22
<212> TYPE: DNA
<213> ORGANISM: Artificial sequence
<220> FEATURE:
<223> OTHER INFORMATION: Synthetically generated primer

<400> SEQUENCE: 112
cggaagaaat tgcctcttct ag                                           22

<210> SEQ ID NO 113
<211> LENGTH: 31
<212> TYPE: DNA
<213> ORGANISM: Artificial sequence
<220> FEATURE:
<223> OTHER INFORMATION: Synthetically generated primer

<400> SEQUENCE: 113
ataggctagc gttctgaaca gggccttaga g                                 31

<210> SEQ ID NO 114
<211> LENGTH: 30
<212> TYPE: DNA
<213> ORGANISM: Artificial sequence
<220> FEATURE:
<223> OTHER INFORMATION: Synthetically generated primer

<400> SEQUENCE: 114
atagaagctt gatgcggacc ctcaaatagc                                   30

<210> SEQ ID NO 115
<211> LENGTH: 1130
<212> TYPE: PRT
<213> ORGANISM: Homo sapiens

<400> SEQUENCE: 115

Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
```

```
                130               135                140
    Ile Asn Gly Ser Phe Leu Val Arg Glu Ser Glu Ser Ser Pro Gly Gln
    145                 150                 155                 160

Arg Ser Ile Ser Leu Arg Tyr Glu Gly Arg Val Tyr His Tyr Arg Ile
                        165                 170                 175

Asn Thr Ala Ser Asp Gly Lys Leu Tyr Val Ser Ser Glu Ser Arg Phe
                180                 185                 190

Asn Thr Leu Ala Glu Leu Val His His Ser Thr Val Ala Asp Gly
                195                 200                 205

Leu Ile Thr Thr Leu His Tyr Pro Ala Pro Lys Arg Asn Lys Pro Thr
                210                 215                 220

Val Tyr Gly Val Ser Pro Asn Tyr Asp Lys Trp Glu Met Glu Arg Thr
    225                 230                 235                 240

Asp Ile Thr Met Lys His Lys Leu Gly Gly Gln Tyr Gly Glu Val
                        245                 250                 255

Tyr Glu Gly Val Trp Lys Lys Tyr Ser Leu Thr Val Ala Val Lys Thr
                        260                 265                 270

Leu Lys Glu Asp Thr Met Glu Val Glu Glu Phe Leu Lys Glu Ala Ala
                275                 280                 285

Val Met Lys Glu Ile Lys His Pro Asn Leu Val Gln Leu Leu Gly Val
    290                 295                 300

Cys Thr Arg Glu Pro Pro Phe Tyr Ile Ile Thr Glu Phe Met Thr Tyr
    305                 310                 315                 320

Gly Asn Leu Leu Asp Tyr Leu Arg Glu Cys Asn Arg Gln Glu Val Asn
                        325                 330                 335

Ala Val Val Leu Leu Tyr Met Ala Thr Gln Ile Ser Ser Ala Met Glu
                        340                 345                 350

Tyr Leu Glu Lys Lys Asn Phe Ile His Arg Asp Leu Ala Ala Arg Asn
                355                 360                 365

Cys Leu Val Gly Glu Asn His Leu Val Lys Val Ala Asp Phe Gly Leu
    370                 375                 380

Ser Arg Leu Met Thr Gly Asp Thr Tyr Thr Ala His Ala Gly Ala Lys
    385                 390                 395                 400

Phe Pro Ile Lys Trp Thr Ala Pro Glu Ser Leu Ala Tyr Asn Lys Phe
                        405                 410                 415

Ser Ile Lys Ser Asp Val Trp Ala Phe Gly Val Leu Leu Trp Glu Ile
                        420                 425                 430

Ala Thr Tyr Gly Met Ser Pro Tyr Pro Gly Ile Asp Leu Ser Gln Val
                435                 440                 445

Tyr Glu Leu Leu Glu Lys Asp Tyr Arg Met Glu Arg Pro Glu Gly Cys
                450                 455                 460

Pro Glu Lys Val Tyr Glu Leu Met Arg Ala Cys Trp Gln Trp Asn Pro
    465                 470                 475                 480

Ser Asp Arg Pro Ser Phe Ala Glu Ile His Gln Ala Phe Glu Thr Met
                        485                 490                 495

Phe Gln Glu Ser Ser Ile Ser Asp Glu Val Glu Lys Glu Leu Gly Lys
                500                 505                 510

Gln Gly Val Arg Gly Ala Val Ser Thr Leu Leu Gln Ala Pro Glu Leu
                515                 520                 525

Pro Thr Lys Thr Arg Thr Ser Arg Arg Ala Ala Glu His Arg Asp Thr
                530                 535                 540

Thr Asp Val Pro Glu Met Pro His Ser Lys Gly Gln Gly Glu Ser Asp
    545                 550                 555                 560
```

-continued

Pro Leu Asp His Glu Pro Ala Val Ser Pro Leu Leu Pro Arg Lys Glu
              565                 570                 575

Arg Gly Pro Pro Glu Gly Gly Leu Asn Glu Asp Glu Arg Leu Leu Pro
              580                 585                 590

Lys Asp Lys Lys Thr Asn Leu Phe Ser Ala Leu Ile Lys Lys Lys Lys
              595                 600                 605

Lys Thr Ala Pro Thr Pro Pro Lys Arg Ser Ser Phe Arg Glu Met
              610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
              645                 650                 655

Ala Lys Ser Pro Lys Pro Ser Asn Gly Ala Gly Val Pro Asn Gly Ala
              660                 665                 670

Leu Arg Glu Ser Gly Gly Ser Gly Phe Arg Ser Pro His Leu Trp Lys
              675                 680                 685

Lys Ser Ser Thr Leu Thr Ser Ser Arg Leu Ala Thr Gly Glu Glu Glu
              690                 695                 700

Gly Gly Gly Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
              725                 730                 735

Pro Arg Asp Leu Gln Ser Thr Gly Arg Gln Phe Asp Ser Ser Thr Phe
              740                 745                 750

Gly Gly His Lys Ser Glu Lys Pro Ala Leu Pro Arg Lys Arg Ala Gly
              755                 760                 765

Glu Asn Arg Ser Asp Gln Val Thr Arg Gly Thr Val Thr Pro Pro
              770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
              805                 810                 815

Pro Leu Arg Arg Gln Val Thr Val Ala Pro Ala Ser Gly Leu Pro His
              820                 825                 830

Lys Glu Glu Ala Glu Lys Gly Ser Ala Leu Gly Thr Pro Ala Ala Ala
              835                 840                 845

Glu Pro Val Thr Pro Thr Ser Lys Ala Gly Ser Gly Ala Pro Gly Gly
              850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
              885                 890                 895

Pro Ala Pro Pro Pro Pro Ala Ala Ser Ala Gly Lys Ala Gly Gly
              900                 905                 910

Lys Pro Ser Gln Ser Pro Ser Gln Glu Ala Ala Gly Glu Ala Val Leu
              915                 920                 925

Gly Ala Lys Thr Lys Ala Thr Ser Leu Val Asp Ala Val Asn Ser Asp
              930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
              965                 970                 975

```
Ser Pro Ala Pro Val Pro Ser Thr Leu Pro Ser Ala Ser Ser Ala Leu
            980                 985                 990

Ala Gly Asp Gln Pro Ser Ser Thr  Ala Phe Ile Pro Leu  Ile Ser Thr
        995                 1000                1005

Arg Val  Ser Leu Arg Lys Thr  Arg Gln Pro Pro Glu  Arg Ile Ala
    1010             1015                 1020

Ser Gly Ala Ile Thr Lys Gly  Val Val Leu Asp Ser  Thr Glu Ala
    1025             1030                 1035

Leu Cys  Leu Ala Ile Ser Arg  Asn Ser Glu Gln Met  Ala Ser His
    1040             1045                 1050

Ser Ala Val Leu Glu Ala Gly  Lys Asn Leu Tyr Thr  Phe Cys Val
    1055             1060                 1065

Ser Tyr  Val Asp Ser Ile Gln  Gln Met Arg Asn Lys  Phe Ala Phe
    1070             1075                 1080

Arg Glu  Ala Ile Asn Lys Leu  Glu Asn Asn Leu Arg  Glu Leu Gln
    1085             1090                 1095

Ile Cys  Pro Ala Thr Ala Gly  Ser Gly Pro Ala Ala  Thr Gln Asp
    1100             1105                 1110

Phe Ser  Lys Leu Leu Ser Ser  Val Lys Glu Ile Ser  Asp Ile Val
    1115             1120                 1125

Gln Arg
    1130
```